United States Patent
Ogunsina et al.

(10) Patent No.: US 10,806,746 B2
(45) Date of Patent: Oct. 20, 2020

(54) DI- AND TRI-CATIONIC GLYCOSYLATED ANTITUMOR ETHER LIPIDS, L-GUCOSYLATED GAELS AND RHAMNOSE-LINKED GAELS AS CYTOTOXIC AGENTS AGAINST EPITHELIAL CANCER CELLS AND CANCER STEM CELLS

(71) Applicant: The University of Manitoba, Winnipeg (CA)

(72) Inventors: Makanjuola Ogunsina, Winnipeg (CA); Pranati Samadder, Winnipeg (CA); Frank Schweizer, Winnipeg (CA); Gilbert Arthur, Winnipeg (CA); Temilolu Idowu, Winnipeg (CA)

(*) Notice: Subject to any disclaimer, the term of this patent is extended or adjusted under 35 U.S.C. 154(b) by 110 days.

(21) Appl. No.: 15/315,163

(22) PCT Filed: May 29, 2015

(86) PCT No.: PCT/CA2015/050490
§ 371 (c)(1),
(2) Date: Nov. 30, 2016

(87) PCT Pub. No.: WO2015/179983
PCT Pub. Date: Dec. 3, 2015

(65) Prior Publication Data
US 2017/0189438 A1 Jul. 6, 2017

Related U.S. Application Data

(60) Provisional application No. 62/005,063, filed on May 30, 2014.

(51) Int. Cl.
| | |
|---|---|
| A61K 31/7028 | (2006.01) |
| A61K 31/7032 | (2006.01) |
| C07H 15/04 | (2006.01) |
| A61K 31/7056 | (2006.01) |
| A61K 31/7034 | (2006.01) |

(52) U.S. Cl.
CPC ...... A61K 31/7056 (2013.01); A61K 31/7028 (2013.01); A61K 31/7032 (2013.01); A61K 31/7034 (2013.01); C07H 15/04 (2013.01)

(58) Field of Classification Search
CPC ............ A61K 31/7056; A61K 31/7028; A61K 31/7034; C07H 15/14; C07H 15/04; C07H 7/02
USPC .............................................. 514/24, 25, 62
See application file for complete search history.

(56) References Cited

PUBLICATIONS

Samadder et al. (Anticancer Research 31: 3809-3818 (2011)).*
Eurukulla et al. (J. Med. Chem. 1996, 39, 1545-1548).*
Visvader et al. (Nature Reviews Cancer 8, 755-768 (Oct. 2008)).*
Sarkar et al. (Minerva Chir. Oct. 2009; 64(5): 489-500).*
Herman et al. (Cell Stem Cell, 1(3), 313-323, Sep. 2007).*
Rybak et al. (Biochimica et Biophysica Acta 1813 (2011) 683-694).*

* cited by examiner

*Primary Examiner* — Eric Olson
(74) *Attorney, Agent, or Firm* — Michael R. Williams; Ryan W. Dupuis; Ade & Company Inc.

(57) ABSTRACT

Glycosylated Antitumor Ether Lipids (GAELs) kill cancer cells by a nonapoptotic pathway which is an attractive strategy to avoid resistance. To further optimize the antitumor effect, we prepared various analogs of di-, and tri-cationic GAEL analogs differing in the nature of the sugar (D-glucose or L-glucose), the anomeric linkage as well as position of the glycerolipid moiety. The di- and tri-cationic GAELs were synthesized and their in vitro anticancer properties were evaluated against drug resistant and aggressively growing cancer cell lines derived from human breast, prostate, pancreatic and ovarian cancers. The most potent dicationic GAEL analogs were also studied against cancer stem cells obtained from breast BT 474, prostate DU145 and ovarian A2780cp cell lines. Our results indicate that the number of positive charges, the position of the amino substituents and the nature of the sugar have significant effects on the anticancer activities of these compounds. The most active analog kill 50% of the cells at concentration range of 0.5-5 μM and 90% of the cells at the concentration of 1-10 μM depending on type of cancer cells.

7 Claims, 22 Drawing Sheets

V'
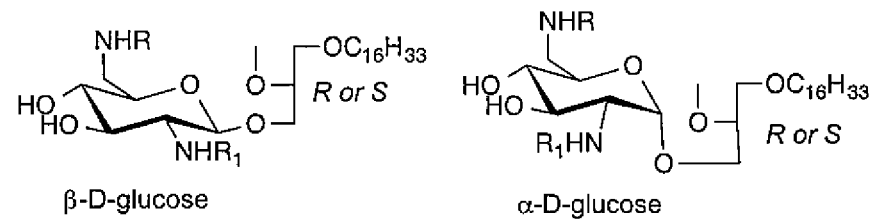
β-D-glucose        α-D-glucose
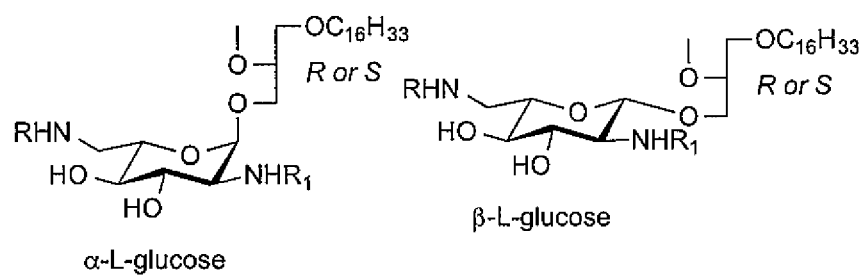
α-L-glucose        β-L-glucose
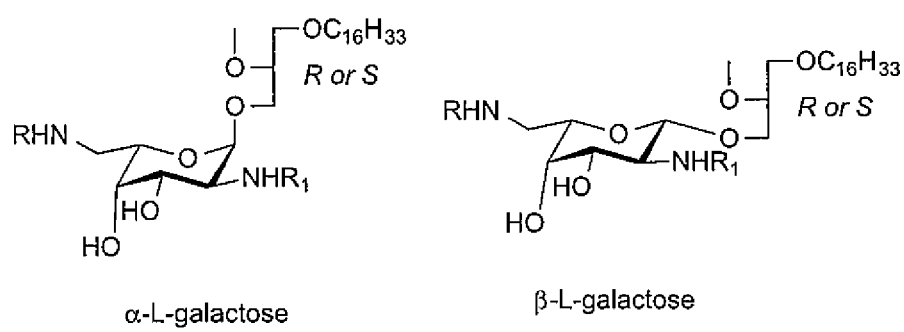
α-L-galactose      β-L-galactose
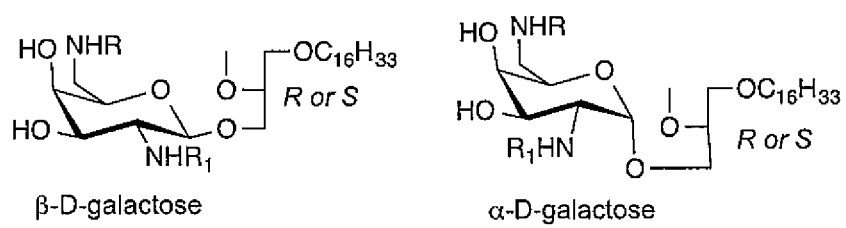
β-D-galactose      α-D-galactose
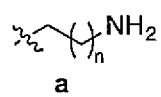 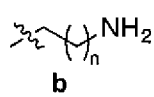   n = 1,2,3,......, 16
a            b
73. R = a; R₁ = H
74. R = b; R₁ = H
75. R = H; R₁ = a
76. R = H; R1 = b
Figure 1-4

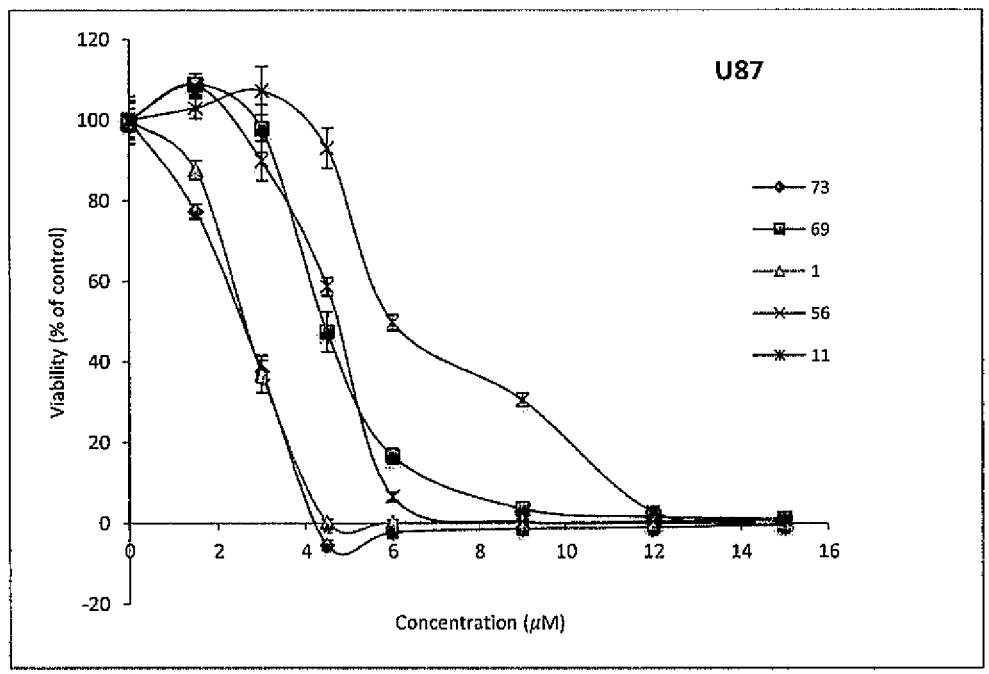
Figure 2G(i)
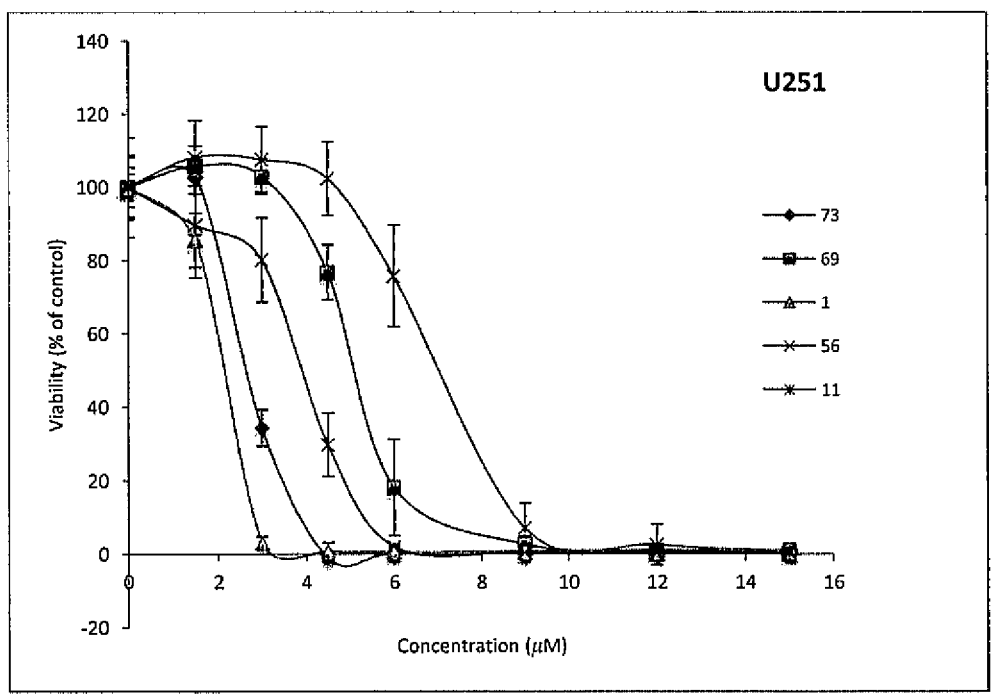
Figure 2G(ii)

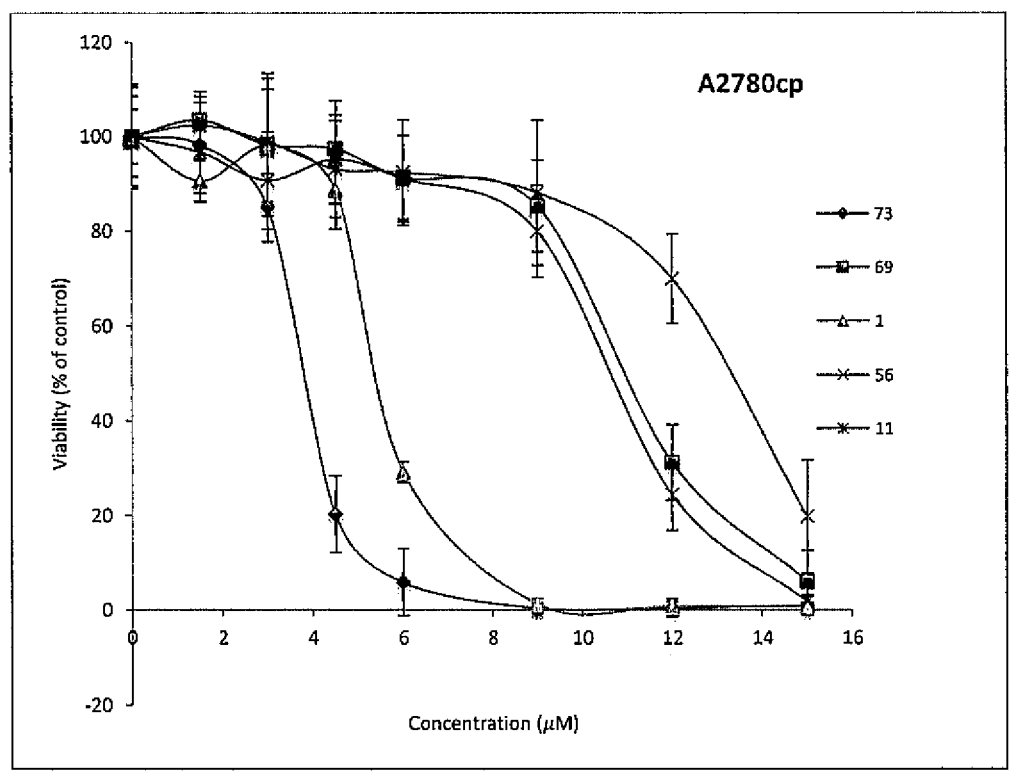
Figure 2G(iii)
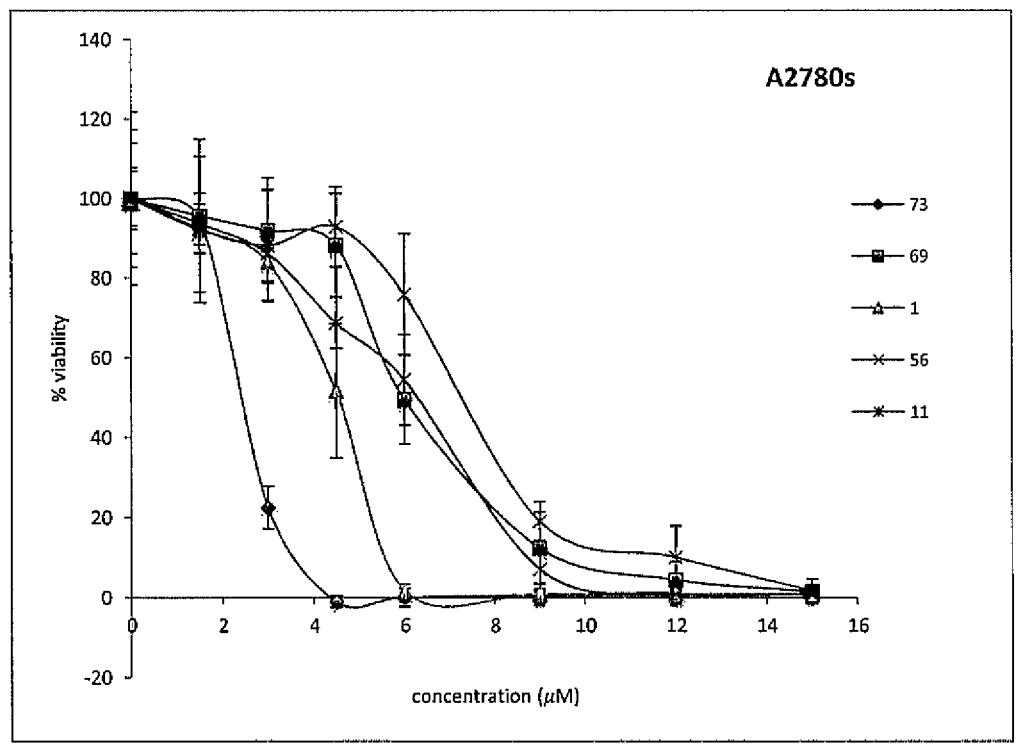
Figure 2G(iv)

DI- AND TRI-CATIONIC GLYCOSYLATED ANTITUMOR ETHER LIPIDS, L-GUCOSYLATED GAELS AND RHAMNOSE-LINKED GAELS AS CYTOTOXIC AGENTS AGAINST EPITHELIAL CANCER CELLS AND CANCER STEM CELLS

PRIOR APPLICATION INFORMATION

The instant application claims the benefit of US Provisional Patent Application, filed May 30, 2014, under Ser. No. 62/005,063, entitled Dicationic Glycosylated Antitumor Ether Lipids, L-gucosylated GAELs and Rhamnose-linked GAELs as cytotoxic agents against epithelial cancer cells and cancer stem cells', the contents of which are incorporated herein by reference.

BACKGROUND OF THE INVENTION

Despite the huge investment into finding effective treatments for cancer, it is still one of the major health problems in developed and developing countries. The UN in February 2014 estimated new cancer cases worldwide to rise from 14 million to 22 million per year within the next two decades, and annual cancer deaths rising from 8.2 million to 13 million. Cancer has therefore been described by the UN as a major obstacle to human development and well-being worldwide.

The major problems impeding the development of cures to cancer are drug resistance, radiotherapy resistance and metastases. Many of the existing anticancer drugs act by disrupting cell DNA, preventing DNA synthesis and targeting microtubules. Radiotherapy kills cells by damaging DNA. This perturbation in cell physiology induced by these drugs or radiation induces cell apoptosis to kill cancer cells. While many drugs are initially successful in killing the cancer cells, resulting in tumor shrinkage, there is invariably a relapse and the tumor reappears with cells that resist chemotherapeutic agents. (Tan, D. S. et al., *J. Natl. Cancer Inst.* 2008 100, 672-679; Tanner, M. et al., *J. Mol. Cancer Ther.* 2004, 3, 1585-1592; Ajani, J. A. et al., *Journal of Clinical Oncology* 2009, 27. 162-163). This resistance to chemotherapeutic agents results in tumors that are refractory to treatment, leading to metastases and death. There are also very few drugs, if any, for treatment of cancers that have metastasized. There is increasing evidence that the relapse of tumors and development of drug and radiation resistant tumors as well as progression to metastases may be due to the presence of a small population of cells in the tumor called cancer stem cells (CSC) or tumor initiating cells. CSCs are distinct from the cells of the bulk tumor in having the capacity for self-renewal, asymmetric division and differentiation. These cells resist apoptotic cell death induced by chemotherapy and radiotherapy, and may ultimately generate drug resistant differentiated cells that make up the bulk of tumor that recurs. CSCs have been identified and isolated from virtually all solid and haematological tumors (Garvalov, B. K. and Acker, T. *J. Mal. Med.* 2011, 89, 95-107; Zobalova, R.; Stantic, M.; Stapelberg, M.; Prokopova, K.; Dong, J.; Truksa, J. et al, Drugs that Kill Cancer Stem-like Cells. In: Shostak S, editor. Cancer Stem Cells Theories and Practice, ISBN: 978-953-307-225-8, 2011). In light of the potential role these cells play in tumor relapse, drug resistance and metastases, effective cancer treatment will require targeting the CSCs along with the bulk differentiated cells of the tumor.

Only a few compounds have been identified that kill CSCs. They include parthenolide, salinomycin, metformin, lapatinib, and mitoVES. The mechanism of cell death induction is via apoptosis, generation of reactive oxygen species and inhibition of proinflammatory cytokines NFκB. The significant toxicity of salinomycin may impact the further development of this compound which has been in use for agricultural purposes for decades (Zobalova, R.; Stantic, M.; Stapelberg, M.; Prokopova, K.; Dong, J.; Truksa, J. et al, Drugs that Kill Cancer Stem-like Cells. In: Shostak S, editor. Cancer Stem Cells Theories and Practice, ISBN: 978-953-307-225-8, 2011).

We have been working on a class of antitumor ether lipids (AEL) called glycosylated antitumor ether lipids (GAELs). The cytotoxic properties of GAELs, prototypified by compound 11, have been established to be superior to the most studied analog of AELs, edelfosine. Unlike edelfosine, which kills cells by apoptosis, GAELs kill cell by an apoptotic independent mechanism. The mechanism of action involves the perturbation of endocytosis pathway to generate large acidic vacuoles that ultimately leads to the release of acid hydrolases to induce cell death (Erukulla, R. V. et al., *J. Med. Chem.* 1996, 39, 1545-1548; Samadder, P. et al., *Biochem. Cell Biol.* 2009, 87, 401-414; Samadder, P. et al., G. *Anticancer Res.* 2011, 31, 3809-3818; Samadder, P. et al., G. *Anticancer Res.* 1998, 18, 465-470).

This ability to kill cells by an apoptosis-independent pathway led us to postulate that GAELs will have the ability to kill CSCs as they are unaffected by the apoptosis-inhibiting mechanisms or strategies the cells use to prevent death by apoptosis. Recently, we validated our hypothesis by demonstrating the cytotoxic activity of GAELs against CSCs isolated from BT474 cell lines (Samadder P. et al., *Eur J Med Chem* 2014, 78, 225-235).

Our ongoing structure activity studies on GAELs have led to the observation that the potency of anticancer activities of GAELs is intimately linked with their cationic nature. Also because the O-glycosidic bond in compounds may be susceptible to hydrolysis by glycosidases, development of non-hydrolysable analogs will enhance the stability of the compounds in vivo.

SUMMARY OF THE INVENTION

According to an aspect of the invention, there is provided a method of treating cancer in an individual in need of such treatment comprising administering to said individual an effective amount of a compound of formula (I), formula (I'), formula (II), formula (II'), formula (III), formula (III'), formula (IV), formula (IV'), formula (V) or formula (V'), as set forth below.

According to another aspect of the invention, there is provided use of a compound of formula (I), formula (I'), formula (II), formula (II'), formula (III), formula (III') formula (IV), formula (IV'), formula (V) or formula (V') as described herein for treating cancer According to yet another aspect of the invention, there is provided use of a compound of formula (I), formula (I'), formula (II), formula (II'), formula (III), formula (III'), formula (IV), formula (IV'), formula (V) or formula (V') in the manufacture of a medicament for treating cancer.

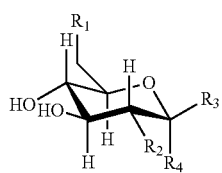
1. $R_1 = NH_2, R_2 = NH_2, R_3 = H, R_4 = a$
2. $R_1 = NH_2, R_2 = NH_2, R_3 = a, R_4 = H$
3. $R_1 = NH_2, R_2 = b, R_3 = a, R_4 = H$
4. $R_1 = NH_2, R_2 = NH_2, R_3 = c, R_4 = H$
5. $R_1 = NH_2, R_2 = NH_2, R_3 = d, R_4 = H$
6. $R_1 = NH_2, R_2 = NH_2, R_3 = e, R_4 = H$
7. $R_1 = NH_2, R_2 = NH_2, R_3 = f, R_4 = H$
8. $R_1 = NH_2, R_2 = NH_2, R_3 = g, R_4 = H$
9. $R_1 = NH_2, R_2 = NH_2, R_3 = h, R_4 = H$
10. $R_1 = NH_2, R_2 = NH_2, R_3 = i, R_4 = H$
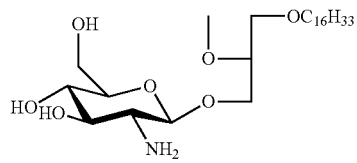
11
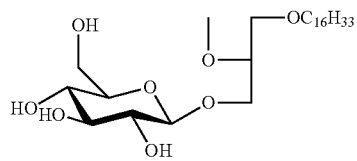
12
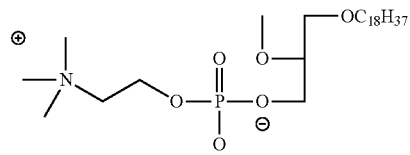
13
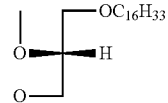
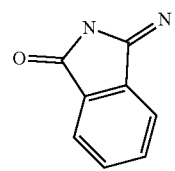
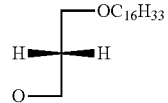
a     b     c
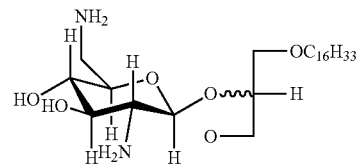
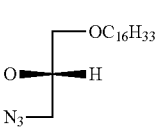
d     e
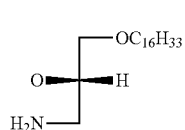
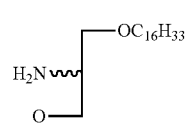
f     g
-continued
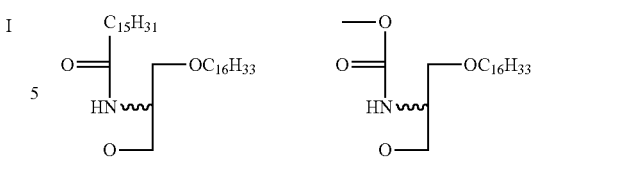
h     i
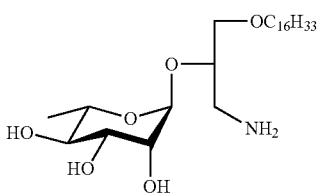
56
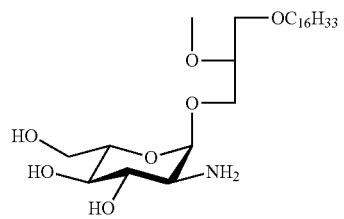
69
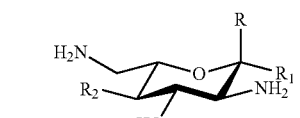
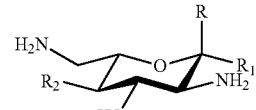
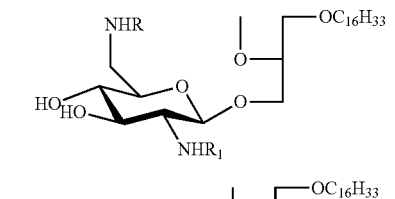
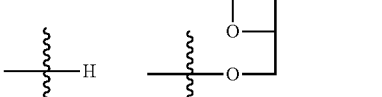
a     b
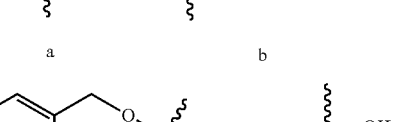
c     d
70. $R = a, R_1 = b, R_2 = c$
71. $R = b, R_1 = a, R_2 = d$
72. $R = b, R_1 = a, R_2 = c$

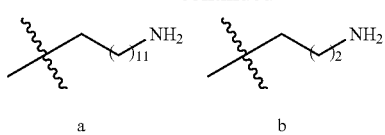

73. R = a; R₁ = H
74. R = b; R₁ = H
75. R = H; R₁ = a
76. R = H; R1 = b

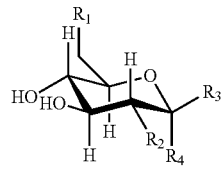

D-glucose

1. $R_1 = NH_2, R_2 = NH_2, R_3 = H, R_4 = a$
2. $R_1 = NH_2, R_2 = NH_2, R_3 = a, R_4 = H$
3. $R_1 = NH_2, R_2 = b, R_3 = a, R_4 = H$
4. $R_1 = NH_2, R_2 = NH_2, R_3 = c, R_4 = H$
5. $R_1 = NH_2, R_2 = NH_2, R_3 = d, R_4 = H$
6. $R_1 = NH_2, R_2 = NH_2, R_3 = e, R_4 = H$
7. $R_1 = NH_2, R_2 = NH_2, R_3 = f, R_4 = H$
8. $R_1 = NH_2, R_2 = NH_2, R_3 = g, R_4 = H$
9. $R_1 = NH_2, R_2 = NH_2, R_3 = h, R_4 = H$
10. $R_1 = NH_2, R_2 = NH_2, R_3 = i, R_4 = H$

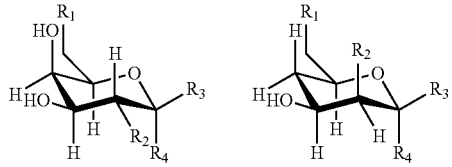

D-galactose   D-mannose

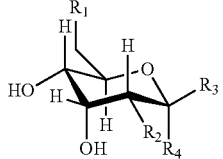

D-allose   L-glucose

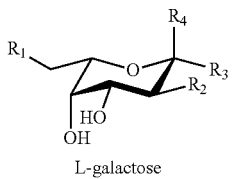

L-galactose

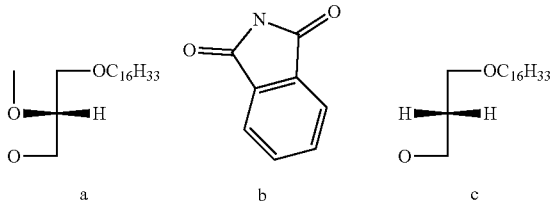

a   b   c

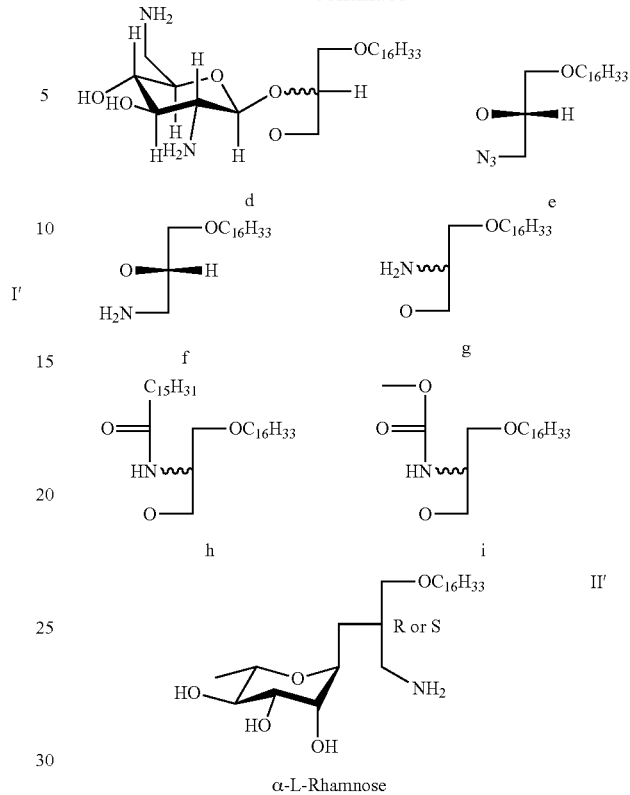

d   e
f   g
h   i

α-L-Rhamnose
56

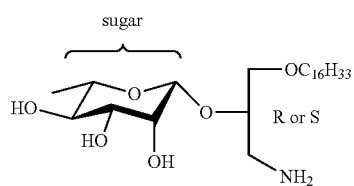

β-L-Rhamnose sugar = 6-deoxy-α-D-galactose, 6-deoxy-β-D-galactose, 6-deoxy-α-L-galactose, 6-deoxy-β-L-galactose, 6-deoxy-α-D-glucose, 6-deoxy-β-D-glucose, 6-deoxy-α-L-glucose-based, 6-deoxy-β-L-glucose, 6-deoxy-α-D-mannose, 6-deoxy-β-D-mannose, 6-deoxy-α-L-mannose, or 6-deoxy-β-L-mannose

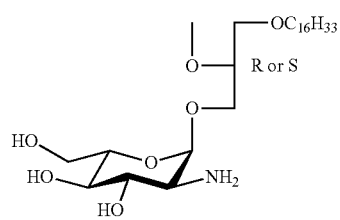

α-L-glucose
69

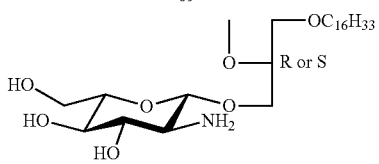

β-L-glucose

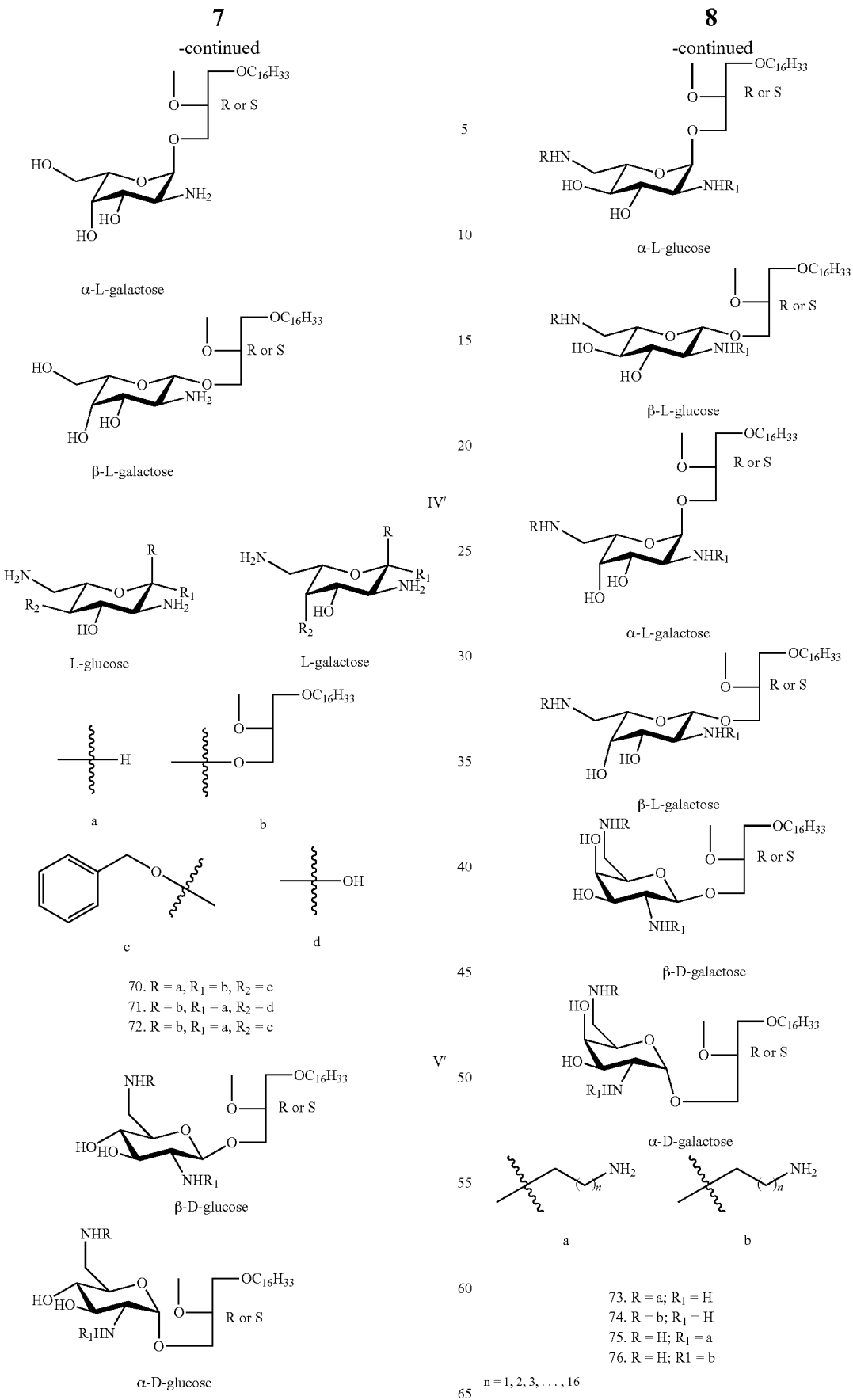

The absorbance was read at 490 nm in a plate reader. The results are the means±standard deviation for 4 independent determinations.

Figure 3A:
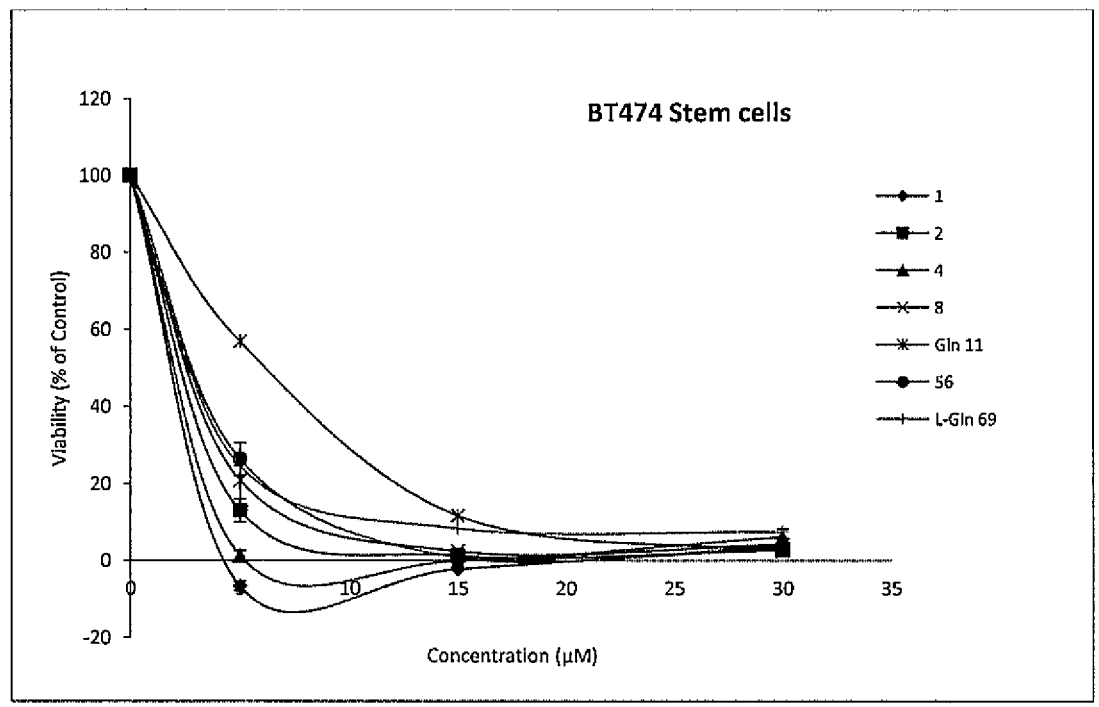
FIG. 3A. Effects of compounds 1, 2, 4, 8, 56 and 69 on the viability of cancer stems cells isolated form BT-474 breast cancer cell lines. BT474 cancer stem cells were obtained by staining for ALDH1 and sorting the cells by flow cytometry. The spheroids were grown in ultra low adhesion plates in mammocult medium for 6 days. The spheroids formed were harvested and trypsinised and equal numbers were seeded in 48-well low adhesion plates for 5-6 days to allow formation of spheroids. The spheroids were incubated with varying concentrations of compounds 1, 2, 4 or 8 (0-30 µM) for 6 days. At the end of the incubation the MTS reagent was added to each well and the plates were incubated in a 5% $CO_2$ incubator for 4 h. The absorbance was read at 490 nm in a plate reader. The results are the means±standard deviation for 4 independent determinations.
Figure 3B:
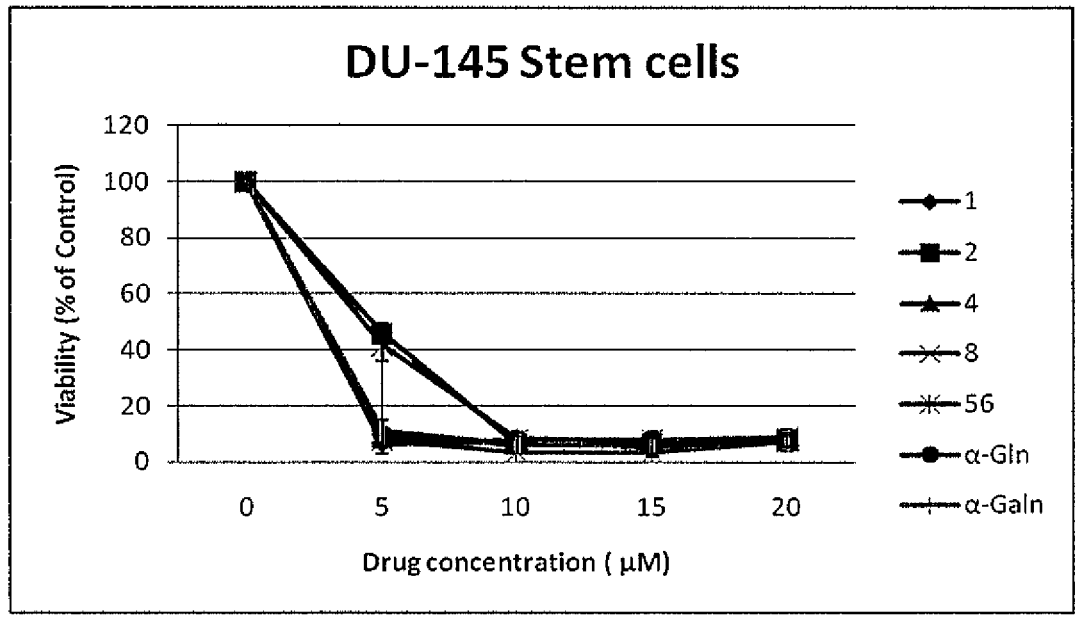
FIG. 3B. Effects of compounds 1, 2, 4, 8 and 56 on the viability of cancer stems cells isolated form DU145 prostate cancer cell lines. DU145 cancer stem cells were obtained by staining for ALDH1 and sorting the cells by flow cytometry. The spheroids were grown in ultra low adhesion plates in prostatosphere growth medium for 6 days. The spheroids formed were harvested and trypsinised and equal numbers were seeded in 48-well low adhesion plates for 5-6 days to allow formation of spheroids. The spheroids were incubated with varying concentrations of compounds 1, 2, 4, 8 or 56 (0-30 µM) for 6 days. At the end of the incubation the MTS reagent was added to each well and the plates were incubated in a 5% $CO_2$ incubator for 4 h.
Figure 3C:
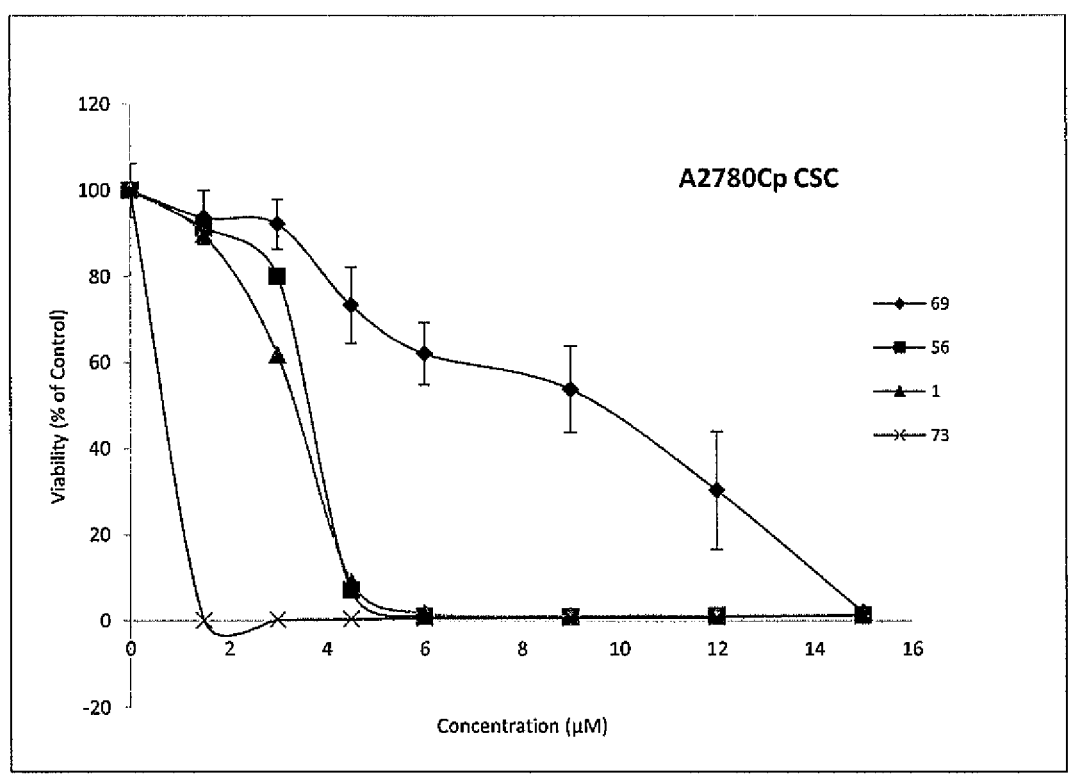

FIG. 3C. Effect of 1, 56, 69 or 73 on viability of cancer stem cells isolated from A2780cp ovarian cancer cell line. A2780 cancer stem cells were obtained by staining A2780cp cells for ALDH1 and sorting the cells by flow cytometry. The spheroids/aggregates were grown in ultra low adhesion plates in TPM medium for 6 days. The spheroids formed were harvested and trypsinised and equal numbers were seeded in 48-well low adhesion plates for 3 days followed by incubation with varying concentrations of compounds 1, 56, 69 or 73 for 3 days. At the end of the incubation the MTS reagent was added to each well and the plates were incubated in a 5% $CO_2$ incubator for 4 h. The absorbance was read at 490 nm in a plate reader. The results are the means±standard deviation for 4 independent determinations.

Figure 4A:
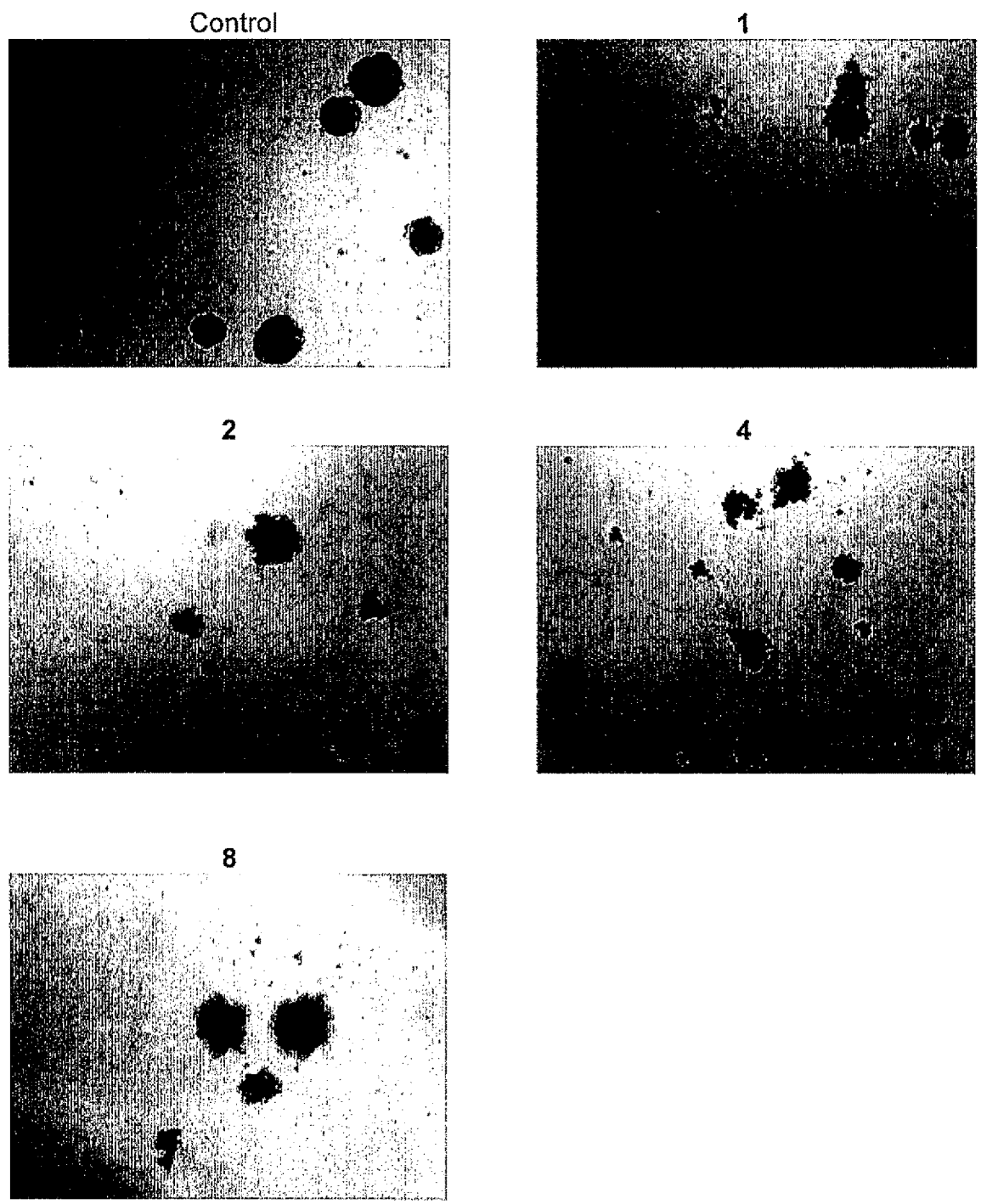

FIG. 4A. Effect of GAEL compounds 1, 2, 4, and 8 on the integrity of BT474 breast cancer stem cell spheroids. Equal numbers of BT474 cancer stem cells were seeded into ultra low adhesion 48-well plates and grown for 5 days to allow for spheroid formation. The spheroids were incubated with or without 10 µM GAELs for up to 6 days. The images were taken after 4 days of incubation with an Olympus IX70 microscope at a magnification of ×10.

Figure 4B:
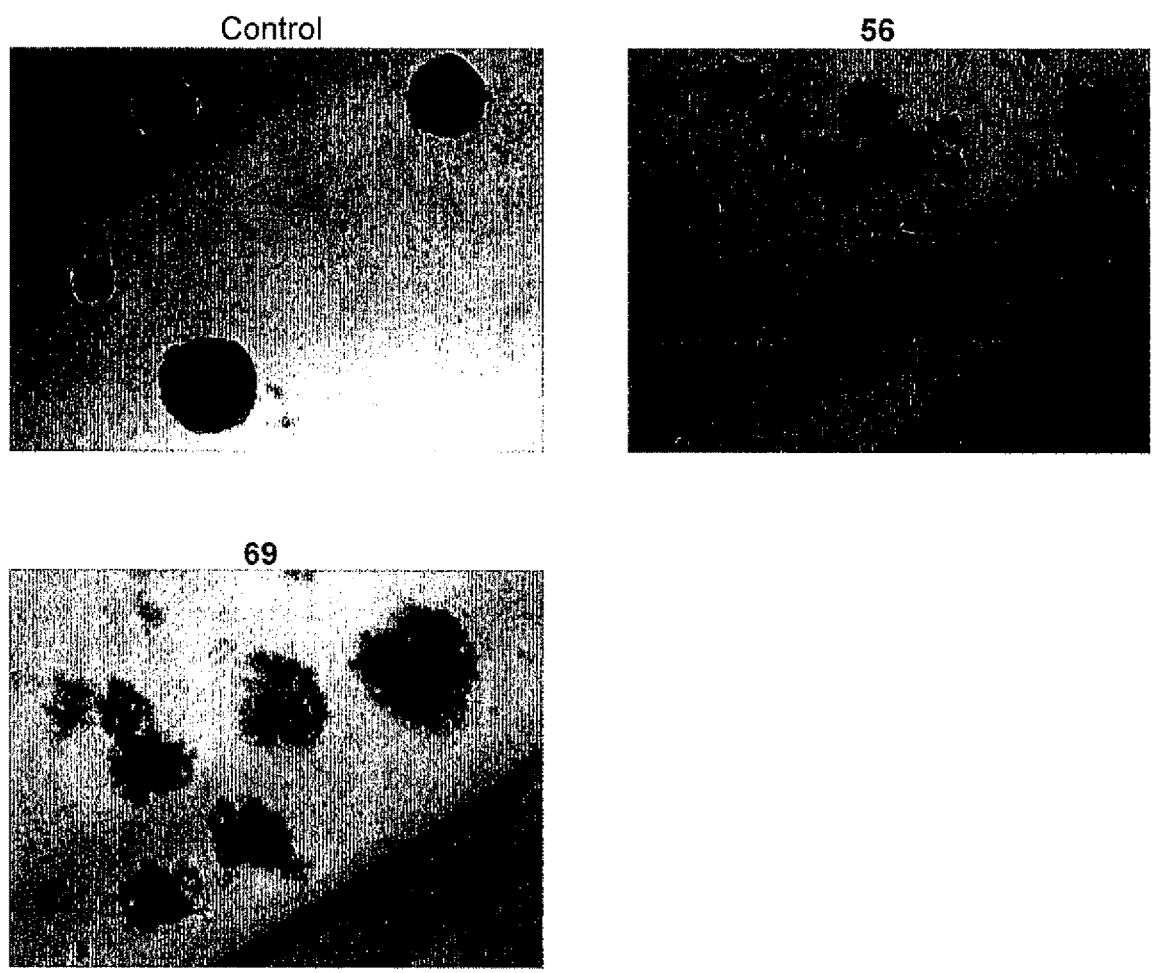

FIG. 4B. Effect of GAEL compounds 56 and 69 on the integrity of BT474 breast cancer stem cell spheroids. Equal numbers of BT474 cancer stem cells were seeded into ultra low adhesion 48-well plates and grown for 5 days to allow for spheroid formation. The spheroids were incubated with or without 10 µM GAELs for up to 6 days. The images were taken after 4 days of incubation with an Olympus IX70 microscope at a magnification of ×10.

Figure 4C:
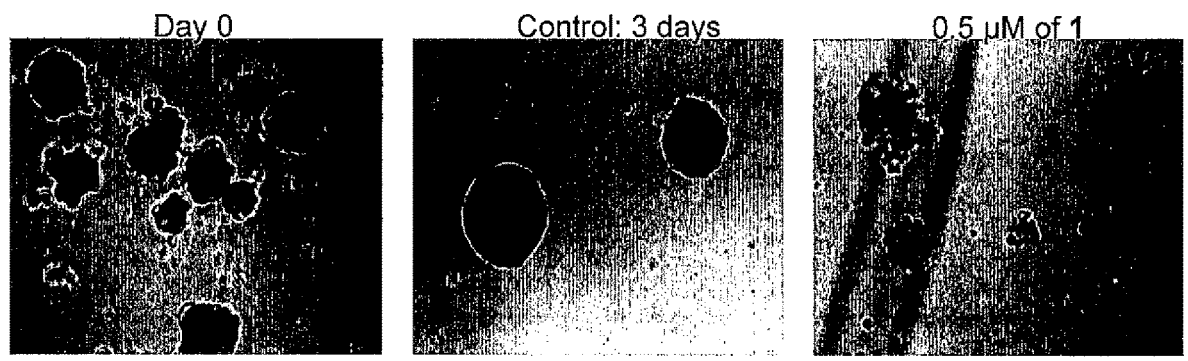

FIG. 4C. Effect of GAEL compound 1 on the integrity of EOC 258 ovarian cancer cell spheroids. Equal numbers of EOC 258 cells were seeded into ultra low adhesion 96-well plates and grown for 3 days to allow for spheroid formation. The spheroids were incubated with or without 1 (0-10 µM) for 3 days. The images were taken with an Olympus IX70 microscope at a magnification of ×10.

Figure 5A:
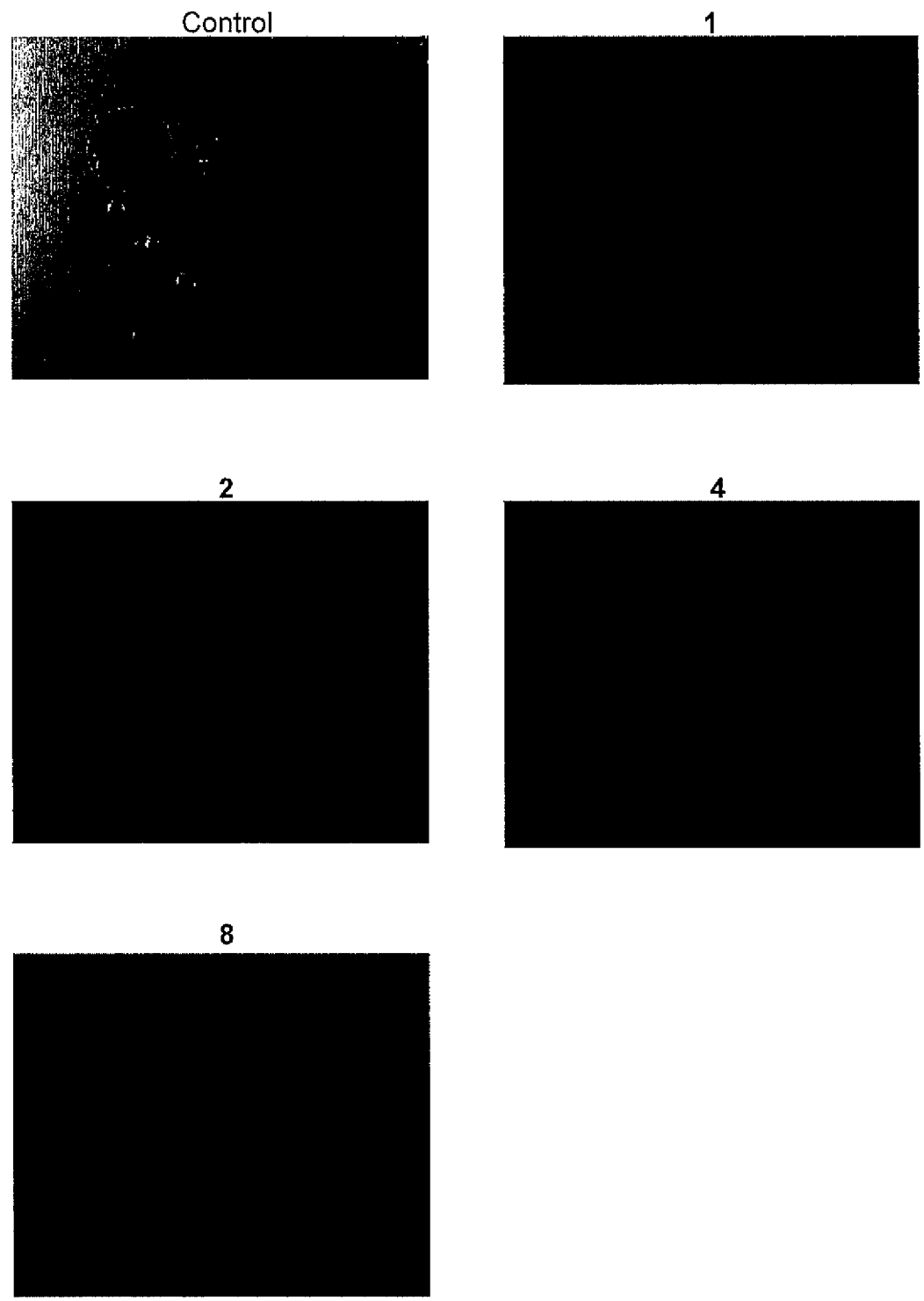

FIG. 5A. Effect of GAEL compounds 1, 2, 4, and 8 on the integrity of DU145 prostate cancer stem cell spheroids. Equal numbers of DU145 cancer stem cells were seeded into ultra low adhesion 48-well plates and grown for 5 days to allow for spheroid formation. The spheroids were incubated with or without 10 µM GAELs for up to 6 days. The images were taken after 4 days of incubation with an Olympus IX70 microscope at a magnification of ×10.

Figure 5B:
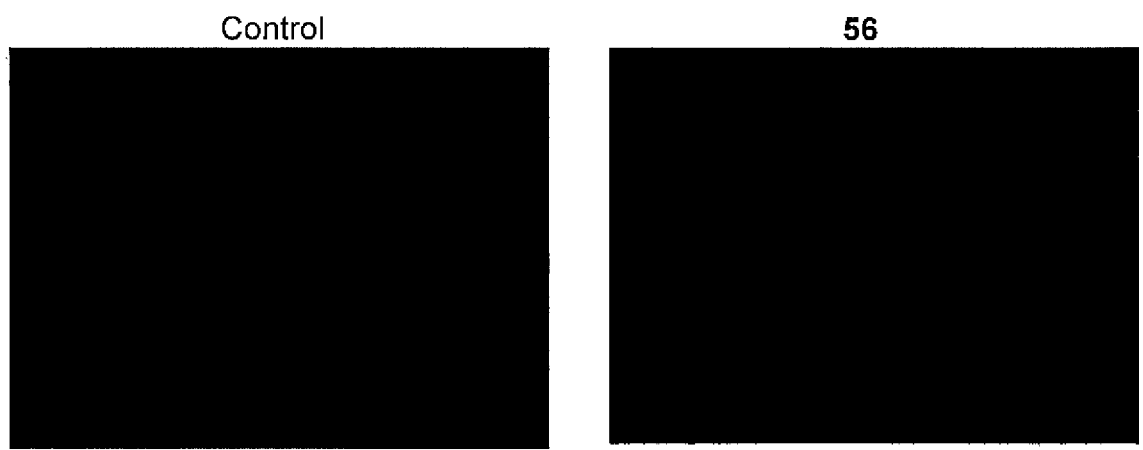

FIG. 5B. Effect of GAEL compound 56 on the integrity of DU145 prostate cancer stem cell spheroids. Equal numbers of DU145 cancer stem cells were seeded into ultra low adhesion 48-well plates and grown for 5 days to allow for spheroid formation. The spheroids were incubated with or without 10 µM GAELs for up to 6 days. The images were taken after 4 days of incubation with an Olympus IX70 microscope at a magnification of ×10.

Figure 5C:
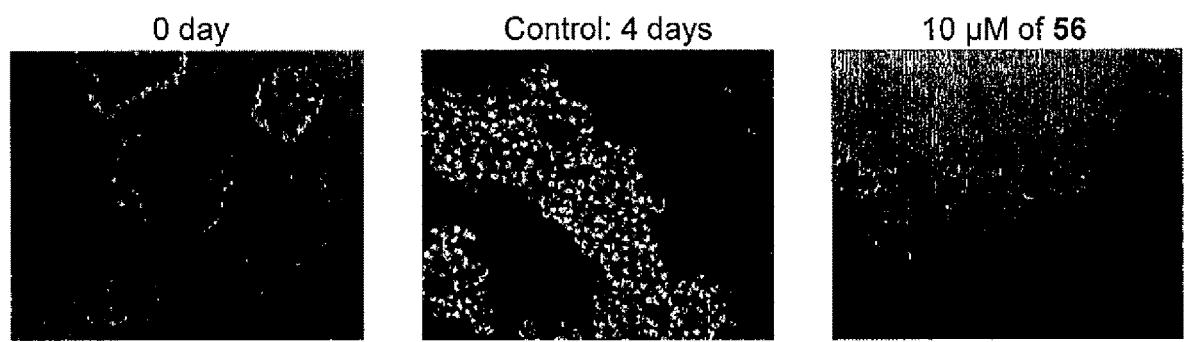

FIG. 5C. Effect of GAEL compound 56 on the integrity of A2780 ovarian cancer stem cells. Equal numbers of A2780 cancer stem cells were seeded into ultra low adhesion 48-well plates and grown for 4 days to allow for spheroid/aggregate formation. The spheroids were incubated with or without 10 µM GAELs for up to 6 days. The images were taken after 4 days of incubation with an Olympus IX70 microscope at a magnification of ×10

Figure 6:
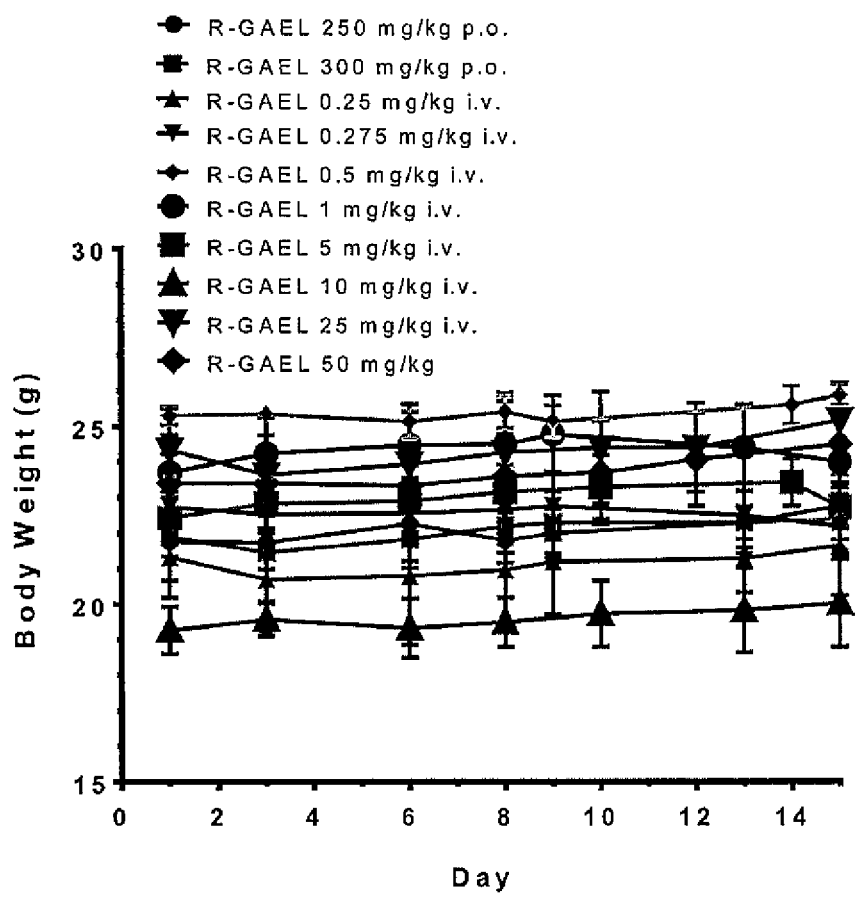

FIG. 6. Tolerability of female Rag2M mice to compound 56. Female Rag2 mice were individually weighed and administered compound 56 intravenously or orally according to individual body weight. The mice were monitored for behavioural changes, body weight for 14 days. All mice were sacrificed on day 15 and necropsy was performed to compound 56. The figure shows the body weight of the mice following treatment for 14 days. The weights are the average of 3 mice.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Glycosylated Antitumor Ether Lipids (GAELs) kill cancer cells by a non-apoptotic pathway, which is an attractive strategy to avoid resistance. To further optimize the antitumor effect, we prepared various analogs of dicationic GAEL analogs, differing in the nature of the sugar, the anomeric linkage as well as position of the glycerolipid moiety. As discussed below, fifteen dicationic GAELs and four tricationic GAELs were synthesized and their in vitro anticancer properties were evaluated against drug resistant and aggressively growing cancer cell lines derived from human breast, prostate and pancreatic cancers. The most potent dicationic and tricationic GAEL analogs were also studied against cancer stem cells obtained from breast BT474 cell line and prostate DU 145 cells and A2780cp. The anticancer activities of the dicationic GAELs were compared to their monocationic analogs which have previously been studied in our group. Our results indicate that the number of positive charges, the position of the amino substituents and the nature of the sugar have significant effects on the anticancer activities of these compounds. The most active analogs kill 50% of the cells at concentration range of 0.5-5 µM and 90% of the cells at the concentration of 1-7 µM, depending on type of cancer cells, as discussed below. Replacement of the sugar with L-glucosamine showed activity comparable with analogs with D-glucosamine. The mono cationic L-rhamnose derived analog has $CC_{50}$ and $CC_{90}$ values in the range of 2-11 µM and 6.5 to 14 µM respectively against the cell lines tested. Our results also show that primary ovarian cancer cells derived from the ascites of ovarian cancer patients are particularly susceptible to GAELs with $CC_{50}$'s in the nM to low µM range. The sensitivity of these cells to GAELs were observed whether the cells were grown as adherent (2D) cultures or as spheroidal (3D) cultures In one embodiment of the invention, there is provided a method of treating cancer in an individual in need of such treatment comprising administering to said individual an effective amount of a compound of formula (I), formula (I'), formula (II), formula (II'), formula (III), formula (III'), formula (IV), formula (IV'), formula (V) or formula (V')

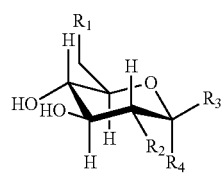

1. $R_1 = NH_2, R_2 = NH_2, R_3 = H, R_4 = a$
2. $R_1 = NH_2, R_2 = NH_2, R_3 = a, R_4 = H$
3. $R_1 = NH_2, R_2 = b, R_3 = a, R_4 = H$
4. $R_1 = NH_2, R_2 = NH_2, R_3 = c, R_4 = H$
5. $R_1 = NH_2, R_2 = NH_2, R_3 = d, R_4 = H$
6. $R_1 = NH_2, R_2 = NH_2, R_3 = e, R_4 = H$
7. $R_1 = NH_2, R_2 = NH_2, R_3 = f, R_4 = H$
8. $R_1 = NH_2, R_2 = NH_2, R_3 = g, R_4 = H$
9. $R_1 = NH_2, R_2 = NH_2, R_3 = h, R_4 = H$
10. $R_1 = NH_2, R_2 = NH_2, R_3 = i, R_4 = H$

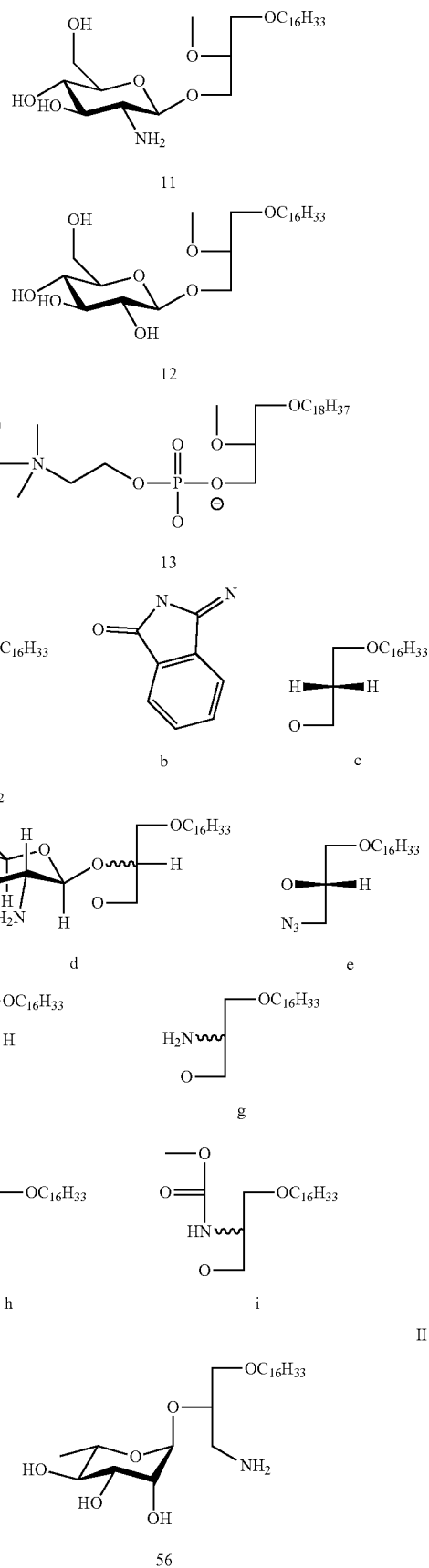

15
-continued

69

70. R = a, R₁ = b, R₂ = c
71. R = b, R₁ = a, R₂ = d
72. R = b, R₁ = a, R₂ = c

73. R = a; R₁ = H
74. R = b; R₁ = H
75. R = H; R₁ = a
76. R = H; R1 = b

16
-continued

III

D-glucose

1. $R_1 = NH_2, R_2 = NH_2, R_3 = H, R_4 = a$
2. $R_1 = NH_2, R_2 = NH_2, R_3 = a, R_4 = H$
3. $R_1 = NH_2, R_2 = b, R_3 = a, R_4 = H$
4. $R_1 = NH_2, R_2 = NH_2, R_3 = c, R_4 = H$
5. $R_1 = NH_2, R_2 = NH_2, R_3 = d, R_4 = H$
6. $R_1 = NH_2, R_2 = NH_2, R_3 = e, R_4 = H$
7. $R_1 = NH_2, R_2 = NH_2, R_3 = f, R_4 = H$
8. $R_1 = NH_2, R_2 = NH_2, R_3 = g, R_4 = H$
9. $R_1 = NH_2, R_2 = NH_2, R_3 = h, R_4 = H$
10. $R_1 = NH_2, R_2 = NH_2, R_3 = i, R_4 = H$

IV

D-galactose          D-mannose

V

D-allose             L-glucose

L-galactose

-continued

II'

α-L-Rhamnose
56 sugar = 6-deoxy-α-D-galactose, 6-deoxy-β-D-galactose, 6-deoxy-α-L-galactose, 6-deoxy-β-L-galactose, 6-deoxy-α-D-glucose, 6-deoxy-β-D-glucose, 6-deoxy-α-L-glucose-based, 6-deoxy-β-L-glucose, 6-deoxy-α-D-mannose, 6-deoxy-β-D-mannose, 6-deoxy-α-L-mannose, or 6-deoxy-β-L-mannose β-L-Rhamnose

III'

α-L-glucose
69

β-L-glucose

α-L-galactose

-continued

β-L-galactose

IV'

L-glucose        L-galactose a         b c         d

70. R = a, R₁ = b, R₂ = c
71. R = b, R₁ = a, R₂ = d
72. R = b, R₁ = a, R₂ = c

V'

β-D-glucose

α-D-glucose

α-L-glucose

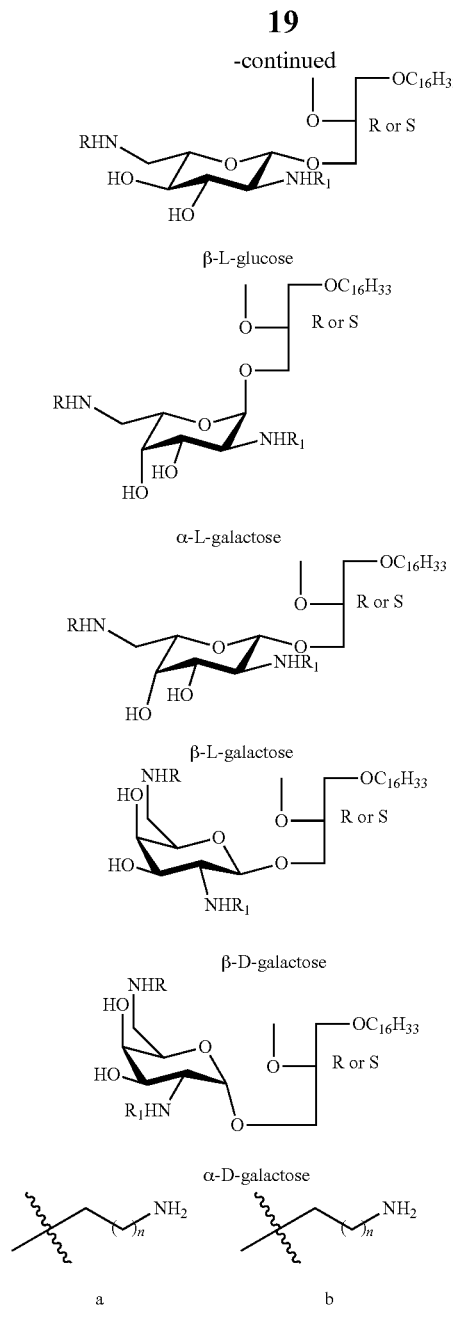

73. R = a; R₁ = H
74. R = b; R₁ = H
75. R = H; R₁ = a
76. R = H; R1 = b n = 1, 2, 3, . . . , 16

In another embodiment of the invention, the compound is selected from the group consisting of: 1-O-Hexadecyl-2-O-methyl-3-O-(2',6'-diamino-2',6'-dideoxy-α-D-glucopyranosyl)-sn-glycerol; 1-O-Hexadecyl-2-O-methyl-3-O-(2',6'-diamino-2',6'-dideoxy-β-D-glucopyranosyl)-sn-glycerol; 1-O-Hexadecyl-2-deoxy-3-O-(2',6'-diamino-2',6'-dideoxy-β-D-glucopyranosyl)-sn-glycerol; 1-O-Hexadecyloxy-2S/R-amino-3-(-2'-amino-2'-deoxy-β-D-glucopyranosyl)-glycerol; 1-O-Hexadecyloxy-2R-(-α-L-rhamnopyranosyl)-3-amino glycerol; 1-O-Hexadecyloxy-2R—O-methyl-(2'amino-2'deoxy-α-L-glucopyranosyl)-3-amino glycerol; 1-O-Hexadecyl-2-O-methyl-3-O-(4'-benzyl-2',6'-diamino-2',6'-dideoxy-β-L-glucopyranosyl)-sn-glycerol; 1-O-Hexadecyl-2-O-methyl-3-O-(2',6'-diamino-2',6'-dideoxy-α-L-glucopyranosyl)-sn-glycerol; 1-O-Hexadecyl-2-O-methyl-3-O-(4'-benzyl-2',6'-diamino-2',6'-dideoxy-α-L-glucopyranosyl)-sn-glycerol; 1-O-Hexadecyl-2-O-methyl-3-O-[6'-N-(12-aminododecyl)-2',6'-diamino-2',6'-dideoxy-glucopyranoside]-sn-glycerol; 1-O-Hexadecyl-2-O-methyl-3-O-[6'-N-(3-aminopropyl)-2',6'-diamino-2',6'-dideoxy-glucopyranoside]-sn-glycerol; 1-O-Hexadecyl-2-O-methyl-3-O-[2'-N-(12-aminododecyl)-2',6'-diamino-2',6'-dideoxy-glucopyranoside]-sn-glycerol and 1-O-Hexadecyl-2-O-methyl-3-O-methyl-3-O-[2'-N-(3-aminopropyl)-2',6'-diamino-2',6'-dideoxy-glucopyranoside]-sn-glycerol.

As will be appreciated by one of skill in the art, the compounds of formula (I) are D-glucose based. In alternative embodiments, the compounds may be D-galactose-based, D-mannose-based, D-allose, L-glucose or L-galactose-based as shown in formula (I'). The stereochemistry of the glycerolipid may be R or S as shown in formula (I').

Similarly, the compound of formula (II) is α-L-rhamnose based but in alternative embodiments may be α-L-rhamnose, 6-deoxy-α-D-galactose, 6-deoxy-β-D-galactose 6-deoxy-α-L-galactose, 6-deoxy-β-L-galactose, 6-deoxy-α-D-glucose, 6-deoxy-β-D-glucose, 6-deoxy-α-L-glucose-based, 6-deoxy-β-L-glucose-based, 6-deoxy-α-D-mannose, 6-deoxy-β-D-mannose, 6-deoxy-α-L-mannose-based or 6-deoxy-β-L-mannose-based. The stereochemistry of the glycerolipid may be R or S as shown in formula (II')

The compound of formula (III) is α-L-glucose based but in other embodiments may be β-L-glucose, α-L-galactose or β-L-galactose-based as shown in formula (III') The stereochemistry of the glycerolipid may be R or S.

In yet other embodiments, where appropriate, O-glycoside may be replaced with C-glycoside.

The compound of formula (IV) are α-L-gluco-based diamino glycolipids or β-L-gluco diamino glycolipids that can contain one or more benzylether groups at the sugar portion but in alternative embodiments may be β-L-galacto or α-L-galacto-based as shown in formula (IV'). The stereochemistry of the glycerolipid may be R or S.

The compounds of formula (V) are tricationic β-D-gluco-based glycolipids with alkylamino substituents at the 2- or 6-position of D-glucose but in alternative embodiments may be α-D-gluco-based, α-L-gluco-based, β-L-gluco-based, α-D-galacto-based, β-D-galacto-based, α-L-galacto-based or β-L-galacto-based as shown in formula (V'). The stereochemistry of the glycerolipid may be R or S.

As will be apparent to one of skill in the art, other suitable substitutions and alterations can be determined through routine experimentation, based on the guidance on the relationship between structure and activity of the compounds provided herein.

According to another aspect of the invention, there is provided a compound of formula (I), formula (II), formula (III), formula (IV) or formula (V).

In a preferred embodiment of the invention, the compound is selected from the group consisting of: 1-O-Hexadecyl-2-O-methyl-3-O-(2',6'-diamino-2',6'-dideoxy-α-D-glucopyranosyl)-sn-glycerol; 1-O-Hexadecyl-2-O-methyl-3-O-(2',6'-diamino-2',6'-dideoxy-β-D-glucopyranosyl)-sn-glycerol; 1-O-Hexadecyl-2-deoxy-3-O-(2'6'-diamino-2',6'-dideoxy-β-D-glucopyranosyl)-sn-glycerol; 1-O-Hexadecyloxy-2S/R-amino-3-(-2'-amino-2'-deoxy-β-D-glucopyranosyl)-glycerol; 1-O-Hexadecyloxy-2R-(-α-L-rhamnopyranosyl)-3-amino glycerol; 1-O-Hexadecyloxy- 2R—O-methyl-(2'amino-2'deoxy-α-L-glucopyranosyl)-3-amino glycerol; 1-O-Hexadecyl-2-O-methyl-3-O-(4'-benzyl-2',6'-diamino-2',6'-dideoxy-β-L-glucopyranosyl)-sn-glycerol; 1-O-Hexadecyl-2-O-methyl-3-O-(2',6'-diamino-2',6'-dideoxy-α-L-glucopyranosyl)-sn-glycerol; 1-O-Hexadecyl-2-O-methyl-3-O-(4'-benzyl-2',6'-diamino-2',6'-dideoxy-α-L-glucopyranosyl)-sn-glycerol; 1-O-Hexadecyl-2-O-methyl-3-O-methyl-3-O-[6'-N-(12-aminododecyl)-2',6'-diamino-2',6'-dideoxy-glucopyranoside]-sn-glycerol; 1-O-Hexadecyl-2-O-methyl-3-O-[6'-N-(3-aminopropyl)-2',6'-diamino-2',6'-dideoxy-glucopyranoside]-sn-glycerol; 1-O-Hexadecyl-2-O-methyl-3-O-[2'-N-(12-aminododecyl)-2',6'-diamino-2',6'-dideoxy-glucopyranoside]-sn-glycerol and 1-O-Hexadecyl-2-O-methyl-3-O-[2'-N-(3-aminopropyl)-2',6'-diamino-2',6'-dideoxy-glucopyranoside]-sn-glycerol.

According to another aspect of the invention, there is provided use of a compound of formula (I), formula (I'), formula (II), formula (II'), formula (III), formula (III'), formula (IV), formula (IV'), formula (V) or formula (V') for treating cancer.

In a preferred embodiment of the invention, the compound is selected from the group consisting of: In another embodiment of the invention, the compound is selected from the group consisting of: 1-O-Hexadecyl-2-O-methyl-3-O-(2',6'-diamino-2',6'-dideoxy-α-D-glucopyranosyl)-sn-glycerol; 1-O-Hexadecyl-2-O-methyl-3-O-(2',6'-diamino-2',6'-dideoxy-β-D-glucopyranosyl)-sn-glycero; 1-O-Hexadecyl-2-deoxy-3-O-(2'6'-diamino-2',6'-dideoxy-β-D-glucopyranosyl)-sn-glycerol; 1-O-Hexadecyloxy-2S/R-amino-3-(-2'-amino-2'-deoxy-β-D-glucopyranosyl)-glycerol; 1-O-Hexadecyloxy-2R-(-α-L-rhamnopyranosyl)-3-amino glycerol; 1-O-Hexadecyloxy-2R—O-methyl-(2'amino-2'deoxy-α-L-glucopyranosyl)-3-amino glycerol; 1-O-Hexadecyl-2-O-methyl-3-O-(4'-benzyl-2',6'-diamino-2',6'-dideoxy-β-L-glucopyranosyl)-sn-glycerol; 1-O-Hexadecyl-2-O-methyl-3-O-(2',6'-diamino-2',6'-dideoxy-α-L-glucopyranosyl)-sn-glycerol; 1-O-Hexadecyl-2-O-methyl-3-O-(4'-benzyl-2',6'-diamino-2',6'-dideoxy-α-L-glucopyranosyl)-sn-glycerol; 1-O-Hexadecyl-2-O-methyl-3-O-[6'-N-(12-aminododecyl)-2',6'-diamino-2',6'-dideoxy-glucopyranoside]-sn-glycerol; 1-O-Hexadecyl-2-O-methyl-3-O-[6'-N-(3-aminopropyl)-2',6'-diamino-2',6'-dideoxy-glucopyranoside]-sn-glycerol; 1-O-Hexadecyl-2-O-methyl-3-O-[2'-N-(12-aminododecyl)-2',6'-diamino-2',6'-dideoxy-glucopyranoside]-sn-glycerol and 1-O-Hexadecyl-2-O-methyl-3-O-[2'-N-(3-aminopropyl)-2',6'-diamino-2',6'-dideoxy-glucopyranoside]-sn-glycerol.

According to another aspect of the invention, there is provided use of a compound of formula (I), formula (I'), formula (II), formula (II'), formula (III), formula (III'), formula (IV), formula (IV'), formula (V) or formula (V') in the manufacture of a medicament for treating cancer.

In a preferred embodiment of the invention, the compound is selected from the group consisting of: 1-O-Hexadecyl-2-O-methyl-3-O-(2',6'-diamino-2',6'-dideoxy-α-D-glucopyranosyl)-sn-glycerol; 1-O-Hexadecyl-2-O-methyl-3-O-(2',6'-diamino-2',6'-dideoxy-β-D-glucopyranosyl)-sn-glycerol; 1-O-Hexadecyl-2-deoxy-3-O-(2'6'-diamino-2',6'-dideoxy-β-D-glucopyranosyl)-sn-glycerol; 1-O-Hexadecyloxy-2S/R-amino-3-(-2'-amino-2'-deoxy-β-D-glucopyranosyl)-glycerol; 1-O-Hexadecyloxy-2R-(-α-L-rhamnopyranosyl)-3-amino glycerol; 1-O-Hexadecyloxy-2R—O-methyl-(2'amino-2'deoxy-α-L-glucopyranosyl)-3-amino glycerol; 1-O-Hexadecyl-2-O-methyl-3-O-(4'-benzyl-2',6'-diamino-2',6'-dideoxy-β-L-glucopyranosyl)-sn-glycerol; 1-O-Hexadecyl-2-O-methyl-3-O-(2',6'-diamino-2',6'-dideoxy-α-L-glucopyranosyl)-sn-glycerol; 1-O-Hexadecyl-2-O-methyl-3-O-(4'-benzyl-2',6'-diamino-2',6'-dideoxy-α-L-glucopyranosyl)-sn-glycerol; 1-O-Hexadecyl-2-O-methyl-3-O-[6'-N-(12-aminododecyl)-2',6'-diamino-2',6'-dideoxy-glucopyranoside]-sn-glycerol; 1-O-Hexadecyl-2-O-methyl-3-O-[6'-N-(3-aminopropyl)-2',6'-diamino-2',6'-dideoxy-glucopyranoside]sn-glycerol; 1-O-Hexadecyl-2-O-methyl-3-O-[2'-N-(12-aminododecyl)-2',6'-diamino-2',6'-dideoxy-glucopyranoside]-sn-glycerol and 1-O-Hexadecyl-2-O-methyl-3-O-[2'-N-(3-aminopropyl)-2',6'-diamino-2',6'-dideoxy-glucopyranoside]-sn-glycerol.

According to another aspect of the invention, there is provided a method for manufacture of a medicament for treating cancer comprising admixing a compound of formula (I), formula (II), formula (III), formula (IV) or formula (V) with a suitable excipient. The selected compound may be in an effective amount or therapeutic amount, that is, an amount that is suitable for the reduction of size of a tumor and/or for killing cancerous cells, as described herein.

In a preferred embodiment of the invention, the compound is selected from the group consisting of: 1-O-Hexadecyl-2-O-methyl-3-O-(2',6'-diamino-2',6'-dideoxy-α-D-glucopyranosyl)-sn-glycerol; 1-O-Hexadecyl-2-O-methyl-3-O-(2',6'-diamino-2',6'-dideoxy-β-D-glucopyranosyl)-sn-glycerol; 1-O-Hexadecyl-2-deoxy-3-O-(2'6'-diamino-2',6'-dideoxy-β-D-glucopyranosyl)-sn-glycerol; 1-O-Hexadecyloxy-2S/R-amino-3-(-2'-amino-2'-deoxy-β-D-glucopyranosyl)-glycerol; 1-O-Hexadecyloxy-2R-(-α-L-rhamnopyranosyl)-3-amino glycerol; 1-O-Hexadecyloxy-2R—O-methyl-(2'amino-2'deoxy-α-L-glucopyranosyl)-3-amino glycerol; 1-O-Hexadecyl-2-O-methyl-3-O-(4'-benzyl-2',6'-diamino-2',6'-dideoxy-β-L-glucopyranosyl)-sn-glycerol; 1-O-Hexadecyl-2-O-methyl-3-O-(2',6'-diamino-2',6'-dideoxy-α-L-glucopyranosyl)-sn-glycerol; 1-O-Hexadecyl-2-O-methyl-3-O-(4'-benzyl-2',6'-diamino-2',6'-dideoxy-α-L-glucopyranosyl)-sn-glycerol; 1-O-Hexadecyl-2-O-methyl-3-O-[6'-N-(12-aminododecyl)-2',6'-diamino-2',6'-dideoxy-glucopyranoside]-sn-glycerol; 1-O-Hexadecyl-2-O-methyl-3-O-[6'-N-(3-aminopropyl)-2',6'-diamino-2',6'-dideoxy-glucopyranoside]-sn-glycerol; 1-O-Hexadecyl-2-O-methyl-3-O-[2'-N-(12-aminododecyl)-2',6'-diamino-2',6'-dideoxy-glucopyranoside]-sn-glycerol and 1-O-Hexadecyl-2-O-methyl-3-O-[2'-N-(3-aminopropyl)-2',6'-diamino-2',6'-dideoxy-glucopyranoside]-sn-glycerol.

As will be appreciated by one of skill in the art, an "effective amount" is the amount required to kill a desired percentage of the cancerous cells. This percentage may be for example 40%, 50%, 60%, 70%, 80% or 90% or any other amount suitable for reducing the size of a cancerous tumor. The effective amount for a given individual or patient will of course depend on many factors, including the age, weight and general condition of the individual as well as the type and stage of the cancer. For illustrative purposes, a suitable dosage may be 0.1 mg/Kg body weight to 5 mg/Kg body weight, although other suitable dosages may be determined by one of skill in the art using the methods described herein.

While not wishing to be bound to a particular theory or hypothesis, it is believed that GAELS with more than one cationic group will be more potent than the monocationic lead compounds in killing cancer cells and cancer stem cells. We also hypothesize that GAELs with sugars that are not found in mammals will show cytotoxic activity against epithelial cancer cells and cancer stem cells and will have the advantage of presenting non-hydrolysable glycosidic bonds that will increase the half-life of the compounds in vivo.

According to a first aspect of the invention, there are provided methods to synthesize dicationic and tricationic GAEL analogs, as discussed herein.

In another embodiment there are provided methods to synthesize GAELs bearing a rhamnose sugar or monocationic and dicationic L-sugars as discussed herein.

There is also provided a method of killing cancer stem cells and cancer stem cell spheroids by administering effective amount of a compound of formula (I), formula (I'), formula (II), formula (II') formula (III), formula (III'), formula (IV), formula (IV'), formula (V) or formula (V').

In an alternative embodiment, there is provided a method of treating a cancer that is refractory to treatment with existing apoptosis-inducing agents comprising administering to an individual in need of such treatment an effective amount of a compound of formula (I), formula (I'), formula (II), formula (II'), formula (III), formula (III'), formula (IV), formula (IV'), formula (V) or formula (V').

It is of note that monocationic GAEL, 11 has previously been demonstrated to be active against ovarian (OVCAR 3), colon (T84) brain (U251) and lung (A549 and A427) cell lines. Consequently, the more active analogues 1, 56 and 69 will be even more active against these cell lines. Secondly the mechanism of action of the compound is independent of the tissue type so the compounds are expected to be effective against cancer stem cells derived from different cancers, as discussed herein.

In a preferred embodiment the cancer is selected from a group consisting of pancreatic cancer, breast cancer, ovarian cancer, prostate cancer, small cell lung cancer, colon cancer, liver cancer, skin cancer (melanoma) and brain cancer. Ovarian cancer is expected to be particularly susceptible to the GAEL compounds Examples of other suitable cancers include but are by no means limited to: drug resistant cancers (cancers that initially respond and then develop resistance to apoptosis-inducing drugs); recurring cancers (cancers that respond to treatment (surgery/chemotherapy/radiation therapy) and after a while recur), and metastasized or advanced stage cancers (which usually receive palliative care).

As will be well known to one of skill in the art, "recurring" refers to cancers that initially respond positively to treatment such that the tumor disappears to the point where it is undetectable and the patient is said to be in remission. The period of remission is patient and cancer dependent. When the tumor subsequently reappears in such a patient, the cancer is said to have recurred.

A tumor is "resistant" to a chemotherapeutic agent when the initial treatment with the agent results in tumor shrinkage but subsequently the tumor starts to grow and increase in size despite being given the maximum tolerable levels of the agent.

Thus, as discussed above, there is provided a method of treating a resistant cancer or a recurring cancer comprising administering to an individual in need of such treatment an effective amount of a compound of formula (I), formula (I'), formula (II), formula (II'), formula (III), formula (III'), formula (IV), formula (IV'), formula (V) or formula (V').

In a preferred embodiment of the invention, the compound is selected from the group consisting of: 1-O-Hexadecyl-2-O-methyl-3-O-(2',6'-diamino-2',6'-dideoxy-α-D-glucopyranosyl)-sn-glycerol; 1-O-Hexadecyl-2-O-methyl-3-O-(2',6'-diamino-2',6'-dideoxy-β-D-glucopyranosyl)-sn-glycerol; 1; 1-O-Hexadecyl-2-deoxy-3-O-(2'6'-diamino-2',6'-dideoxy-β-D-glucopyranosyl)-sn-glycerol; 1-O-Hexadecyloxy-2S/R-amino-3-(-2'-amino-2'-deoxy-β-D-glucopyranosyl)-glycerol; 1-O-Hexadecyloxy-2R-(-α-L-rhamnopyranosyl)-3-amino glycerol; 1-O-Hexadecyloxy-2R—O-methyl-(2'amino-2'deoxy-α-L-glucopyranosyl)-3-amino glycerol; 1-O-Hexadecyl-2-O-methyl-3-O-(4'-benzyl-2',6'-diamino-2',6'-dideoxy-β-L-glucopyranosyl)-sn-glycerol; 1-O-Hexadecyl-2-O-methyl-3-O-(2',6'-diamino-2', 6'-dideoxy-α-L-glucopyranosyl)-sn-glycerol; 1-O-Hexadecyl-2-O-methyl-3-O-(4'-benzyl-2',6'-diamino-2',6'-dideoxy-α-L-glucopyranosyl)-sn-glycerol; 1-O-Hexadecyl-2-O-methyl-3-O-[6'-N-(12-aminododecyl)-2',6'-diamino-2', 6'-dideoxy-glucopyranoside]-sn-glycerol; 1-O-Hexadecyl-2-O-methyl-3-O-[6'-N-(3-aminopropyl)-2',6'-diamino-2',6'-dideoxy-glucopyranoside]-sn-glycerol; 1-O-Hexadecyl-2-O-methyl-3-O-[2'-N-(12-aminododecyl)-2',6'-diamino-2',6'-dideoxy-glucopyranoside]-sn-glycerol and 1-O-Hexadecyl-2-O-methyl-3-O-[2'-N-(3-aminopropyl)-2',6'-diamino-2',6'-dideoxy-glucopyranoside]-sn-glycerol.

Although there are a large number of chemotherapeutic agents in clinical use for cancer treatment, they have proved to have limited efficacy in the overall treatment of the disease. There is still no cure for the disease and mortality rates are still unacceptably high for most solid tumors. Evidence is accumulating that a major obstacle to preventing the recurrence of the cancer may be due to the role played by CSCs (Garvalov, B. K. and Acker, T., J. Mol. Med. 2011, 89, 95-107; Zobalova, R.; Stantic, M.; Stapelberg, M.; Prokopova, K.; Dong, J.; Truksa, J. et al, Drugs that Kill Cancer Stem-like Cells. In: Shostak S, editor. Cancer Stem Cells Theories and Practice, ISBN: 978-953-307-225-8, 2011; Samadder P. et al., Eur J Med Chem 2014, 78, 225-235). These cells have been implicated in tumor progression, drug resistance and metastases and eliminating or blunting the activity of CSCs is increasingly recognized to be essential towards discovering a cure for the disease (Zobalova, R.; Stantic, M.; Stapelberg, M.; Prokopova, K.; Dong, J.; Truksa, J. et al, Drugs that Kill Cancer Stem-like Cells. In: Shostak S, editor. Cancer Stem Cells Theories and Practice, ISBN: 978-953-307-225-8, 2011). Several approaches to curtail the activity of CSCs in tumors have been suggested (Zobalova, R.; Stantic, M.; Stapelberg, M.; Prokopova, K.; Dong, J.; Truksa, J. et al, Drugs that Kill Cancer Stem-like Cells. In: Shostak S, editor. Cancer Stem Cells Theories and Practice, ISBN: 978-953-307-225-8, 2011). They include direct elimination of the CSCs, targeting the CSC niche to challenge their survival or reducing the aggressive behaviour of the cells by targeting the cellular machinery responsible. The ability of CSCs to resist apoptotic cell death is one of the major reasons for the lack of efficacy of conventional drugs because these drugs invariably kill cells by apoptosis.

An effective way to eliminate CSCs will be to develop compounds that kill cells by non-apoptotic mechanism. Such compounds will by-pass the variety of strategies used by CSCs to evade cell death by apoptosis. Since we have previously demonstrated that GAELs kill cells by a non-apoptotic mechanism that involves generation of acidic vacuoles (Samadder, P. et al., Anticancer Res. 2011, 31, 3809-3818; Samadder, P. et al., Anticancer Res. 1998, 18, 465-470; Xu, Y. et al., Chem Med Chem 2013, 8, 511-520; Arthur, G. and Bittman, R. Anticancer Agents Med Chem. 2014, 14, 592-606; Jahreiss, L. et al., Autophagy 2009, 5, 835-846), we postulated that GAELs could potentially be toxic against CSCs.

Figure 1:
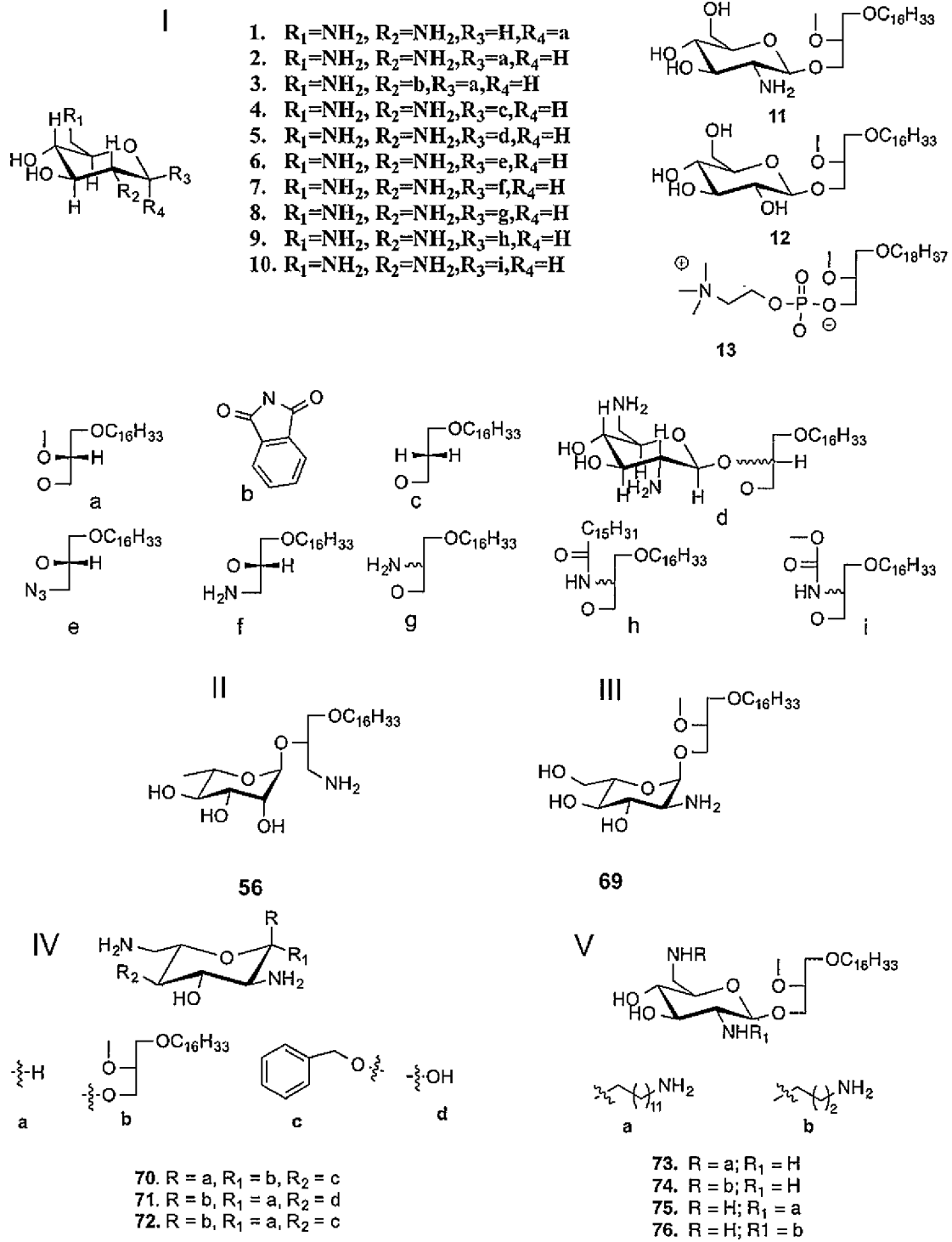
FIG. 1. Structures of the synthesized glycolipids evaluated for anticancer properties (Formulas (I), (II), (III), (IV), (V)) and structures of related compounds in formulas (I'), (II'), (III'), (IV'), (V)') which differ from formula (I), (II), (III), (IV), (V)) by variations of the sugar moiety. Compounds 11, 12 and 13 are reference compounds and not covered in this patent FIG. 2A. Effects of compounds 1-11 on the viability of MDA-MB231 cells. MDA-MB-231 cells were cultured in DMEM medium supplemented with 10% FBS. Equal numbers were dispersed into 96-well plates. After 24 h, the cells were incubated with compounds 1-11 (0-30 μM) for 48 h. At the end of the incubation, MTS reagent (20% vol/vol) was added and the plates were incubated for 1-4 h. The $OD_{490}$ was read with a plate reader. Wells with media but no cells were treated in similar fashion and the values utilized as blank. The results represent the mean±standard deviation of 6 independent determinations.

GAELs containing amino substituent at $C_2$ position of the sugar moiety have been reported to show higher toxicity to cancer cells compared to an analog without a cationic moiety like compound 12 (Erukulla, R. V. et al., J. Med. Chem. 1996, 39, 1545-1548). To synthesize novel analogs more active than reference compound 11, we designed and synthesized compounds 1-10, as shown in FIG. 1. As discussed herein, compounds 1, 2, 4 and 8 with free diamino substituents were significantly more active than our reference compound Gln 11. This shows that dicationic GAEL analogs with the sugar moiety at the sn3 position of the glycerolipid are more active.

The lack of activity of compound 3 in comparison to Gln 11 despite the free amine at the $C_6$ position of the sugar shows that the amino substituent at the $C_2$-position of the sugar is very significant for anticancer activity.

Comparison of activity of compounds 6 and 7 with that of compound 8 showed that the position of the sugar and the second cationic substituent on the glycerolipid is important for their anticancer activity.

The significantly higher activity of compound 2 when compared to that of compound 8 shows that the presence of two amino substituents on the sugar moiety is optimal for anticancer activity. Additional substitution of compound 2 with a second diamino sugar moiety as in compound 5 or acylation of the exocyclic amino group in 8 by a fatty acid as in compound 9 greatly reduce anticancer activity. This may be due to effects of these substitutions on physical properties of these compounds which significantly may affect their pharmacokinetic properties especially absorption. Unlike edelfosine, replacement of the methoxy group at sn2-position of the glycerolipid with methyl carbamate significantly reduced anticancer activity in GAEL analog and it did not enhance selectivity toward prostate cancer.

Tricationic GAELs as well as GAELs with L sugars also possess the ability to cause the disintegration of CSCs spheroids/aggregates and kill the cells.

The ability of the dicationic GAELs to cause the disintegration of cancer stem cell spheroids derived from breast and prostate cell lines is an indication that the structural changes that have been made, relative to the prototypic Gln, have not nullified the mechanism of action of the compound. The ability to disrupt CSC spheroids and kill the cells is an indication that they share the common mechanism of killing the CSCs via an apoptosis-independent mechanism.

In summary, our SAR studies show that the nature of the sugar greatly affects the cytotoxicity against cancer cell lines. For instance, we demonstrated that monocationic 1-O-Hexadecyl-2-O-methyl-3-O-(2'-amino-2'-deoxy-α-D-galactopyranosyl)-sn-glycerol is more active than 1-O-Hexadecyl-2-O-methyl-3-O-(2'-amino-2'-deoxy-α-D-glucopyranosyl)-sn-glycerol against various cancer cell lines (Samadder P et al. Eur J Med Chem. 2014, 78, 225-35). As a result, we can infer that the dicationic and tricationic D-galactose-based analogs would be as active or more active than the di- and tricationic D-glucose analogs. Moreover, as we have demonstrated the dicationic L-glucose-based GAEL 1-O-Hexadecyl-2-O-methyl-3-O-(2',6'-diamino-2',6'-dideoxy-α-L-glucopyranosyl)-sn-glycerol 69 to be as active as the dicationic D-glucose version 1-O-Hexadecyl-2-O-methyl-3-O-(2',6'-diamino-2',6'-dideoxy-α-D-glucopyranosyl)-sn-glycerol 2 we can infer that the dicationic L-galactose analogs will also be active and even more so than the glucose-versions.

The invention will now be further elucidated by way of examples; however, the invention is not necessarily limited to the examples.

2. Results 2.1.1. Synthesis of Dicationic GAELs Analogs 1-10.

It is of note that the synthesis protocols outlined below illustrate one method for the synthesis of the compounds described herein. Modifications to these methods will be apparent to one of skill in the art and/or can be determined by routine experimentation and are within the scope of the invention.

To synthesize dicationic GAEL analogs that are potentially more active than the lead compound, monocationic Gln 11, an amino substituent was introduced to the $C_6$-position of the sugar to give compounds 1-4. The rationale behind introduction of extra amino substituent at this position is because previous reports showed that the non-cationic analog compound 12 was less potent than edelfosine 13 which in turn was less potent than Gln 11 (Erukulla, R. V. et al., *J. Med. Chem.* 1996, 39, 1545-1548; Samadder, P. et al., *Anticancer Res.* 1998, 18, 465-470; Xu, Y. et al., *Chem Med Chem* 2013, 8, 511-520). Evidently, the amino substituent on $C_2$ position of the sugar in Gln 11 increased activity, so we hypothesized that an additional amino substituent in 11 may increase the anticancer activity of the compound.

Compounds 1 and 2 were synthesized to evaluate the effect of the configuration of the glycosidic linkage on activity, though a previous report showed that the α-anomer of Gln 11 was more active than the β-anomer.

Compound 3, with a phthalimido at the C2-position of the sugar, was synthesized to study how the absence of cationic group at C-2 affects the activity in this compound series. The reason behind this is that previous studies showed that when the free amine at the $C_2$-position of the sugar was modified with various substituents such as azide, guanidyl, and benzyl amine derivatives, the anticancer activity were significantly reduced, up to or greater than 3 fold (Samadder, P. et al., *Anticancer Res.* 2011, 31, 3809-3818; Xu, Y. et al., Chem Med Chem 2013, 8, 511-520; Jahreiss, L. et al., *Autophagy* 2009, 5, 835-846).

Compounds 4 and 5 were synthesized to explore the effect of the methoxy substituent at the sn2 position of the glycerol moiety. Another reason for synthesizing 5 was to investigate if an additional diamino substituted sugar moiety will increase activity compared to a methoxy substituent at sn2 position of the glycerol backbone.

Compounds 6-8 were synthesized to explore how the position of the second amino group in the glycerolipid affected the antitumor properties.

Compound 9 was synthesized to explore how the presence of two lipid tails and modification of the free amino substituent at sn-2 position affect the biological properties in compound 8.

We also synthesized selected carbamate 10 to explore whether the presence of a methoxycarbamate substituent at the sn-2-position of the glycerolipid will promote selectivity for prostate cancer as a previous study has shown that edelfosine analogs bearing a methoxycarbamate functionality at that position was selective for prostate cancer (Byun, H-S. et al., Chem Med Chem, 2010, 5, 1045-1052).

Compounds 5, 8, 9, and 10 are diastereomeric mixtures of two compounds based on the stereochemistry at the sn-2-position of the glycerolipid. We have previously reported that the stereochemistry at position 2 has little or no effect on anticancer activity and edelfosine, the most studied antitumor ether lipid, is usually used as a racemic mixture (Ogunsina, M. et al., Molecules, 2013, 18, 15288-15304).

Compound 1 was synthesized by coupling of glycoside donor 20 to the commercially available lipid alcohol 21 to give a mixture of α- and β-glycolipid 22 and 23, respectively (4:1) (see Scheme 1). The glycoside donor 20 was synthesized from glucosamine hydrochloride 14 in 7 steps. The amino substituent of glucosamine 14 was converted to azide as previously reported (Xu, Y. et al., *Chem Med Chem* 2013, 8, 511-520) in the presence of cupric sulphatepentahydrate, water and triethylamine at room temperature overnight. This was followed by acetate protection of the hydroxyl group using acetic anhydride in pyridine in the presence of DMAP at room temperature overnight to give compound 15. The thiophenyl glycoside 16 was synthesized from 15 using thiophenol and boron trifluoride diethyl etherate complex in dichloromethane at room temperature for 18 hrs. To install the azido function at the $C_6$-position, the acetate protection was removed using sodium methoxide in methanol to give compound 17 which was subsequently converted to sulphonate ester 18 using toluenesulfonyl chloride in pyridine with DMAP as the catalyst at room temperature. Nucleophilic displacement of sodium azide in DMF produced 2,6-diazido analog 19 which was subsequently protected using acetic anhydride in pyridine with DMAP as the catalyst to give the glycoside donor 20. The α-glycolipid 22 was isolated in pure form and then deprotected to remove the acetate group to afford the 2,6-diazido compound 24 which was subsequently reduced with trimethylphosphine in THF to give the α-configured diamino compound 1.

To synthesize compounds 2-5, the glycoside donor 30 was glycosylated to the lipid alcohol 21, 34 and 37 to produce the protected glycolipid analogs 31, 34 and 38 (see Scheme 2). We have previously reported the synthesis of lipid alcohol 34 (Xu, Y. et al., Chem Med Chem 2013, 8, 511-520), and lipid alcohol 37 is commercially available. The glycoside donor 30 was synthesized from the glucosamine hydrochloride 14 in seven steps. Glucosamine hydrochloride 14 was dissolved in aqueous solution of sodium hydroxide to which phthalic anhydride was added to protect the amino substituent and the reaction mixture was left overnight at room temperature. The water was removed and the residue dispersed in pyridine followed by addition of acetic anhydride for acetate protection of the hydroxyl group to give compound 25. The procedures used to convert compound 15 to glycoside donor 20 described above were repeated to convert 25 to the glycoside donor 30. Removal of the acetate and phthalimido protecting group were done in one reaction using ethylenediamine in butanol (1:1) at 90° C. for 2 h which converted compounds 31, 35 and 38 to their 6-azido glycolipid analogs 36 and 39, respectively. The acetate protective groups of compound 31 were selectively removed using a catalytic amount of sodium methoxide for 20 minutes to give 6-azido-2-phthalimido glycolipid analog 33. Reduction of the azido function in compounds 32, 33, 36 and 39 was achieved by using trimethylphosphine in THF and water (9:1) to produce the desired target compounds 2-5 respectively.

To synthesize compounds 6 and 7, the azido lipid alcohol 42 was synthesized from the commercially available lipid diol 40 in two synthetic steps. Compound 40 was converted to sulphonate ester 41 using toluene sulfonyl chloride in pyridine and DMAP as catalyst. The azide 42 was synthesized from 41 by nucleophilic substitution reaction using sodium azide in DMF. The glycoside donor 26 was glycosylated with 42 to afford the protected glycolipid 43. The acetate and phthalimido protective groups of 43 were removed with ethylenediamine in butanol (1:1) at 90° C. for 2 hrs to give the desired compound 6. The azido substituent of 6 was reduced as described above to give the diamino analog 7.

To synthesize compound 8, the glycoside donor 26 was glycosylated to the lipid alcohol 44, which was synthesized from the commercially available lipid alcohol as previously reported (Byun, H.-S. et al., Chem Med Chem, 2010, 5, 1045-1052). The glycosylation reaction gave the protected glycolipid compound 45. Reduction of the azido substituent at position sn2 of the glycerolipid gave compound 46 which was subsequently deprotected using ethylenediamine in butanol (1:1) at 90° C. for 2 hrs to give the desired compound 8.

To synthesize compound 9, the amine 46 was coupled using TBTU to the palmitic acid 47 (Bera, S. et al., Molecules 2012, 17, 9129-9141) to give compound 48 which was subsequently deprotected using ethylenediamine in butanol (1:1) at 90° C. for 2 hrs to produce the compound of choice 9.

Compound 10 was synthesized by reacting the methyl chloroformate 49 with amine 46 to give the carbamate 50 which was subsequently deprotected using ethylenediamine in butanol (1:1) at 90° C. for 2 hrs to afford the carbamate analog 10 as the desired compound (Byun, H.-S. et al., Chem Med Chem, 2010, 5, 1045-1052).

2.1.2. Synthesis of L-Rhamnose Derived GAEL 56 and L-Glucosamine Derived GAEL 69

To enhance metabolic stability, we synthesized L-rhamnose derived GAEL analog 56 and L-glucosamine derived GAEL 69, where we employed L-sugars that are not naturally present in humans because they are expected to resist glycosidases breakdown in human. To synthesize compound 56, we employed the chemistry described above for the synthesis of compound 7 (see scheme 5). For the synthesis of compound 69, we started with the commercially available L-mannose 57 which was converted to protected L-glucosamine analog 65 in eight synthetic steps (see Scheme 6). L-mannose 57 was acetylated to give the pentaacetate 58 which was converted to the bromide 59 using HBr in acetic acid (33% w/w). The bromide 59 was subjected to phase transfer catalyzed anomeric $S_N2$ nucleophilic substitution reaction using tetrabutyl ammonium hydrogen sulphate and sodium carbonate in an immiscible mixture of ethyl acetate and water to give the phenyl β-L-thiomanopyranoside 60 which was subsequently deprotected to give 61. The hydroxyl group at $C_3$ position was selectively protected by benzyl ester to give compound 62. The hydroxyl functional groups at the $C_4$ and $C_6$ position were protected together using benzylidienediacetal to give compound 68. We tried to employ triflic anhydride to activate the —OH substituent at $C_2$ position for subsequent conversion using $S_N2$ nucleophilic substitution reaction to give the L-glucosamine derivative 65, but this approach was not successful. So we used the mesylate 64 which worked. As described above, the protected glucosamine derivative 65 was glycosylated to lipid 21 to give the protected glycolipid 66 as mainly α anomer (90%). The benzylidenediacetal protecting group was removed using an acetic acid water mixture (80/20) at 60° C. for 3 hrs to give 67. The benzoate ester was subsequently removed using excess sodium methoxide in methanol for 2 hrs to give the azide 68 which was subsequently reduced as described above to give the target compound 69.

2.1.3. Synthesis of L-Gluco-Based Glycolipids 70-72.

The synthesis of compound 70 started from compound 63 as previously outlined herein. Regioselective ring opening of the benzylidine ring under reductive diborane conditions afforded diol 77. Both hydroxyl groups in 77 were activated as sulfonate esters and nucleophilic displacement of the sulfonate esters with sodium azide in DMF at elevated temperature produced diazido-thioglycoside 79. NIS activated glycosylation of thioglycoside donor 79 with commercially available lipid alcohol 21 produced an anomeric mixture of L-gluco-based β-glycoside 80 and L-gluco-based α-glycoside 81. Saponification of the ester functionality in 80 and 81 using basic sodium methoxide in methanol produced alcohols 82 and 83, respectively. Reduction of both azide groups in glycolipid 82 using trimethylphosphine in aqueous THF produced target compound 70. Using the same conditions to diazido-based α-glycolipid 83 gave target compound 71. Finally exposure of 71 to catalytic hydrogenation using palladium on charcoal produced unprotected target compound 72.

2.1.4. Synthesis of D-Gluco-Based Tricationic Glycolipids 73-76.

Target compounds 73 and 74 were prepared from previously prepared glycolipid 33. At first the 6-azido group in glycolipid 33 was reduced by catalytic hydrogenation to produce 6-amino-based glycolipod 3. Reductive amination of the amino function in 3 with various azido aldehydes 89 generated phthalimido-protected glycolipid 84. Deprotection of the phthalimido group using ethylendiamine in butanol at elevated temperature produced azido-based glycolipid 85 which was exposed to catalytic hydrogenation to produce target compounds 73 and 74.

Target compounds 75 and 76 were prepared from preciously described phthalimido-protected glycolipid 33. Removal of the phthalimido group using ethylendiamine in butanol at elevated temperature generated amine 32 which reacted with various azido aldehydes 89 using reductive amination conditions to afford diazido analogs 88. Catalytic hydrogenation of diazido-based glycolipids using catalytic hydrogenation gave the desired target tricationic glycolipids 75 and 76.

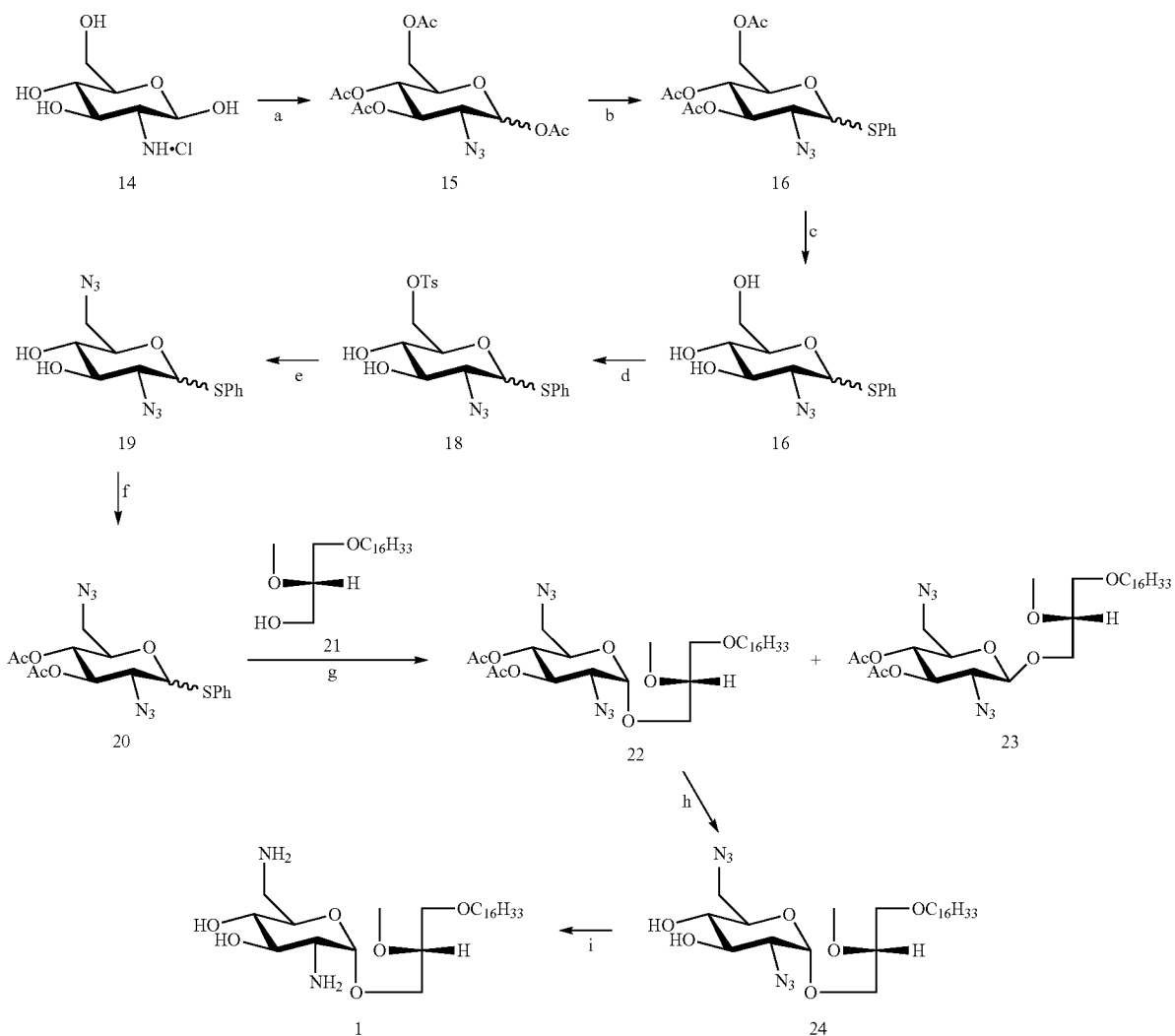

Scheme 1. Synthesis of compound 1.

Reagents and conditions:
(a) 1. TfN$_3$, CuSO$_4$, ETN$_3$, H$_2$O, rt; 2. Ac$_2$O, DMAP, Pyridine, 18 hrs, rt
(b) PhSH, BF$_3$·Et$_2$O, DMAP, DCM, 18, hrs, rt
(c) MeONa, MeOH, 1 hr
(d) TsCl, Pyridine, DMAP, 0° C. - rt, 18 hrs
(e) DMF, NaN$_3$, 70° C.
(f) Ac$_2$O, DMAP, Pyridine, 18 hrs, rt (g) AgOTf, NIS, DCM, 3 hrs, rt
(h) MeONa, MeOH, 30 minutes (i) P(CH$_3$)$_3$, THF, H$_2$O, 2 hrs, rt.

Abbreviations:
4-Dimethyl amino pyridine (DMAP), Dichloromethane (DCM), 2,2,N,N-dimethylformamide (DMF), room temperature (rt), N-iodosuccinimide (NIS)

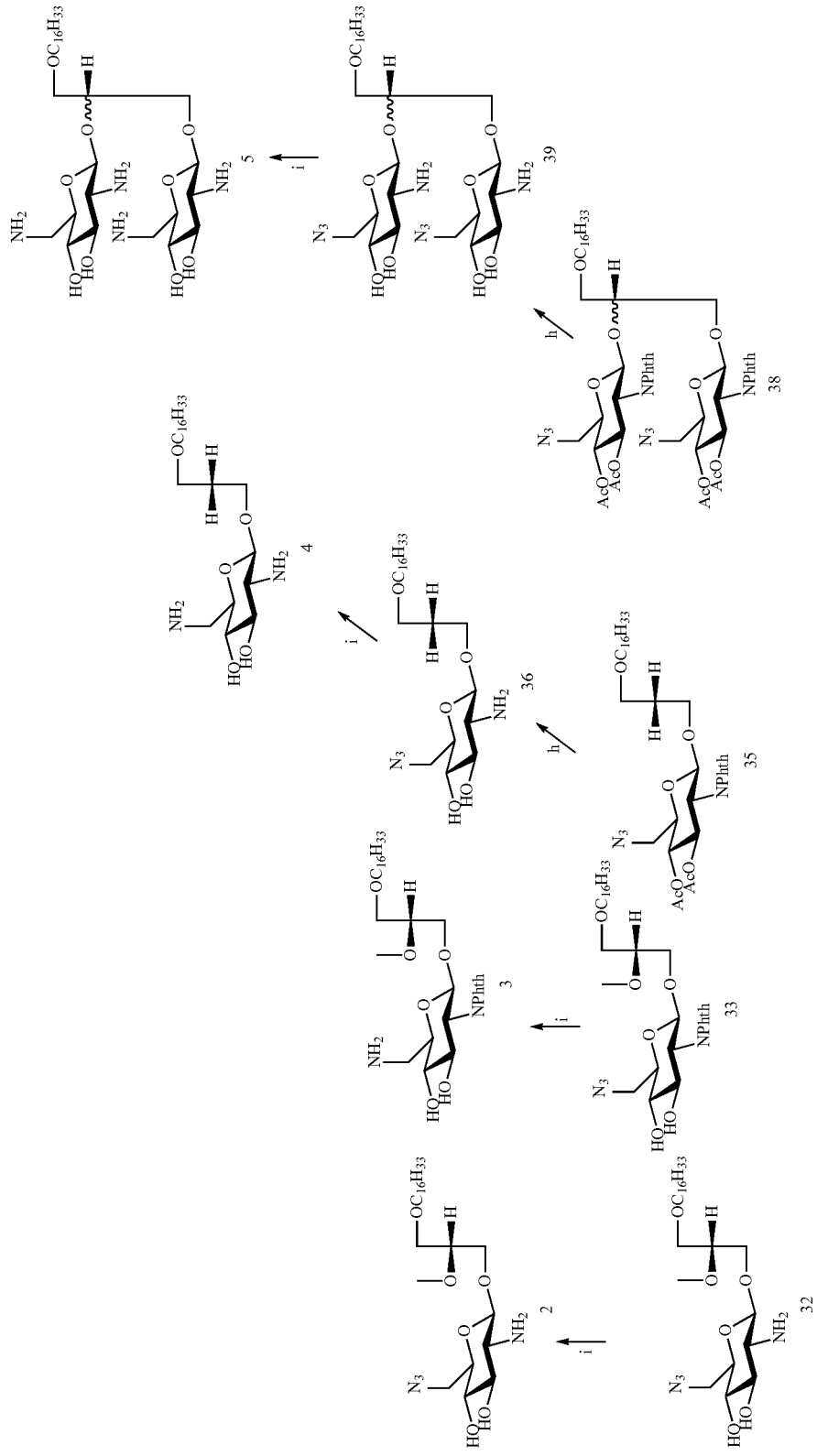
Scheme 2. Synthesis of compounds 2-5.

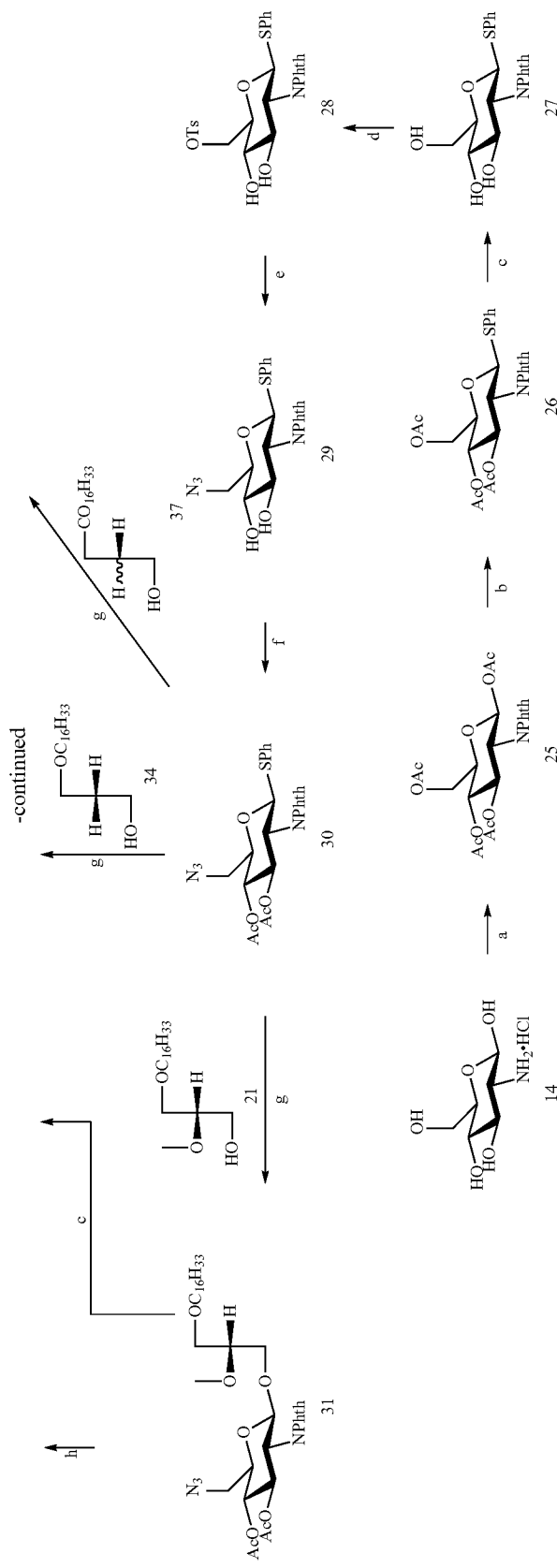

Reagents and conditions:
(a) 1. Phthalic anhydride, NaOH, H₂O, 18 hrs, rt; 2. Ac₂O, DMAP, Pyridine, 18 hrs, rt
(b) PhSH, BF₃·Et₂O, DMAP, DCM, 18 hrs, rt
(c) MeONa, MeOH, 20 minutes
(d) TsCl, Pyridine, DMAP, 0° C.-rt, 18 hrs
(e) DMF, NaN₃, 70° C.
(f) Ac₂O, DMAP, Pyridine, 18 hrs, rt
(g) AgOTf, NIS, DCM, 3 hrs, rt
(h) Ethylenediamine/butanol (1:1), 90° C. 2 hrs, rt
(i) P(CH₃)₃, THF, H₂O, 2 hrs, rt Abbreviations:
4-Dimethyl amino pyridine (DMAP), Dichloromethane (DCM), 2,2,N,N-dimethylformamide (DMF), room temperature (rt),
N-iodosuccinimide (NIS)

Scheme 3. Synthesis of compounds 6 and 7.
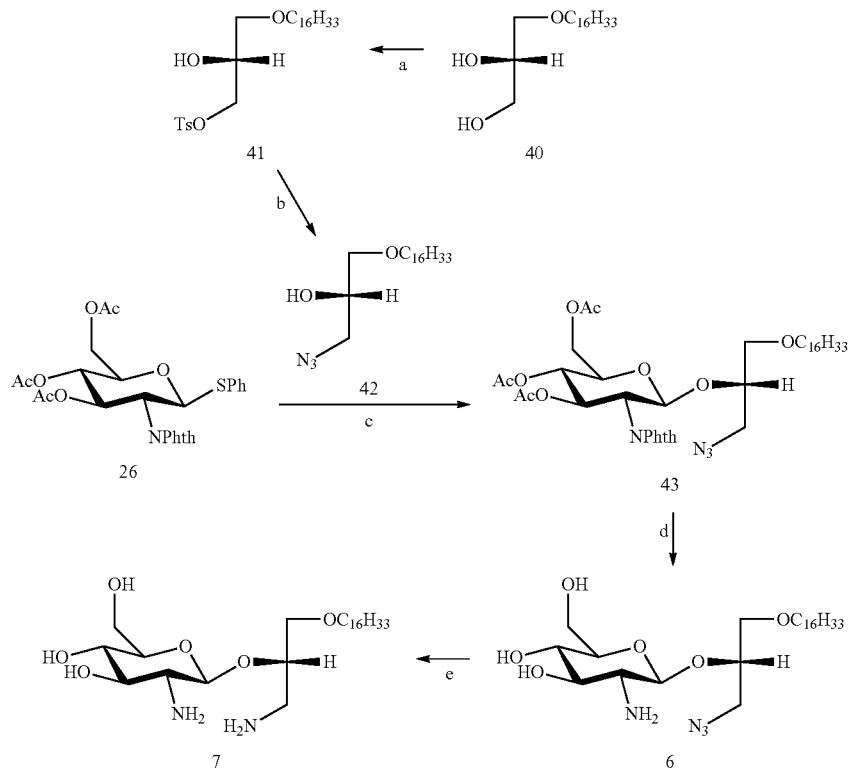
Reagents and conditions:
(a) TsCl, Pyridine, DMAP, 0° C. - rt, 18 hrs
(b) DMF, NaN$_3$, 70° C.
(c) AgOTf, NIS, DCM, 3 hrs, rt
(d) Ethylinediamine/butanol (1:1), 90° C. 2 hrs, rt
(e) P(CH$_3$)$_3$, THF, H$_2$O, 2 hrs, rt.
Abbreviations:
4-Dimethyl amino pyridine (DMAP), Dichloromethane (DCM), 2,2,N,N-dimethylformamide (DMF), room temperature (rt), N-iodosuccinimide (NIS)
Scheme 4. Synthesis of compound 8-10.
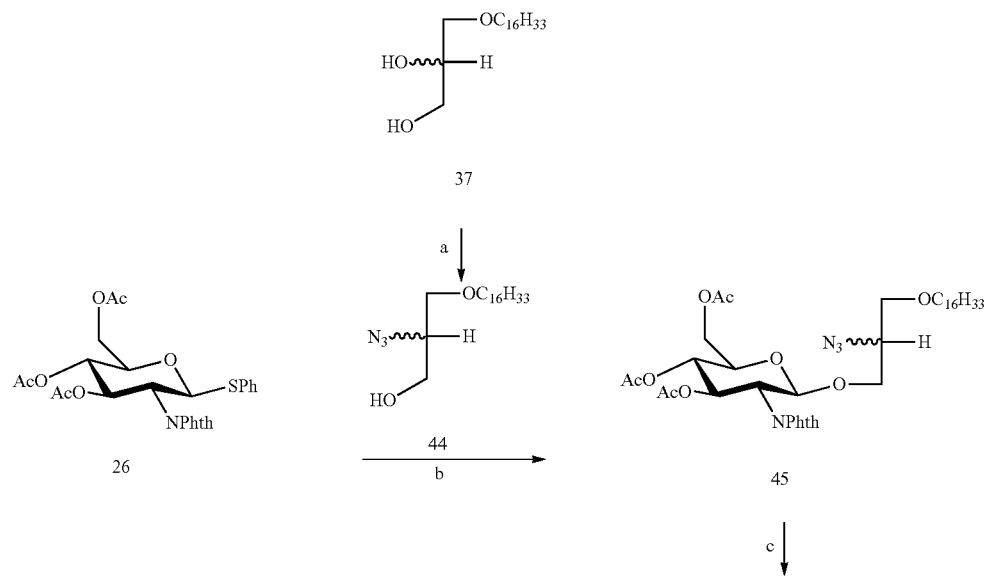

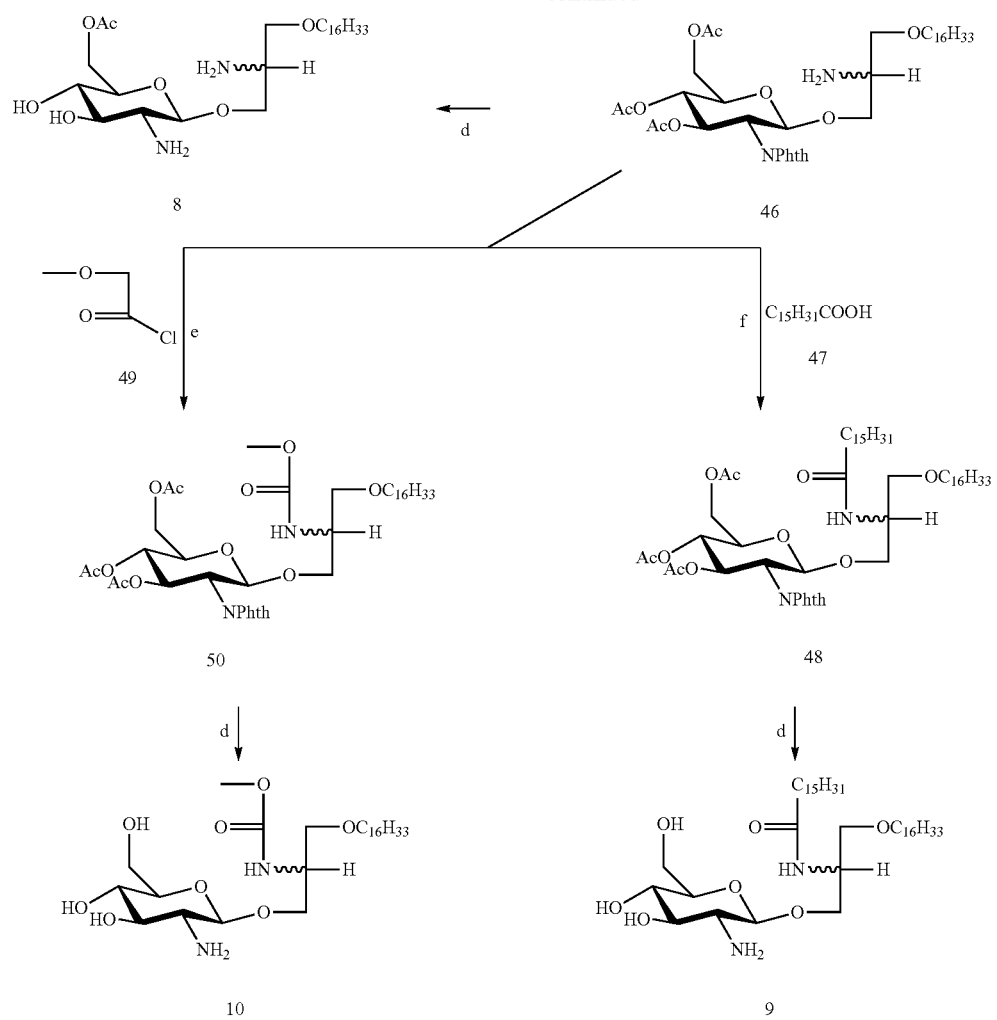

Reagents and conditions:
(a) DIAD, Ph₃P, Me₃SiN₃, DCM, (b) AgOTf, NIS, DCM, 3 hrs, rt (c) P(CH₃)₃, THF, H₂O, 2 hrs, rt (d) Ethylinediamine/butanol (1:1), 90° C. 2 hrs, rt, (e) Et₃N, ClCO₂Me, DCM, (f) TBTU, DIPEA, DMF, 3 hrs, rt.

Abbreviations:
4-Dimethyl amino pyridine (DMAP), Dichloromethane (DCM), 2,2,N,N-dimethylformamide (DMF), room temperature (rt), N-iodosuccinimide (NIS), Diisopropylethylamine (DIPEA), Diisopropylazodicarboxylate (DIAD).

Scheme 5. Synthesis of compound 56 (mo-1-157C).

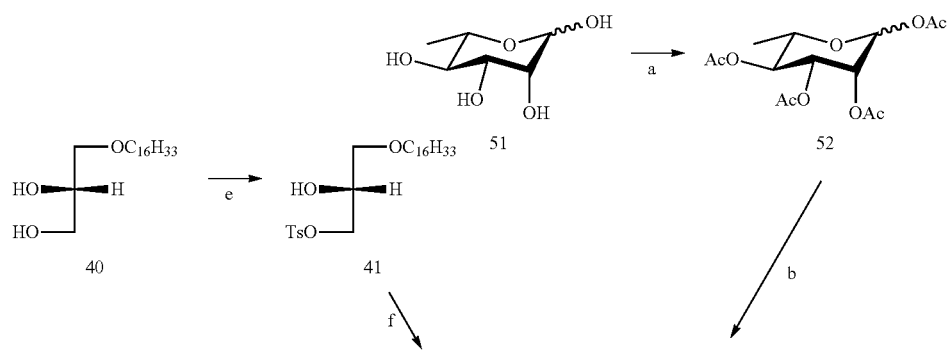

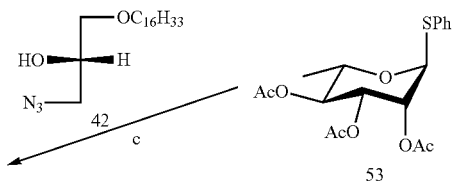
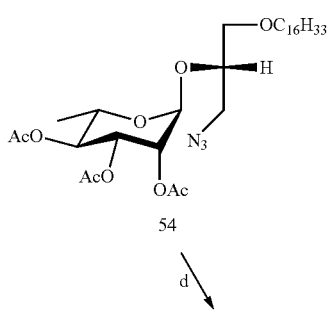
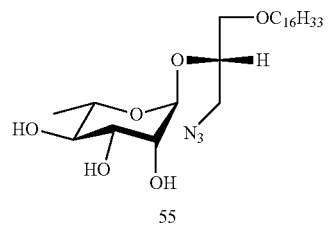 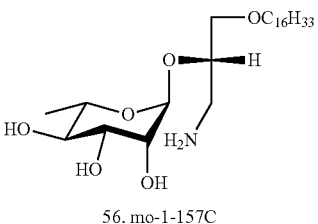
Reagents and conditions:
(a) Ac₂O, DMAP, Pyridine, 18 hrs, rt
(b) PhSH, BF₃·Et₂O, DCM, 18, hrs, rt
(c) AgOTf, NIS, DCM, 3 hrs, rt
(d) MeONa, MeOH, 1 hr minutes
(e) TsCl, Pyridine, DMAP, 0° C. - rt, 18 hrs
(f) DMF, NaN₃, 70° C.
(g) P(CH₃)₃, THF, H₂O, 2 hrs, rt.
Abbreviations:
4-Dimethyl amino pyridine (DMAP), Dichloromethane (DCM), 2,2,N,N-dimethylformamide (DMF), room temperature (rt), N-iodosuccinimide (NIS)
Scheme 6. Synthesis of compounds of L-Gln.
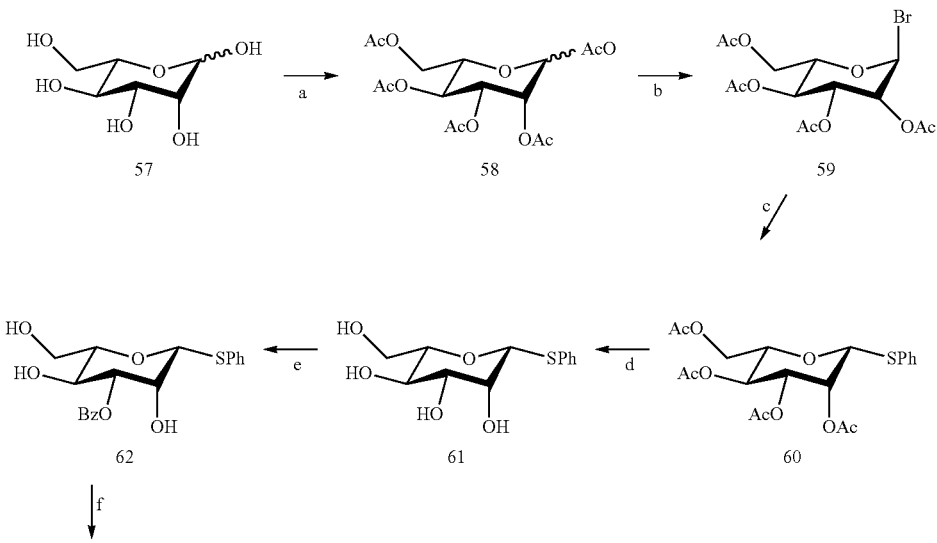

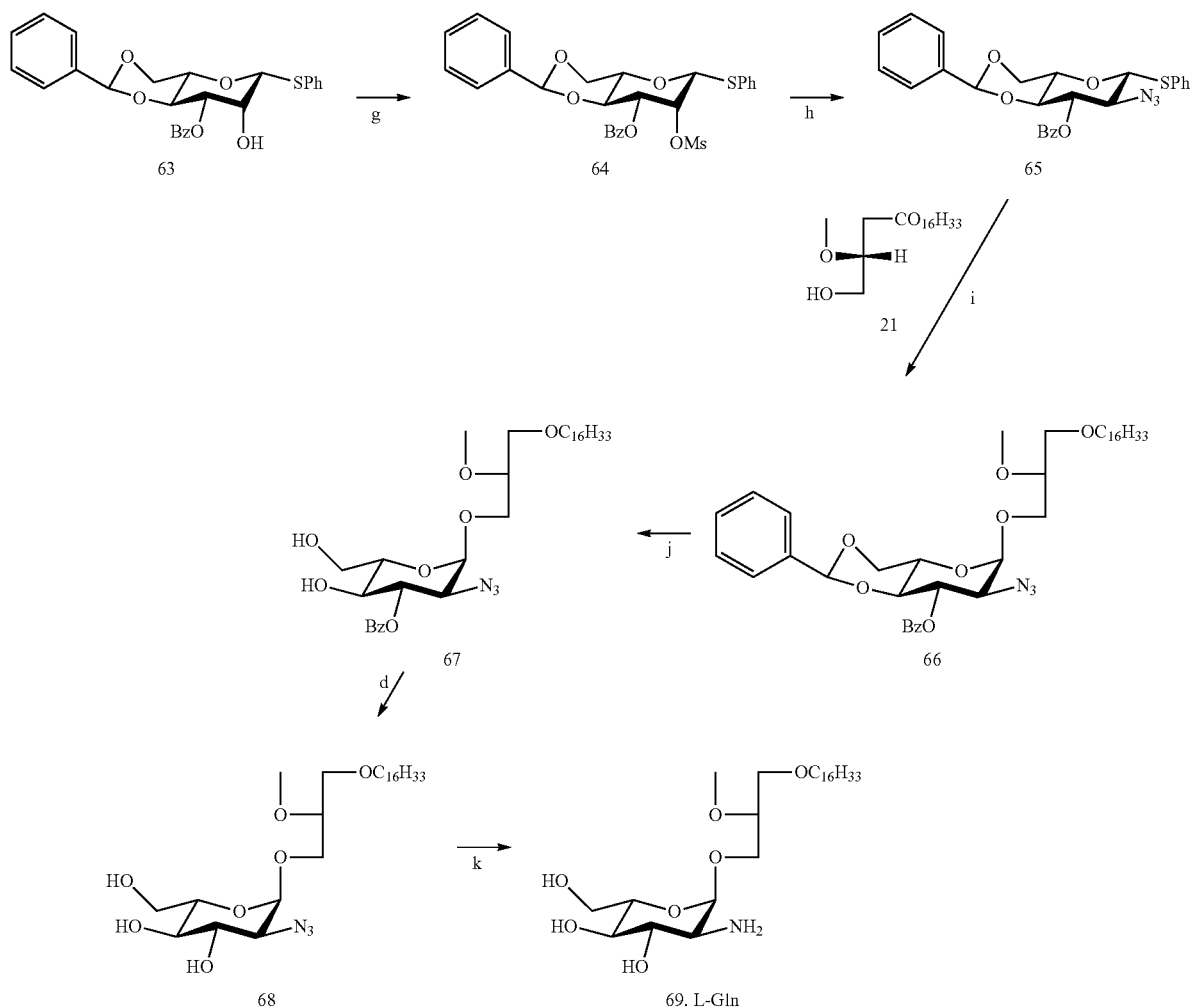
Reagents and conditions:
(a) Ac₂O, DMAP, Pyridine, 18 hrs, rt
(b) HBr in AcOH (33%), DCM, 0° C., 2 hrs
(c) PhSH, EtOAc, H₂O, Na₂CO₃, TBAHS, rt, 6 hrs
(d) MeONa, MeOH, 1 hr
(e) Me₂SnCl₂, BzCl, DIPEA, THF/H₂O (19:1), rt, 16 hrs
(f) PhCH(OMe)₂, CSA, CH₃CN, rt, 4 hrs
(g) MsCl, Pyridine, DMAP, rt, 18 hrs
(h) DMF, NaN₃, 120° C.
(i) AgOTf, NIS, DCM, 3 hrs, rt
(j) AcOH, H₂O, 60° C., 5 hrs
(k) P(CH₃)₃, THF, H₂O, 2 hrs, rt
Scheme 7. Synthesis of Compounds 70-72.
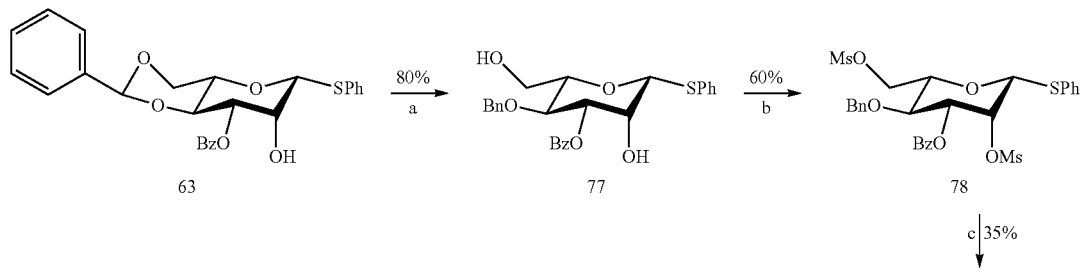

-continued
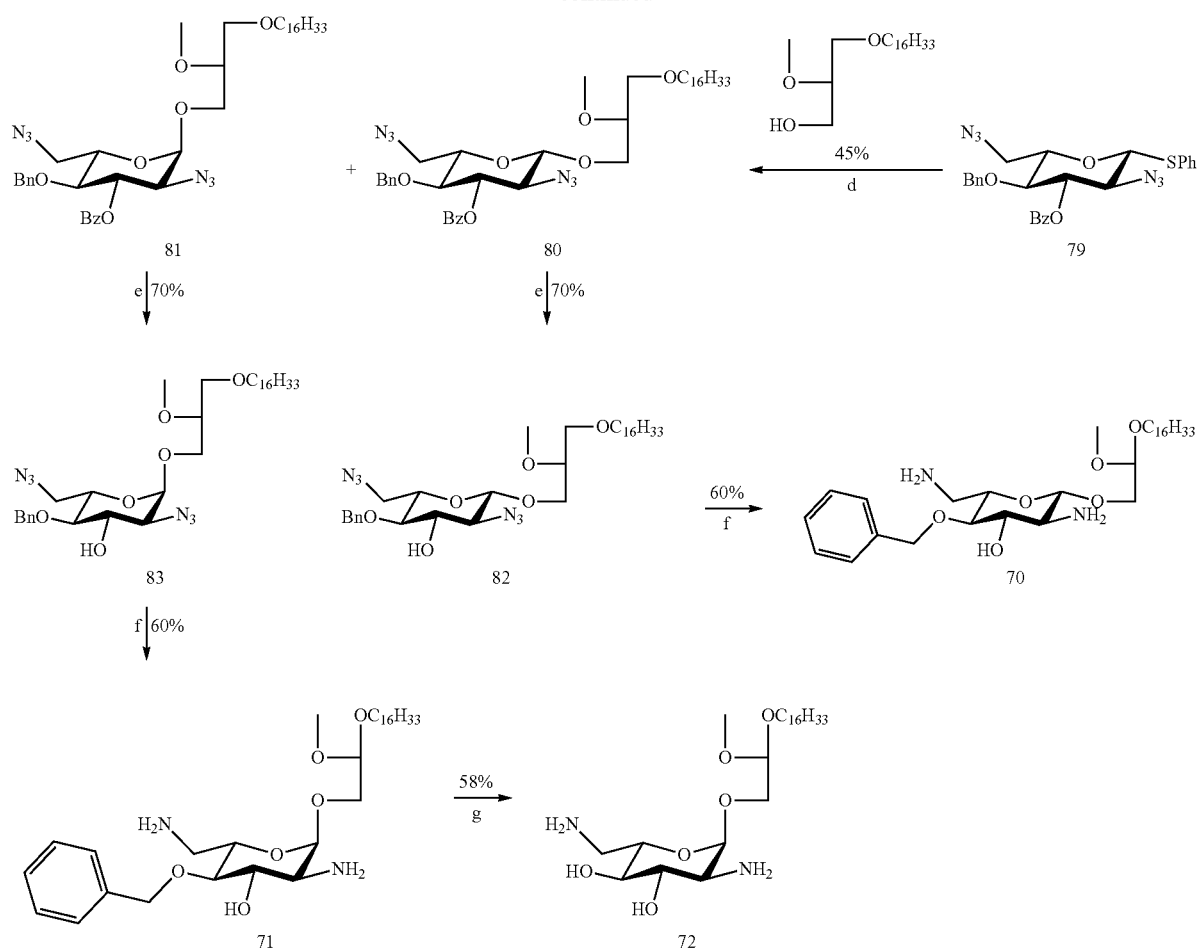
Reactions and Conditions;
(a) BH$_3$·THF, TMSOTf, DCM, 4 hrs
(b) MsCl, DMAP, Pyridine
(c) DMF, NaN$_3$, 140° C.
(d) AgOTf, NIS, DCM
(e) NaOMe, MeOH, 5 hrs
(f) P(CH$_3$)$_3$, THF, H$_2$O, 2 hrs
(g) H$_2$, Pd, MeOH, 5 hrs
Scheme 8. Synthesis of compounds 73-76
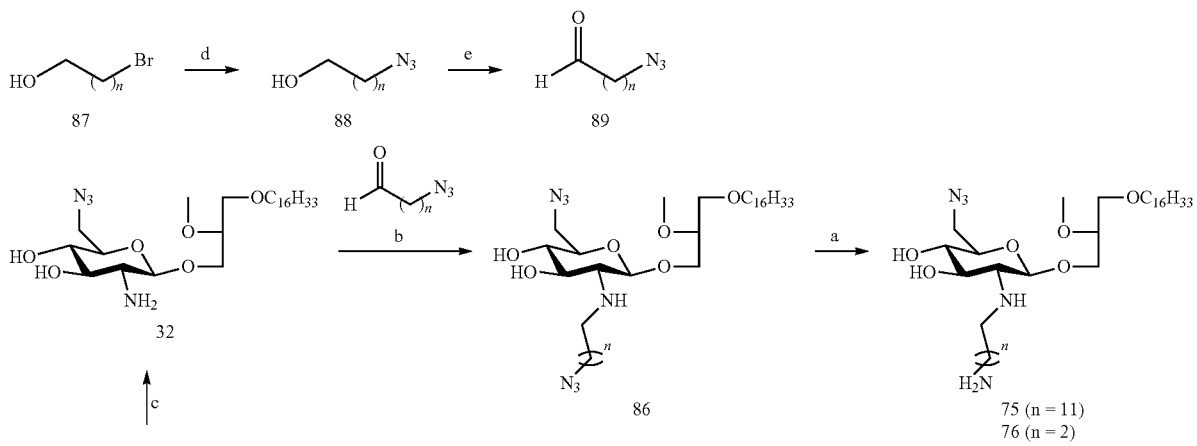

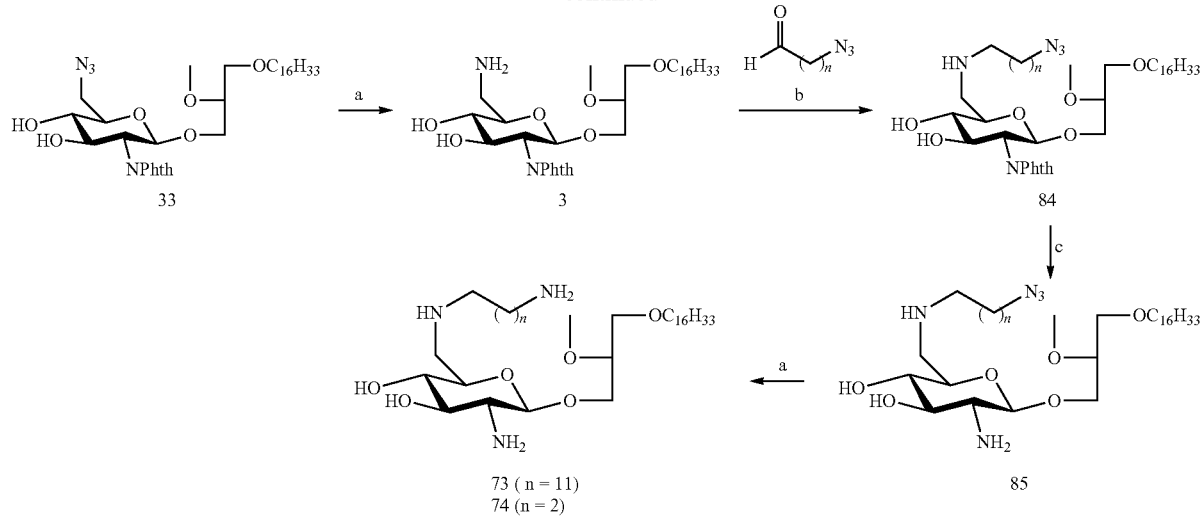

Reactions and conditions:
a) Pd(OH)$_2$/C, H$_2$, 2 h;
b) i) DCM, 0° C. to RT, overnight, ii) NaBH$_4$, CH$_3$COOH, 2 h;
c) ethylenediamine, butanol, 90° C., 3 h;
d) NaN$_3$, DMF, 70° C., 3 h;
e) PCC, DCM, 2 h

2.3. In Vitro Screening Against Epithelial Cancer Cell Lines
2.3.1 Effect of Dicationic GAELs (1-10).

To determine the effect of compounds 1-10 on the viability of the epithelial cancer cell lines, exponentially growing cells, BT-474, JIMT-1, MDA-MB-231 (breast), DU145, PC3 (prostate), MiaPaCa2 (pancreas) were incubated with varying concentrations of 1-8 (0-30 μM) for 48 h followed by viability assays with the MTS reagent. The results of the viability studies are shown in FIGS. 2A to 2E.

Gln11, a monocationic and the most studied GAEL was selected as the reference compound for comparison with the new dicationicglycolipids.

The CC$_{50}$ values for all the compounds are summarized in Table 1 and the CC90 values are summarized in Table 2.

The most potent of the compounds tested against all six cell lines is α-dicationic glycolipid 1 with CC$_{50}$ values of 3.0 to 7.5 μM depending on the cell line. 90% loss of cell viability was observed at a concentration range 4.5-9.5 μM depending on cell lines.

Figures 1, 2:
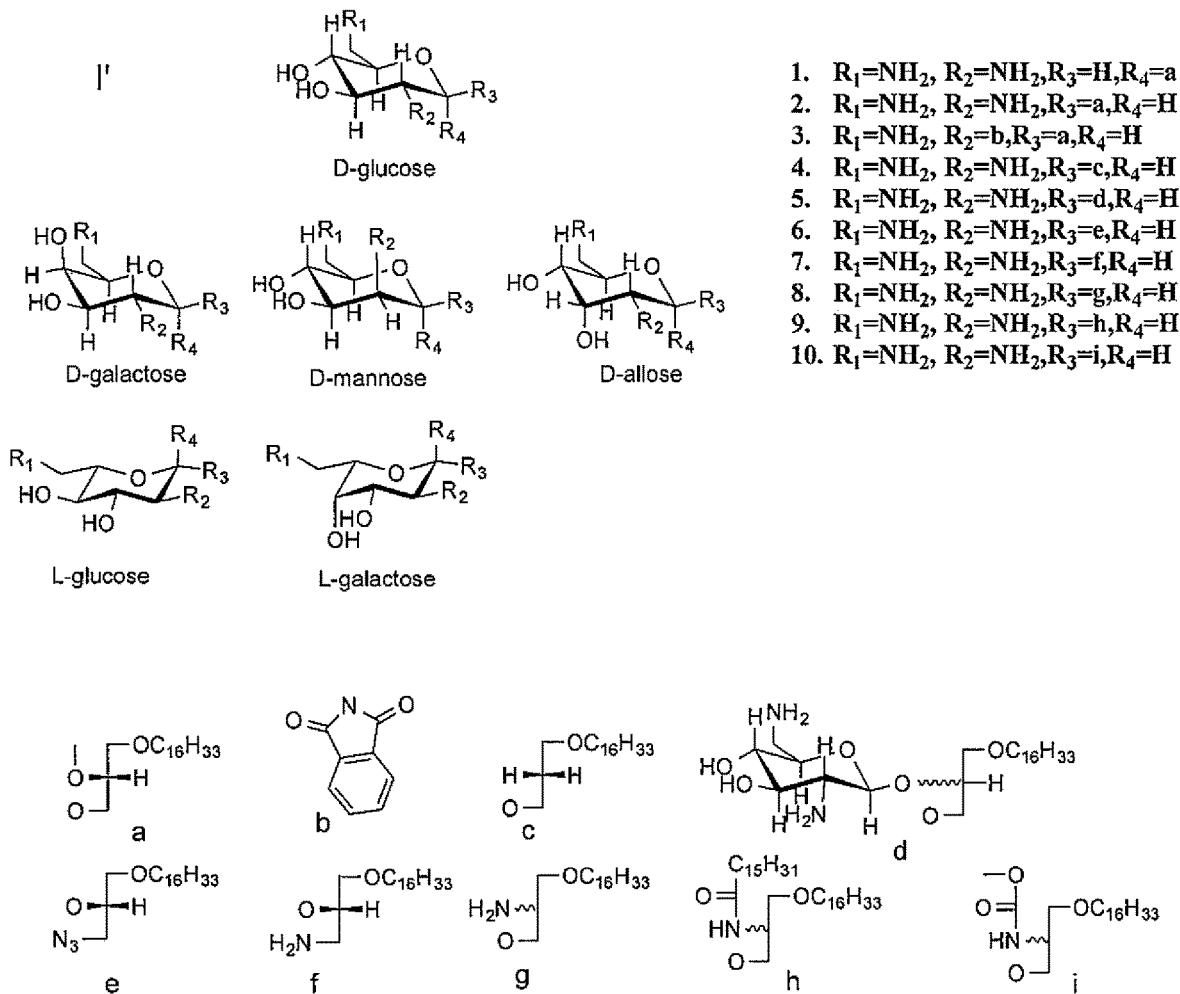

Comparison of 1 with the β-dicationic analog 2 with CC$_{50}$ values in the range of 4.2-11.5 μM, showed that the α-analog 1 is consistently more active against all the cell lines (see FIG. 2). This shows that as previously reported for the monocationic analog 11 (Samadder P. et al., Eur J Med Chem 2014, 78, 225-235), the α-analogs of this class of compounds are more active.

Comparison of the β-dicationic analog 2 with 13-monocationic analog 11, CC$_{50}$ value in the range of 8-13.5 μM showed that 2 is significantly more active across all the six cell lines except BT 474 cell lines.

Compound 3 with phthalimido substituent at C$_2$ position of the sugar and free amine at C$_6$ position of the sugar has CC$_{50}$ values in the range of 15→30 μM and it is significantly less active than the reference monocationic analog 11 against all cell lines. This showed that unmodified amino substituent at the C$_2$ position is essential for activity.

Compound 4, an analog of 2 without a methoxy substituent at the position sn 2 of the glycero moiety has activity comparable to that of 2 and showed a CC$_{50}$ value in the range of 4.0-8.5 μM. In fact, there was no statically significant difference between the activity of 2 and 4 for all the cell lines except BT 474. This suggests that the methoxy substituent may have no significant role on activity.

The diastereomeric mixture and deglycosylated analog 5 was not able to reduce viability of cells by 50% at the highest dose tested, 30 μM. Thus, replacing the methoxy substituent at sn2 position of the glycerol moiety with another dicationic sugar reduced activity significantly. This may be due to increased hydrophilicity leading to reduced cellular absorption.

Compounds 6-8 were synthesized primarily to determine the effect of the position of the sugar on the glycerolipid.

The azide compound 6 has CC$_{50}$ values in the range of 6-22 μM. It was significantly more sensitive to PC-3 cell lines than Gln, 6.0 μM compared to 13.5 μM and least sensitive to BT 474 cell lines when compared to Gln, 22 μM compared to 8 μM. For other cell lines the activities are comparable.

The dicationic analog 7 is significantly less active than 6 across all cell lines. This may be attributed to possible physical interaction between the primary amino substituent on sn3 of the lipid and the amino substituent at the C$_2$ position of the sugar which may alter the conformation of the compound.

Compound 8 with the sugar moiety on sn 3-position of the glycerolipid, when compared to compounds 6 and 7 with the lipid position on sn 2 position, was significantly more active than Gln 11 except against the BT 474 cell line. This result shows that activity of this class of compound is better when the sugar moiety is on sn3 position of the glycerolipid. The increased potency of compound 8 compared to Gln 11 against most of the cell lines also shows that replacement of the methoxy group at the sn 2-position of the glycerolipid with an amino substituent significantly increased the activity.

Also, comparison of activity of compounds 7 and 8 with that of 1, 2, and 4 demonstrates better activities can be achieved when the two amino groups are located on the sugar as compared to when the sugar has one and the other is on the lipid.

Compound 9, with a second hydrophobic $C_{16}$ moiety attached to the sn 2-position of the glycerolipid, was not active at the highest concentration tested, 30 µM. At this dose, there was no significant difference in viability compared to the control across all the cell lines tested. Lack of activity may be due to increased lipophilicity which might have decreased the cellular absorption of the drug.

Compound 10, with a methylcarbamate substituent at the sn 2-position of the glycerolipid, was synthesized to promote selectivity against prostate cancer cell lines. The rationale is because an edelfosine analog substituted at this position has selectivity against prostate cancer cell lines. The $CC_{50}$ values of compound 10, which is in the range of 14-23 µM, is significantly less active than Gln11. This shows that carbamate substituent neither increased activity nor promoted selectivity for prostrate cell line in the GAEL series compared to the edelfosine series. This also confirms difference in anticancer properties of GAELs and that of other AELs.

Effect of Tricationic GAELs

Figure 2A:
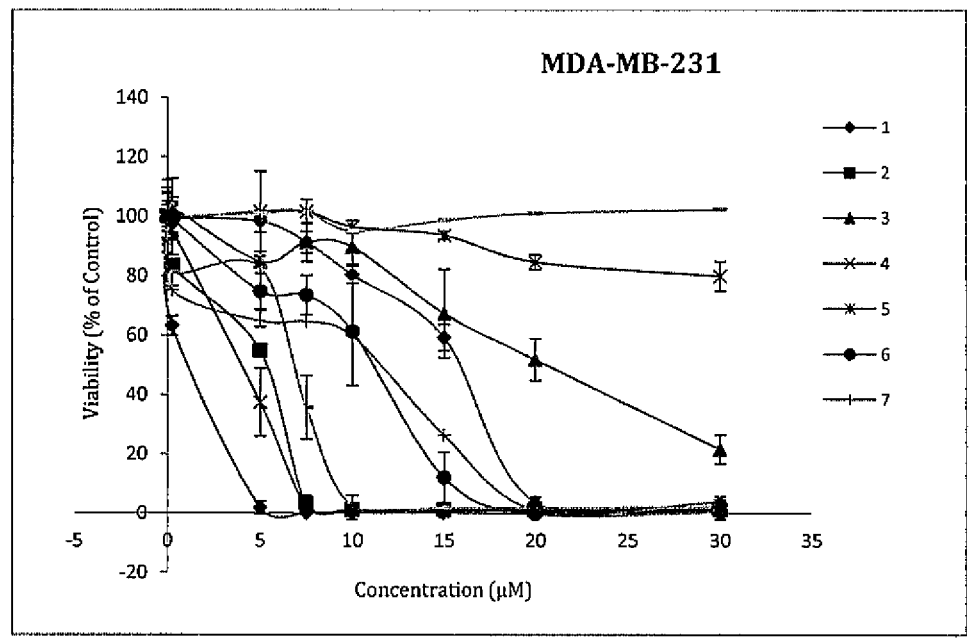
FIG. 2B. Effects of compounds 1-11 on the viability of JIMT-1 cells. JIMT-1 cells were cultured in DMEM medium supplemented with 10% FBS. Equal numbers were dispersed into 96-well plates. After 24 h, the cells were incubated with compounds 1-11 (0-30 μM) for 48 h. At the end of the incubation, MTS reagent (20% vol/vol) was added and the plates were incubated for 1-4 h. The $OD_{490}$ was read with a plate reader. Wells with media but no cells were treated in similar fashion and the values utilized as blank. The results represent the mean±standard deviation of 6 independent determinations.
FIG. 2C. Effects of compounds 1-11 on the viability of BT-474 cells. BT-474 cells were cultured in DMEM/F12 medium supplemented with 10% FBS. Equal numbers were dispersed into 96-well plates. After 24 h, the cells were incubated with compounds 1-11 (0-30 μM) for 48 h. At the end of the incubation, MTS reagent (20% vol/vol) was added and the plates were incubated for 1-4 h. The $OD_{490}$ was read with a plate reader. Wells with media but no cells were treated in similar fashion and the values utilized as blank. The results represent the mean±standard deviation of 6 independent determinations.
FIG. 2D. Effects of compounds 1-11 on the viability of DU145 cells. DU145 cells were cultured in DMEM medium supplemented with 10% FBS. Equal numbers were dispersed into 96-well plates. After 24 h, the cells were incubated with compounds 1-11 (0-30 μM) for 48 h. At the end of the incubation, MTS reagent (20% vol/vol) was added and the plates were incubated for 1-4 h. The $OD_{490}$ was read with a plate reader. Wells with media but no cells were treated in similar fashion and the values utilized as blank. The results represent the mean±standard deviation of 6 independent determinations.
FIG. 2E. Effects of compounds 1-11 on the viability of PC3 cells. PC3 cells were cultured in F12K medium supplemented with 10% FBS. Equal numbers were dispersed into 96-well plates. After 24 h, the cells were incubated with compounds 1-11 (0-30 μM) for 48 h. At the end of the incubation, MTS reagent (20% vol/vol) was added and the plates were incubated for 1-4 h. The $OD_{490}$ was read with a plate reader. Wells with media but no cells were treated in similar fashion and the values utilized as blank. The results represent the mean±standard deviation of 6 independent determinations.
FIG. 2F. Effects of compounds 1-11 on the viability of MiaPaCa2 cells. MiaPaCa2 cells were cultured in DMEM medium supplemented with 10% FBS and 2.5% horse serum. Equal numbers were dispersed into 96-well plates. After 24 h, the cells were incubated with compounds 1-11 (0-30 μM) for 48 h. At the end of the incubation, MTS reagent (20% vol/vol) was added and the plates were incubated for 1-4 h. The OD490 was read with a plate reader. Wells with media but no cells were treated in similar fashion and the values utilized as blank. The results represent the mean±standard deviation of 6 independent determinations.
FIG. 2G. Effect of compounds 1, 11, 56, 69 or 73 on the viability of A2780s, A2780cp, U87 and U251 cells. A2780s and A2780cp cells were cultured in DMEM/F12 medium supplemented with 10% FBS. U251 and U87 cells were cultured in DMEM supplemented with 10% FBS. Equal numbers were dispersed into 96-well plates. After 24 h, the cells were incubated with the GAELs compounds 1, 11, 56, 69 or 73 for 48 h. At the end of the incubation, MTS reagent (20% vol/vol) was added and the plates were incubated for 1-4 h. The $OD_{490}$ was read with a plate reader. Wells with no cells were treated in a similar fashion and the values utilized as blank. The results represent the mean±standard deviation of 6 independent determinations.
FIG. 2H. Effect of compounds 1, 69-72 on the viability of DU145 cells. DU145 cells were cultured in DMEM medium supplemented with 10% FBS. Equal numbers were dispersed into 96-well plates. After 24 h, the cells were incubated with compounds 1, 69-72 for 48 h. At the end of the incubation, MTS reagent (20% vol/vol) was added and the plates were incubated for 1-4 h. The $OD_{490}$ was read with a plate reader. Wells with media but no cells were treated in similar fashion and the values utilized as blank. The results represent the mean±standard deviation of 6 independent determinations.
FIG. 2I. Effects of compounds 1, 69-72 on the viability of MiaPaCa2 cells. MiaPaCa2 cells were cultured in DMEM medium supplemented with 10% FBS and 2.5% horse serum. Equal numbers were dispersed into 96-well plates. After 24 h, the cells were incubated with compounds 1, 69-72 for 48 h. At the end of the incubation, MTS reagent (20% vol/vol) was added and the plates were incubated for 1-4 h. The $OD_{490}$ was read with a plate reader. Wells with media but no cells were treated in similar fashion and the values utilized as blank. The results represent the mean±standard deviation of 6 independent determinations.
FIG. 2J. Effects of compounds 1, 69-72 on the viability of JIMT-1 cells. JIMT-1 cells were cultured in DMEM medium supplemented with 10% FBS. Equal numbers were dispersed into 96-well plates. After 24 h, the cells were incubated with compounds 1, 69-72 for 48 h. At the end of the incubation, MTS reagent (20% vol/vol) was added and the plates were incubated for 1-4 h. The $OD_{490}$ was read with a plate reader. Wells with media but no cells were treated in similar fashion and the values utilized as blank. The results represent the mean±standard deviation of 6 independent determinations.
FIG. 2K. Effects of compounds 1, 69-72 on the viability of MDA-MB-231 cells. MDA-MB-231 cells were cultured in DMEM medium supplemented with 10% FBS. Equal numbers were dispersed into 96-well plates. After 24 h, the cells were incubated with compounds 1, 69-72 for 48 h. At the end of the incubation, MTS reagent (20% vol/vol) was added and the plates were incubated for 1-4 h. The $OD_{490}$ was read with a plate reader. Wells with media but no cells were treated in similar fashion and the values utilized as blank. The results represent the mean±standard deviation of 6 independent determinations.
FIG. 2L to 2N. Effects of compounds 1, 56 or 69 on the viability of primary epithelial ovarian cancer cells grown as adherent and spheroid cultures. EOC cells were isolated from the ascites of ovarian cancer patients. Cells were seeded in regular 96-well plates and grown as adherent cultures. 24 h after seeding the cells were incubated with compounds 1, 56, or 69 for 48 h and the viability of the cells were determined with the MTS assay. Spheroid cultures were obtained by seeding the cells in ultra-low adhesion 96-well plates for 3 days. The spheroids were incubated with compounds 1, 56 or 69 for 3 days. At the end of the incubations, MTS reagent (20% vol/vol) was added and the plates were incubated for 1-4 h. The $OD_{490}$ was read with a plate reader. Wells with media but no cells were treated in similar fashion and the values utilized as blank. The results represent the mean±standard deviation of 6 independent determinations.
FIG. 2O. Effect of compound 73 on the viability of epithelial cancer cell line. BT474, PC3, MiaPaCa2, JIMT1, DU145 and MDA-MB-231 cells were grown in their respective growth medium described in the methods section. Equal numbers were dispersed into 96-well plates. After 24 h, the cells were incubated with compound 73 for 48 h. At the end of the incubation, MTS reagent (20% vol/vol) was added and the plates were incubated for 1-4 h. The $OD_{490}$ was read with a plate reader. Wells with media but no cells were treated in a similar fashion and the values utilized as blanks. The results represent the mean±standard deviation of 6 independent determinations.
Figure 2B:
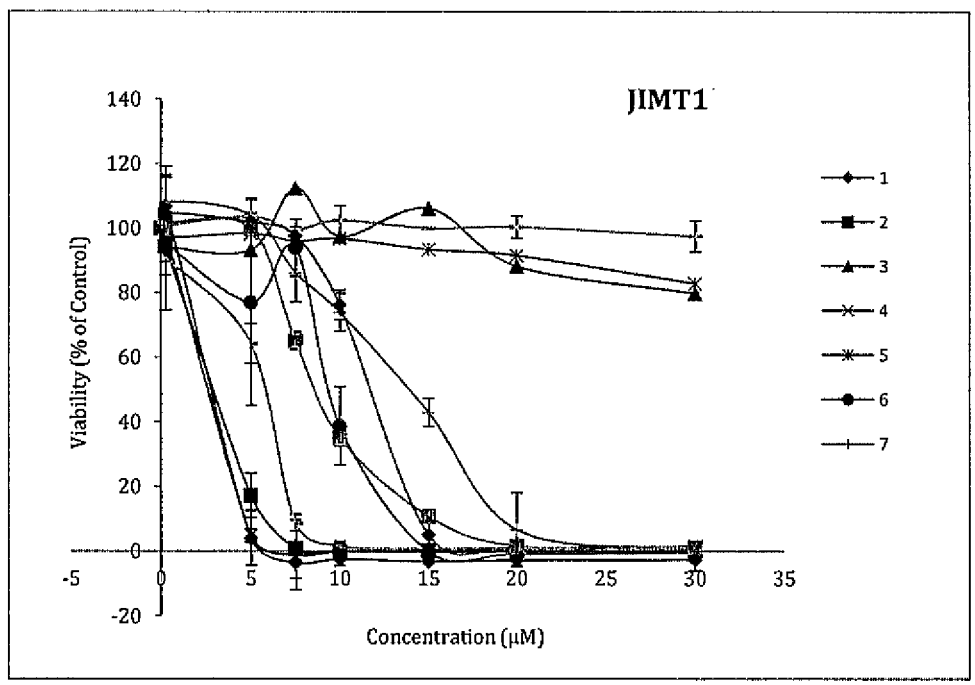
Figure 2C:
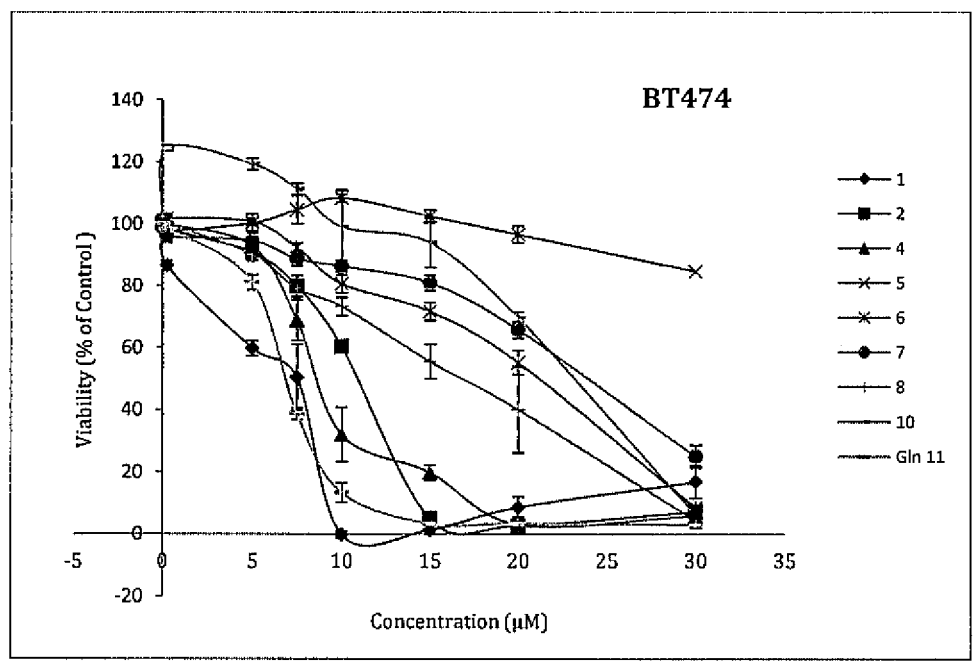
Figure 2D:
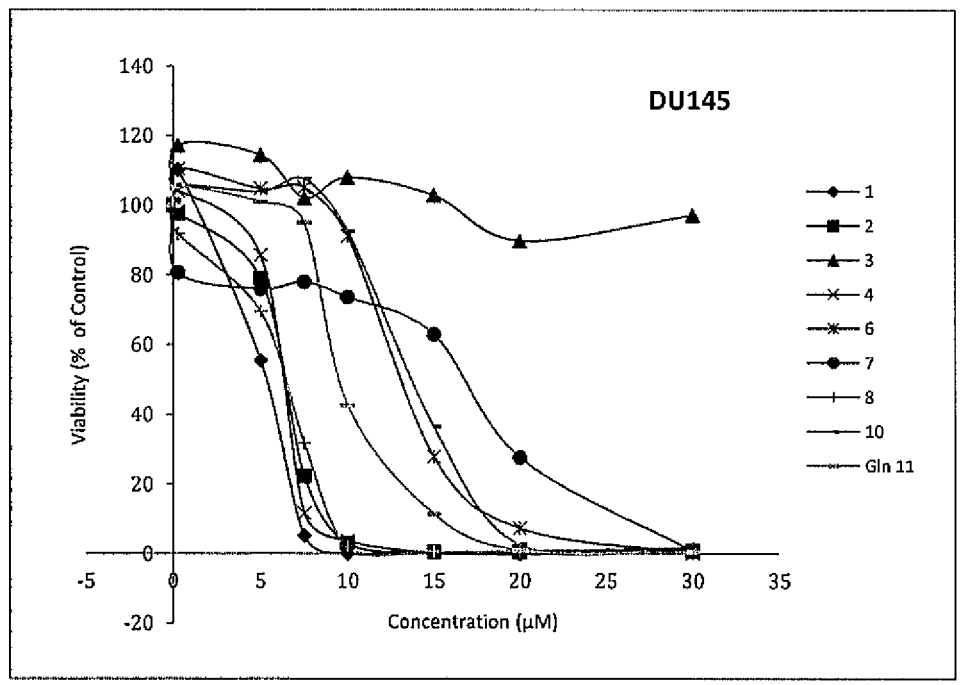
Figure 2E:
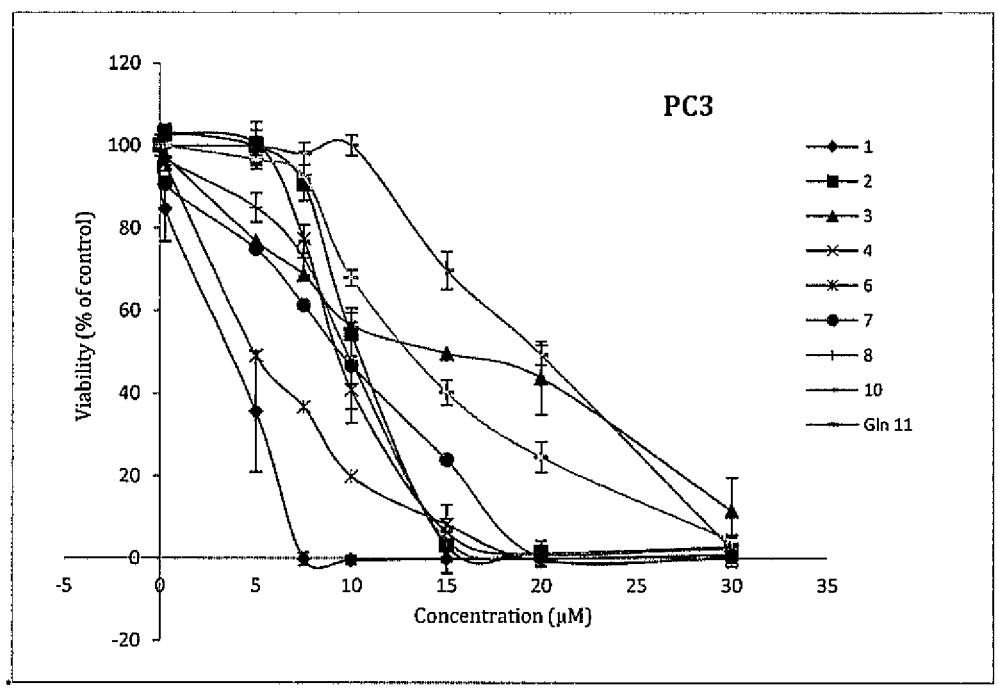
Figure 2F:
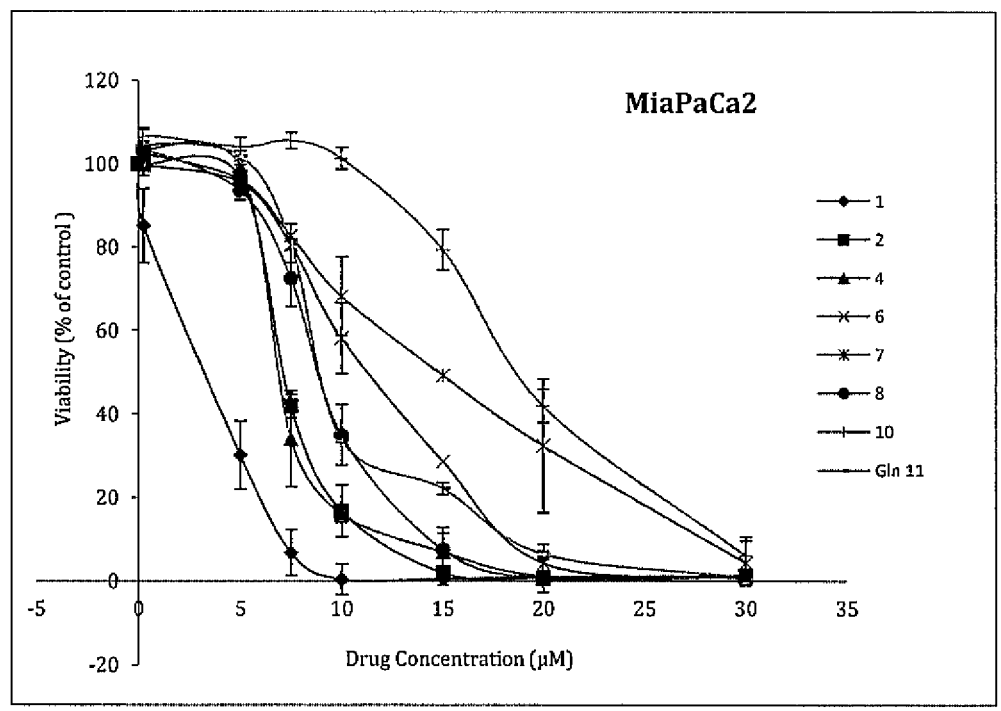
Figure 2H:
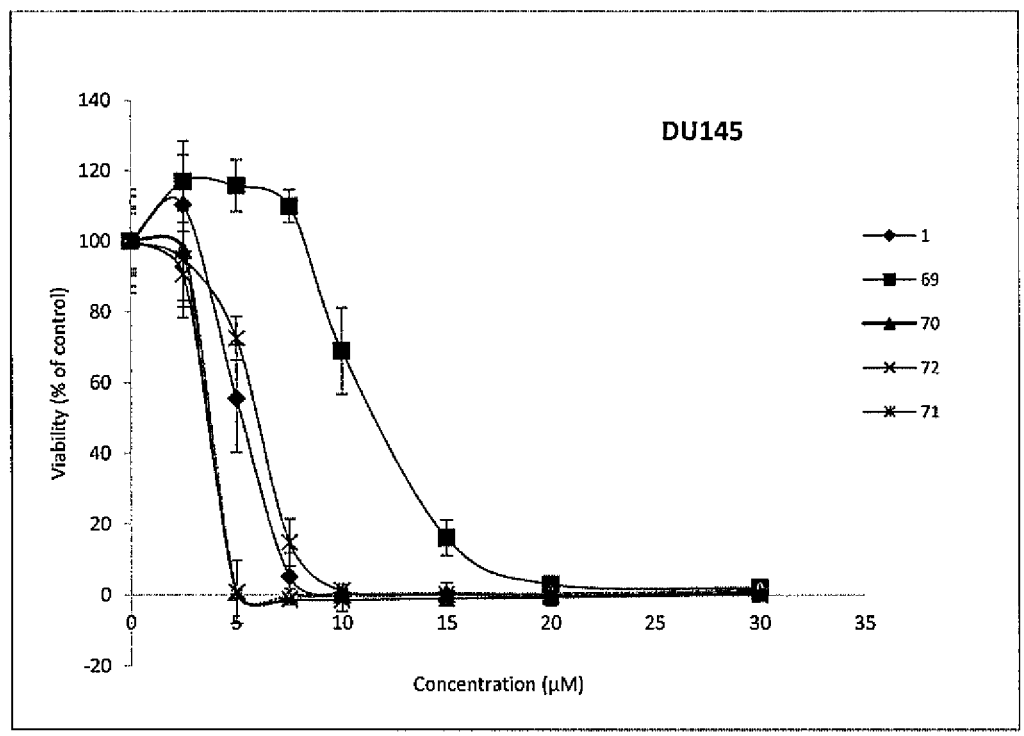
Figure 2I:
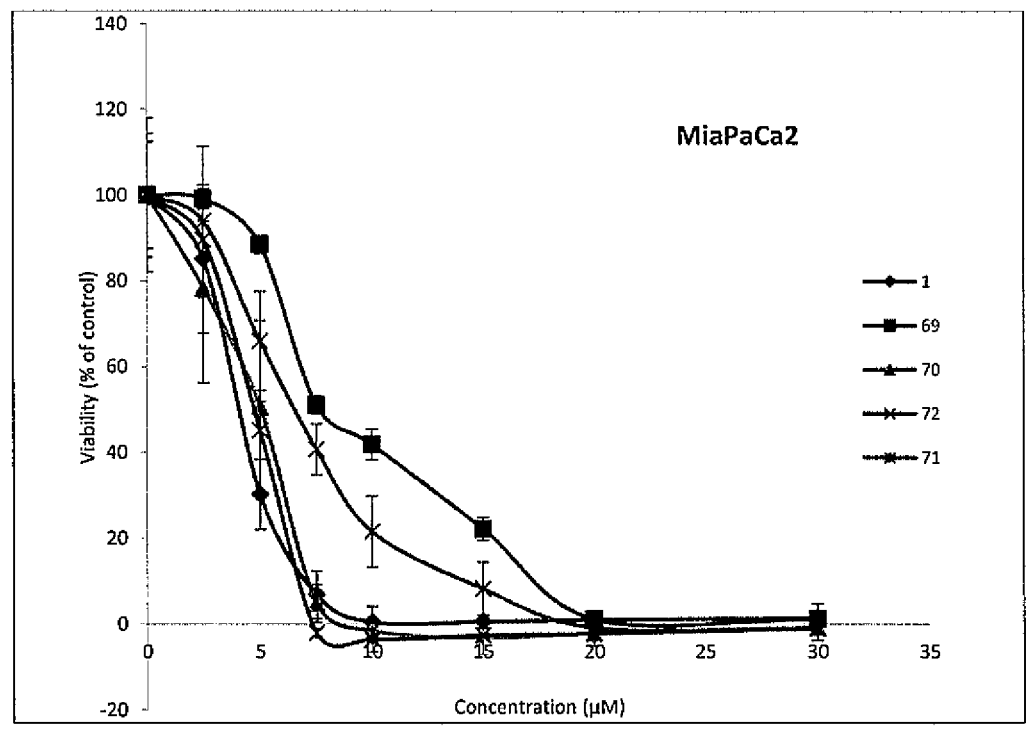
Figure 2J:
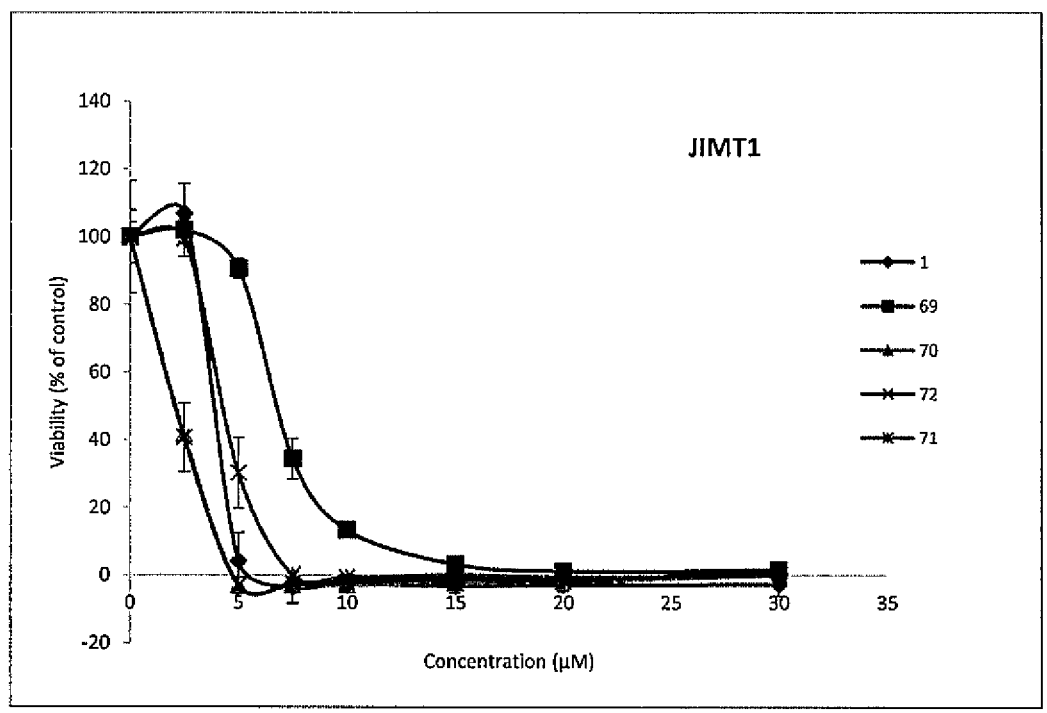
Figure 2K:
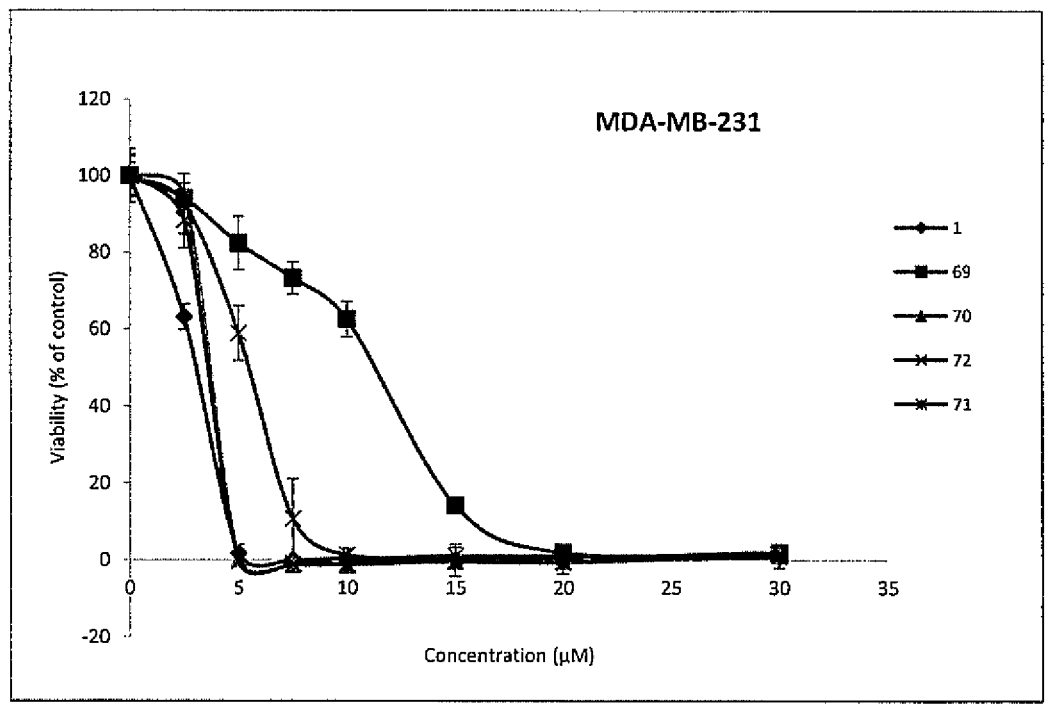
Figure 2L:
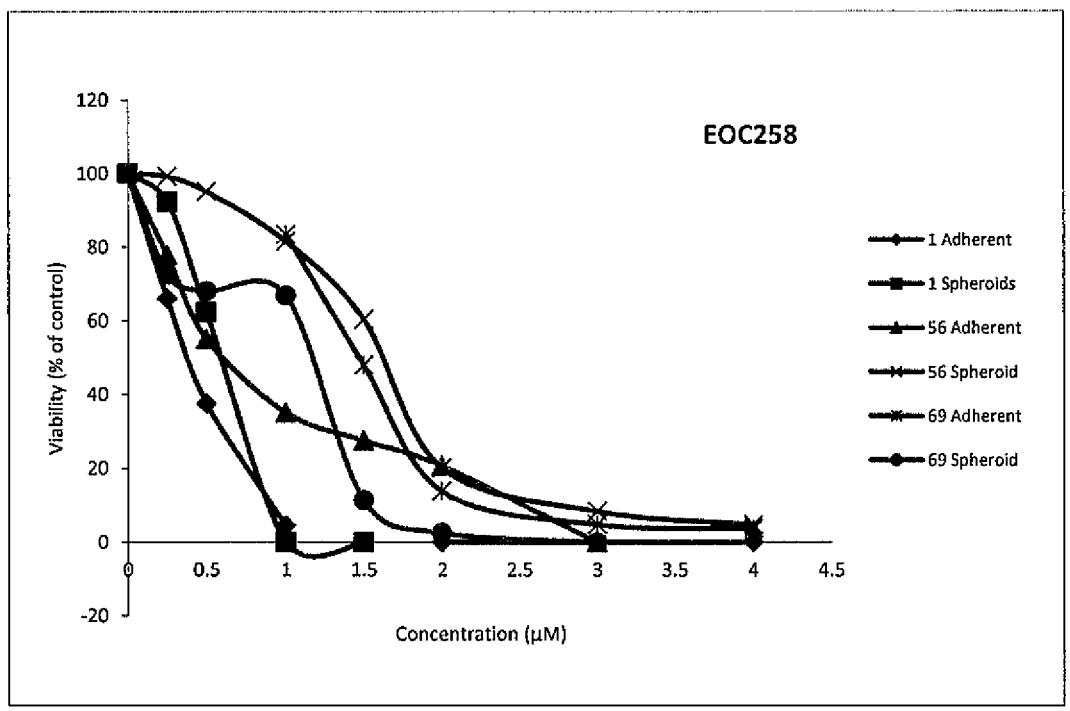
Figure 2M:
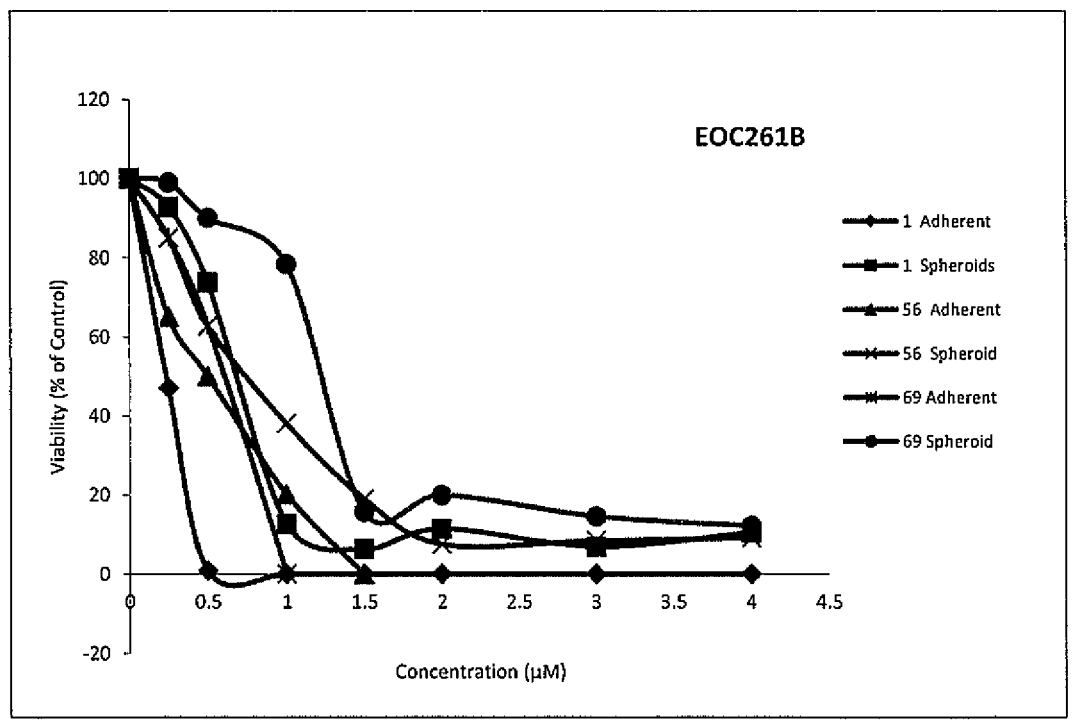
Figure 2N:
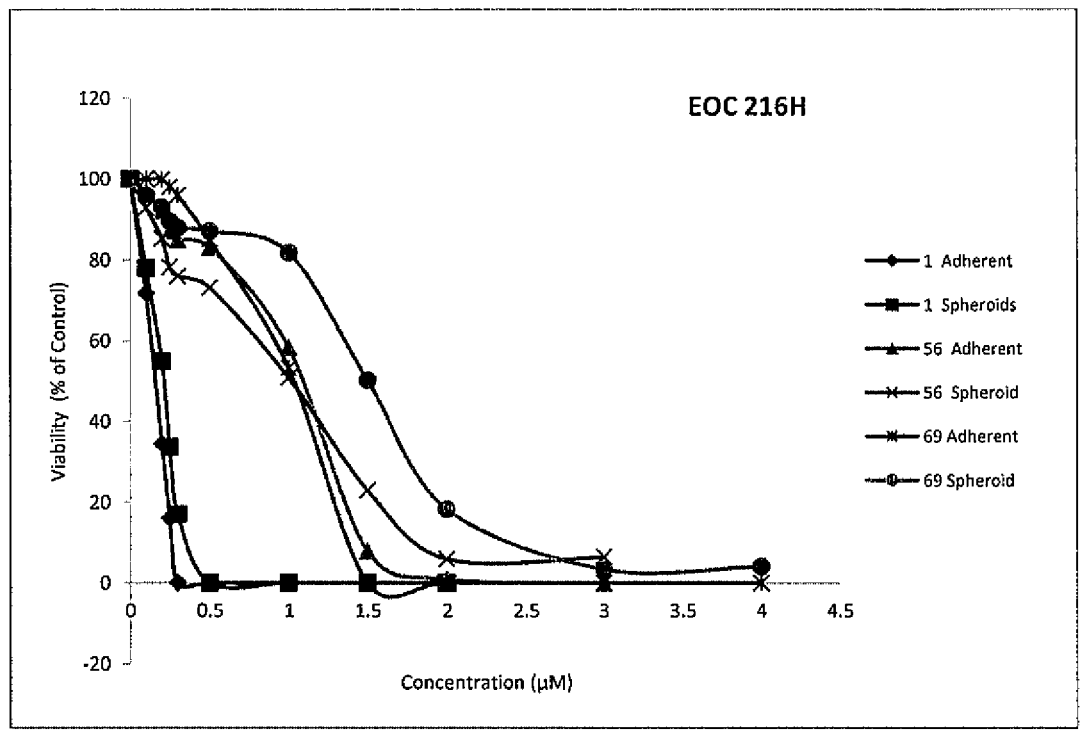
Figure 2O:
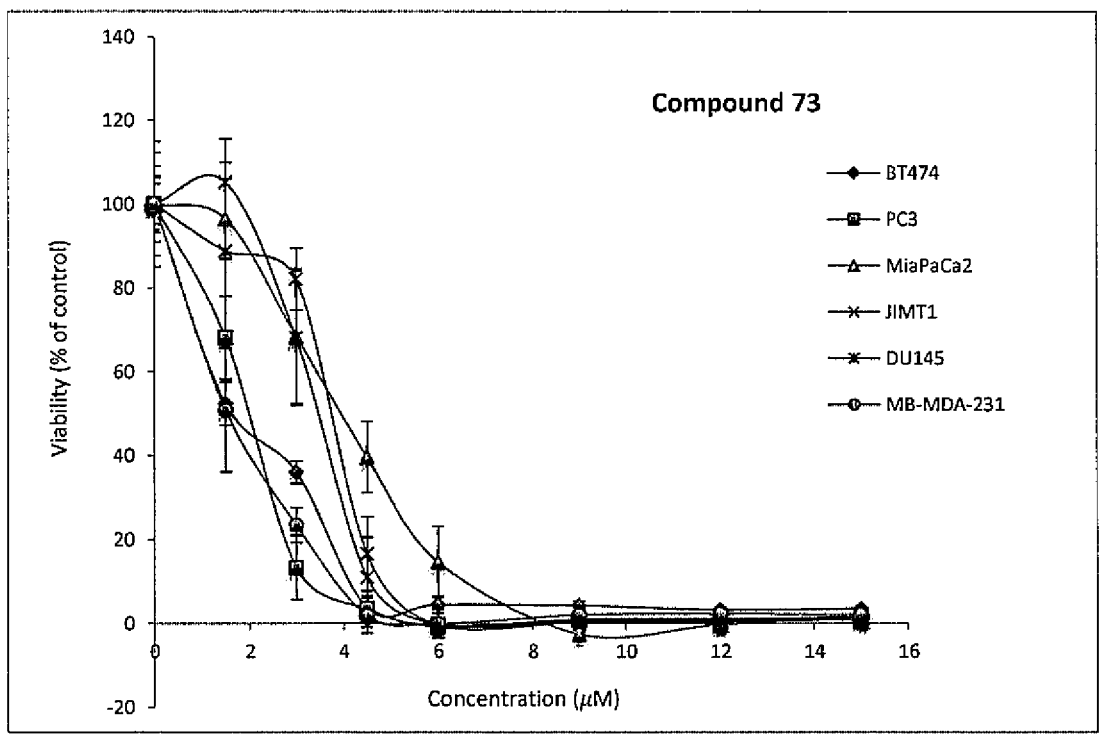

Tricationic GAELs, compound 73 and 75 were cytotoxic against all cell lines examined (FIG. 2O, Table 6). Compound 73 had $CC_{50}$'s of 1.5-4 µM. 2.3.2. Effect of GAELs with L sugars (56, 69, 70, 71, 72).

The rhamnose derived GAEL compound 56 killed 50% of the cancer cells in the range of 4.8-11.0 µM across all the cell lines tested and the $CC_{90}$ values were in the range 6.5 to 14 µM. These values are significantly lower than the corresponding values for the reference drug Gln 11 (see Table 2).

For the L-Gln 69, we observed activity and $CC_{50}$ in the range of 6.5 to 12.5 µM. Except for DU-145, compound 69 appears to be significantly more active than Gln 11 against other cell lines tested (see Table 2). This is really expected because the sample we tested is about 90% α-anomer because previous studies showed that for Gln 11 with the D-sugar, the α-anomer was about 1.5 to 2 times more active than corresponding β-anomers. GAELs bearing dicationic L sugars were synthesized and shown to be as active as D-sugar GAELS (Table 5). The most active compounds were those bearing a phenyl group (FIGS. 2H-2K). No differences were observed with the alpha or beta anomeric forms of these compounds.

The activities observed with these L-sugar derived GAELs confirmed our hypothesis that use of a sugar unnatural to humans will show activity, as discussed above.

Figures 1, 2, 3:
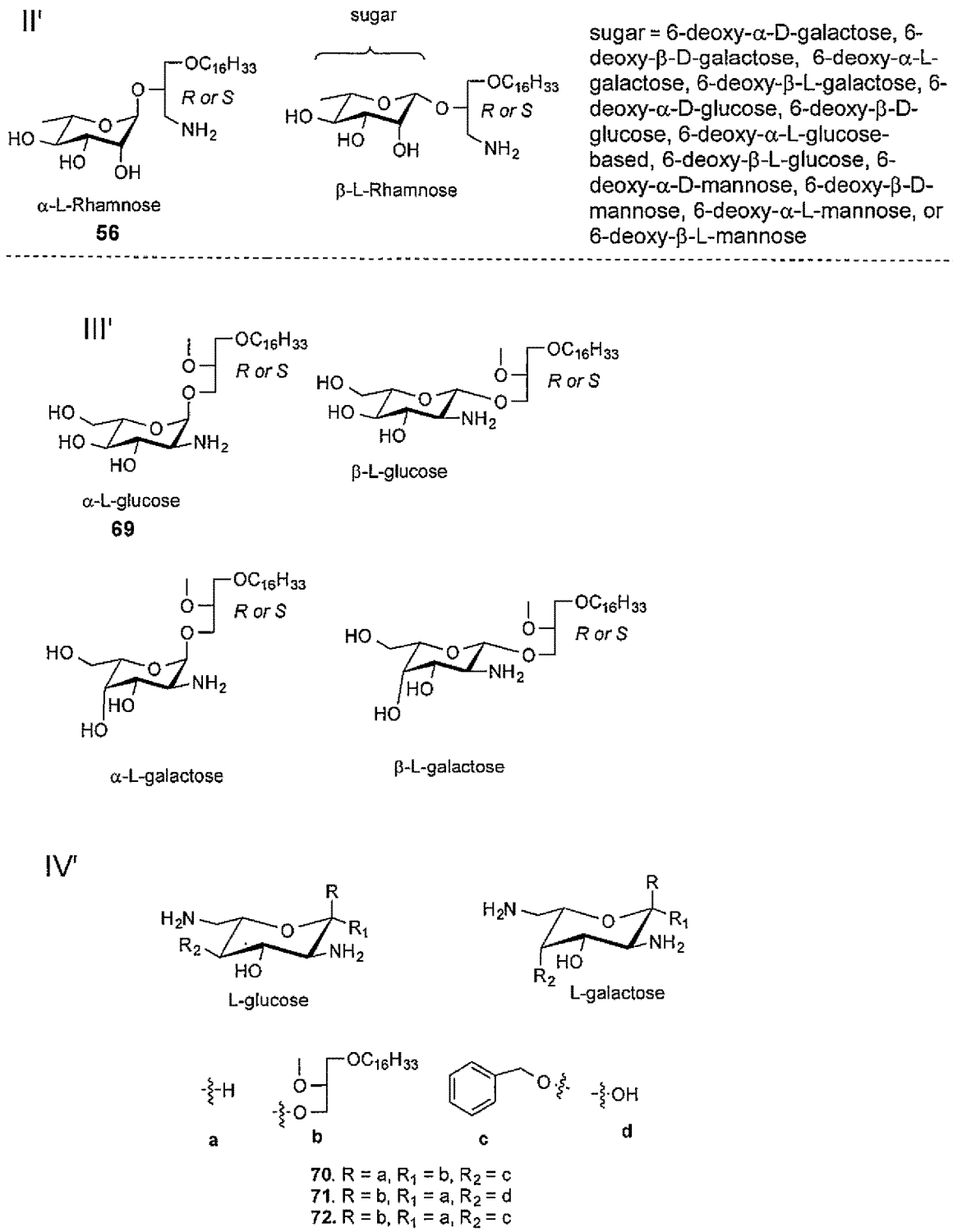

2.4 Effect 1-10 and 56 and 69 on the Integrity and Viability of Cancer Stem Spheroids The results of our studies revealed that the dicationic and L-sugar derived GAELs effectively caused the disintegration of BT474, DU145 and A2780 cancer stem cell spheroids (FIG. 3). Analysis of the viability of the cells at the end of the incubation period revealed that incubating with between 5-10 µM was sufficient to completely inhibit the viability of the CSCs (FIGS. 3A-3C).

2,5. Tolerability/Toxicity of 56 (Rhamnose GAEL).

The toxicity of 56 administered intravenously or orally to female Rag2M mice was established. Toxicity of the mice was assessed by monitoring the behaviour, body weight and assessment of the major tissues following necropsy. No toxicity was observed in mice administered 300 mg/kg of 56 orally (the highest concentration tested). Intravenous delivery of up to 50 mg/kg of 56 did not result in any observed abnormalities in behaviour or loss of body weight. Necropsy did not reveal any abnormalities in the tissues.

4.1. Materials and Methods: Synthesis of GAELs

Solvents were dried over $CaH_2$. $^1H$, $^{13}C$ NMR spectra were recorded with a JMN A500 FT NMR spectrometer at 500 or 300 MHz and at 126 or 75 MHz, respectively, and chemical shifts were reported in parts per million (ppm). Optical rotations were measured with a Jasco P-1020 digital polarimeter. Thin-layer chromatography (TLC) was carried out on aluminum-backed silica gel GF plates (250 mm thickness) and plates were visualized by charring with 10% $H_2SO_4$ in EtOH and/or short wavelength UV light. Compounds were purified by flash chromatography on silica gel 60 (230-400 ASTM mesh). Matrix assisted laser desorption/ionization-time of flight (MALDI-TOF)-MS was recorded on a Persptive Voyager RP mass spectrometer. High-resolution (HR) mass spectra were recorded on a JEOL JMS700 under FAB conditions. Purity of compounds 1-10 was assessed by elemental analysis of elements (C, H, N) and were within ±0.5% of the theoretical values.

4.2. Chemistry: General Methods

General Method for Acetylation

Acetylation reactions were carried out in pyridine with dimethyl amino pyridine (DMAP), 0.2 equivalent, as the catalyst using acetic anhydride (2 equivalents). After stirring for 18 hrs at room temperature, the reaction was stopped by addition of methanol (10 ml), and then concentrated to dryness. The resulting residue was dissolved in ethyl acetate and washed with saturated sodium bicarbonate (3 times) and distilled water (2 times). The resulting organic layer was dried over $Na_2SO_4$ and concentrated to dryness. The residue was purified by flash chromatography.

General Method for Glycosylation Reaction

The glycoside donor and 1.1 equivalent of the lipid alcohol, the glycoside acceptor, were dissolved in anhydrous dichloromethane (DCM) under argon atmosphere. N-Iodosuccinimide (NIS), 1.5 equivalents of the glycoside donor and silver triflate AgOTf, 0.2 equivalent were simultaneously added. The reaction mixture was left under vigorous stirring for 3 hrs. At the completion of reaction (TLC monitoring), the reaction mixture was diluted by DCM (20 ml) and then filtered over Celite. The resulting organic layer was washed with saturated sodium thiosulphate solution (2 times), saturated sodium bicarbonate (3 times) and water (2 times). The organic layer was the dried over anhydrous $Na_2SO_4$ and then concentrated under vacuum to give a brownish gel residue. The residue was then purified by flash chromatography (Hexane/Ethyl acetate, 4:6).

General Method for Conversion of Primary Hydroxyl Group to Azide

Triisopropylbenzylsulphonylchloride (TIBS) or p-toluenesulphonyl chloride were used to activate the hydroxyl group using DMAP as catalyst in anhydrous pyridine under argon or Nitrogen atmosphere. The reaction was stirred vigorously at room temperature for 12-24 hrs after which it was stopped by addition of methanol (10 ml) and then stirred vigorously for 10 minutes. The methanol and pyridine were removed under high vacuum. The crude mixture was dissolved in EtOAc and washed with 5% HCl (2 times), then saturated sodium bicarbonate solution (2 times) and water (once) to give a dark brown organic layer. The organic solvent was removed under vacuum and crude residue was purified by flash chromatography EtOAc/Hexane, (4:6) or 100% ethyl acetate depending on the compound. The sulphonate ester was replaced with azide in a nucleophilic substitution reaction using sodium azide (10 equivalents) in anhydrous DMF at 70-90° C. under argon or nitrogen atmosphere for 12-24 hrs. At the end of the reaction, the solvent DMF was removed under high vacuum. The residue was resuspended in ethyl acetate and then filtered to remove excess sodium azide. The solvent was removed under vacuum and the residue was purified using flash chromatography.

General Method for Deprotection of Acetate Group

The acetate protected compound was dispersed in methanol followed by addition of NaOMe (0.5 equivalent). The mixture was vigorously stirred for 1 hr and at the completion of the reaction was added ion exchange resin (H$^+$). When the reaction mixture was clear, the resin was filtered and then concentrated under vacuum. The residue was purified by flash chromatography (100% ethyl acetate). For selective deprotection of acetate in the presence of phthalimido protective group, only catalytic amount of sodium methoxide was used and the solution was stirred for 20-40 minutes.

General Method for Simultaneous Deprotection of Acetate and Phthalimido Group

To simultaneously remove acetate and phthalimido protecting group, the protected compound is dissolved in a mixture of ethylenediamine/n-butanol (1:1), the the solution is heated to 90° C., under vigorous stirring for 2 hrs. Then the reaction mixture is concentrated under high vacuum and then purified using C$_{18}$ coated silica gel column by gradient elution (100% water/0% methanol to 0% water/100% methanol).

General Method for Reduction of Azide

To reduce the azido protecting group free amine, the azide was suspended in a mixture of THF/water (9:1), then trimethyl phosphine in THF (1M) was added (5 to 10 equivalent of trimethyl phosphine). The reaction mixture was stirred at room temperature for 2 hrs, then it was concentrated under vacuum. The residues especially in case of final compounds were purified using C$_{18}$ coated silica gel column chromatography by gradient elution (100% water/0% methanol to 0% water/100% methanol). For lipid molecule with azido group the purification were carried using normal phase flash chromatography by hexane/ethylacetate mixture (9:1) and 100% ethyl acetate for protected glycolipid.

1,3,4,6-tetra-O-acetyl-2-azido-2-deoxy-α/β-D-glucopyranose (15)

D-glucosamine hydrochloride 14 (3 g, 13.92 mmol) was dissolved in water (15). To the solution was added Et$_3$N (2.8 g, 27.8 mmol) and CUSO$_4$.5H$_2$O (36 mg, 0.015 mmol). Triflicazide (16 mmol) prepared as previously described by Xu, Y. et al., Chem Med Chem 2013, 8, 511-520) was then added to the reaction mixture. The blue mixture was stirred vigorously for 18 hrs and then concentrated under vacuum at room temperature. The residue was dissolved in pyridine (30 ml) and DMAP (150 mg, 1.2 mmol) was added followed by addition of acetic anhydride (9 ml, 96 mmol). After stirring for 18 hrs at room temperature, the reaction was stopped by addition of methanol (10 ml), and then concentrated to dryness. The resulting residue was dissolved in ethyl acetate (120 ml) and washed with saturated sodium bicarbonate (3 times) and distilled water (2 times). The resulting organic layer was dried over Na$_2$SO$_4$ and concentrated to dryness. The residue was purified by flash chromatography (Hexane:EtOAc, 6:4) to yield 15 as an off white solid (4.5 g, 85%). The NMR data was in agreement with previously reported data (Xu, Y. et al., 2013). ES-MS: calcd C$_{14}$H$_{19}$N$_3$O$_9$Na$^+$ m/z: 396.1, found: [M+Na]$^+$ m/z: 396.2.

Phenyl 3,4,6-tri-O-acetyl-2-azido-2-deoxy-1-thio-α/β-D-glucopyranose (16)

To a solution of 15 (4.5 g, 12.1 mmol) in of DCM (60 ml) at room temperature was added thiophenol (2.4 ml 24 mmol) and BF$_3$. Et$_2$O (3 ml, 24 mmol). After stirring overnight at room temperature the reaction was stopped with saturated sodium bicarbonate solution, the separated organic layer was then washed with saturated sodium bicarbonate solution (3 times), distilled water (2 times) and the organic layer was dried over Na$_2$SO$_4$ and then concentrated to dryness The residue was purified by flash chromatography (Hexane: EtOAc, 6:4) to afford 16 as a brownish white solid. α/β (4/1) mixture (3.9 g, 76%). The NMR data was in agreement with previously reported data (Xu, Y. et al., Chem Med Chem 2013, 8, 511-520). ES-MS: calcd C$_{18}$H$_{21}$N$_3$O$_7$SNa$^+$ m/z: 446.1, found [M+Na]$^+$ m/z: 446.3.

Phenyl-2-azido-2-deoxy-1-thio-α/β-D-glucopyranose (17)

To a dispersion of 16 (3.9 g) in methanol was added NaOMe (1 g). The mixture was vigorously stirred for 1 hr and at the completion of the reaction was added about 1 g of ion exchange resin (H$^+$). When the reaction mixture was clear, the resin was filtered and then concentrated under vacuum. The residue was purified by flash chromatography (100% ethyl acetate) to give 17 as an off-white solid. α/β (3/1) mixture (2 g, %). Characteristic proton NMR data: $^1$H NMR (300 MHz, Chloroform-d) δ 5.53 (d, J=4.4 Hz, 0.75H, α H-1), 4.54 (d, J=10.2 Hz, 0.25H, β H-1). ES-MS: calcd C$_{12}$H$_{15}$N$_3$O$_4$SNa$^+$ m/z: 320.1, found [M+Na]$^+$ m/z: 320.3.

Phenyl-2-azido-2-deoxy-1-thio-6-O-(-2,4,6-triisopropylbenzylsulphonyl-α/β-D-glucopyranose (18)

Compound 17 (3.2 g, 10.76 mmole), triisopropylbenzylsulphonylchloride (TIBS) and DMAP were added together in a 100 ml flask cooled to 0° C. under vacuum for 20-30 minutes, after which the vacuum atmosphere was replaced with nitrogen atmosphere. 50 ml of dry pyridine was added via septum to ensure dry condition. The reaction was stirred vigorously at room temperature for 24 hrs after which it was stopped by addition of methanol (10 ml) and then stirred vigorously for 10 minutes. The methanol and pyridine were removed under high vacuum. The crude mixture was dissolved in EtOAc and washed with 5% HCl (2 times) then saturated sodium bicarbonate solution (2 times) and water (once) to give a dark brown organic layer. The organic solvent was removed under vacuum and crude residue was purified by flash chromatography (EtOAc/Hexane, 4:6) to give 18 as brown foam (2.5 g, 4.43 mmol). Yield 41%). Characteristic proton NMR data: $^1$H NMR (300 MHz, Chloroform-d) δ 7.60-7.37 (m, 2H, TIBS aromatic proton), 7.32-7.16 (m, 5H, thiophenyl proton), 5.53 (d, J=4.3 Hz, 0.48H, α H-1), 4.44 (d, J=9.1 Hz, 0.52H, β H-1), 1.37-1.14 (m, 18H, TIBS Isopropyl —CH$_3$). ES-MS: calcd C$_{27}$H$_{37}$N$_3$O$_6$S$_2$Na$^+$ m/z: 586.2, found [M+Na]$^+$ m/z: 586.4.

Phenyl-2, 6-diazido-2, 6-dideoxy-1-thio-α/β-D-glucopyranose (19)

Compound 18 (2.5 g, 4.43 mmol) was dissolved in anhydrous DMF (25 ml) under Nitrogen gas atmosphere, then NaN$_3$ (2.3 g, 35.44 mmol) was added and the reaction mixture was heated to 70° C. with vigorous stirring overnight (18 hrs). The DMF was removed under high vacuum and the residue was suspended in ethyl acetate and then filtered to remove excess sodium azide. The organic layer was then concentrated under vacuum and the purified by flash chromatography (100% EtOAc) to give 19 as a brownish gel (1.36 g, 4.4 mmol). Yield 99%. Characteristic proton NMR data: $^1$H NMR (300 MHz, Chloroform-d) δ 7.67-7.19 (m, 5H, thiophenyl aromatic protons), 5.64 (d, J=4.8 Hz, 0.55H, αH-1), 4.51 (d, J=9.9 Hz, 0.45H, βH-1). ES-MS: calcd $C_{12}H_{14}N_6O_3SNa^+$ m/z: 345.1, found [M+Na]$^+$ m/z: 345.5.

Phenyl-3,4-diacetyl-2, 6-diazido-2, 6-dideoxy-1-thio-α/β-D-glucopyranose (20)

To a solution of compound 19 (1.36 g, 4.4 mmol) in pyridine (25 ml) was added a catalytic amount of DMAP (100 mg, mmol) and acetic anhydride (5 ml). The solution was stirred vigorously overnight at room temperature. At the completion of the reaction, excess acetic anhydride was quenched by addition of methanol (5 ml). The solvents, methanol and pyridine were removed under high vacuum to give a brownish residue. The residue was dissolved in DCM and then washed with 5% HCl solution (2 times), saturated sodium bicarbonate (3 times) and distilled water (2 times). The organic layer was dried over anhydrous $Na_2SO_4$ and then concentrated under vacuum to a give a brown gel residue. The residue was the purified by flash chromatography (Hexane/Ethyl acetate, 4:6) to give compound 20 as a brown gel (1.5 g, 4.40 mmol), yield 100%. Characteristic proton NMR data: $^1$H NMR (300 MHz, Chloroform-d) δ 7.65-–7.24 (m, 15H, thiophenyl aromatic protons), 5.66 (d, J=5.6 Hz, 0.46H, αH-1), 4.51 (d, J=10.2 Hz, 0.54H), 2.13-1.99 (m, 6H, acetate —CH$_3$). ES-MS: calcd $C_{16}H_{18}N_6O_5SNa^+$ m/z: 429.10 found [M+Na]$^+$ m/z: 429.1.

1-O-Hexadecyl-2-O-methyl-3-O-(3', 4'-O-diacetyl-2', 6'-diazido-2', 6'-dideoxy-α-D-glucopyranosyl)-sn-glycerol (22)

Compound 20 (161 mg, 0.4 mmol) and compound 21 (168 mg, 0.48 mmol) were dissolved in anhydrous DCM (10 ml) under argon atmosphere. NIS (180 mg, 0.8 mmol) and silver triflate (20 mg, 0.08 mmol) were added. The reaction mixture was left under vigorous stirring for 3 hrs. At the completion of reaction (TLC monitoring), the reaction mixture was diluted by DCM (20 ml) and then filtered over Celite. The resulting organic layer was washed with saturated sodium thiosulphate solution (2 times), saturated sodium bicarbonate (3 times) and water (2 times). The organic layer was then dried over anhydrous $Na_2SO_4$ and then concentrated under vacuum to give a brownish gel residue. The residue was then purified by flash chromatography ((Hexane/Ethyl acetate, 4:6)) to isolate compound 22 as a brown gel from the mixture of compounds 22 and 23. NMR data for compound 22: $^1$H NMR (300 MHz, Chloroform-d) δ 5.52-5.43 (m, 1H, H-3), 5.06 (d, J=3.5 Hz, 1H, αH-1), 5.00 (dd, J=10.2, 9.1 Hz, 1H, H-4), 4.07 (dt, J=10.2, 4.4 Hz, 1H), 3.91 (dd, J=9.7, 2.5 Hz, 1H), 3.69-3.51 (m, 5H), 3.48 (s, 3H, —OCH$_3$), 3.47-3.35 (m, 1H), 3.29 (m, 3H, H-2, H-6), 2.09 (s, 3H, Acetate CH$_3$), 2.05 (s, 3H, Acetate CH$_3$), 1.58 (m, 2H), 1.26 (s, 26H, Lipid tail), 0.89 (t, J=6.6 Hz, 3H, lipid terminal —CH$_3$). $^{13}$C NMR (75 MHz, CDCl3) δ 170.13, 170.01, 98.04, 79.11, 71.86, 70.10, 69.72, 69.46, 68.90, 67.91, 60.90, 57.96, 50.96, 31.93, 29.70, 29.36, 26.11, 22.69, 20.62, 14.11. ES-MS: calcd $C_{30}H_{54}N_6O_8Na^+$ m/z: 649.4, found [M+Na]$^+$ m/z: 649.4.

1-O-Hexadecyl-2-O-methyl-3-O-(2',6'-diazido-2',6'-dideoxy-α-D-glucopyranosyl)-sn-glycerol (24)

$^1$H NMR (300 MHz, Chloroform-d) δ 4.98 (d, J=3.5 Hz, 1H, H-1), 4.00 (dd, J=10.4, 8.6 Hz, 1H, H-3), 3.94-3.78 (m, 3H), 3.64-3.53 (m, 5H), 3.52-3.41 (m, 8H), 3.18 (dd, J=10.3, 3.5 Hz, 1H, H-2), 1.58 (m, 2H), 1.27 (s, 26H, lipid tail), 0.89 (t, J=6.6 Hz, 3H, lipid terminal —CH$_3$). $^{13}$C NMR (75 MHz, CDCl3) δ98.21, 79.24, 71.90, 71.72, 71.39, 70.90, 69.67, 67.18, 62.82, 57.91, 51.36, 31.94, 29.72, 29.67, 29.64, 29.62, 29.52, 29.37, 26.10, 22.70, 14.12. ES-MS: calcd $C_{26}H_{50}N_6O_6Na^+$ m/z: 565.4 found [M+Na]$^+$ m/z: 565.3.

1-O-Hexadecyl-2-O-methyl-3-O-(2',6'-diamino-2',6'-dideoxy-α-D-glucopyranosyl)-sn-glycerol (1)

$^1$H NMR (300 MHz, Methanol-d4) δ4.8 (d, J=3.6 Hz, 1H, H-1), 3.85 (m, 1H), 3.66-3.40 (m, 11H), 3.18 (dd, J=9.3 Hz, 1H, H-4), 3.07-2.95 (m, 1H, H-6a), 2.77 (dd, J=13.4, 6.9 Hz, 1H, H-6b) 2.60 (dd, J=10.0, 3.6 Hz, 1H, H-2), 1.58 (q, J=7.0 Hz, 2H), 1.32 (s, 26H), 0.93 (t, J=6.5 Hz, 3H). $^{13}$C NMR (75 MHz, MeOD) δ100.82, 80.67, 76.13, 73.90, 73.50, 72.73, 71.24, 68.25, 58.21, 57.36, 43.78, 33.12, 30.83, 30.80, 30.64, 30.52, 27.30, 23.78, 14.50. MALDI-HRMS: calcd $C_{26}H_{54}N_2O_6Na^+$ m/z: 513. 3880, found [M+Na]$^+$ m/z: 513.3956.

1, 3, 4, 6-tetra-O-acetyl-2-deoxy-2-N-phthalimido-D-glucopyranoside (25)

Glucosamine hydrochloride 14 (3.016 g, 14 mmol) and NaOH (28 mmol) were dissolved in 50 ml of water. The resulting mixture was stirred at room temperature for 30 minutes. Phthalic anhydride (2.34 g, 157 mmol) was added to the solution. The mixture was stirred vigorously at room temperature for 18 hours. The mixture was concentrated and dried using rotary evaporator. The residue was dissolved in pyridine (30 mL), and then Ac$_2$O (19.8 mL) was added to the solution. The resulting solution was allowed to stir vigorously overnight. The reaction was checked by the TLC. Methanol (6 mL) was used to quench the excess of Ac$_2$O, and then excess pyridine was removed under high vacuum. The remaining solid was dissolved in CH$_2$Cl$_2$ (40 mL), and then the solution was washed with 10% HCl (40 ml×1), saturated NaHCO$_3$ solution (40 ml×3), H2O (40 ml×1) and brine (40 mL×1) and dried over anhydrous MgSO$_4$. The final solution was concentrated under reduced pressure, and the obtained product 25 (3.3 g, 49.4%) was dried overnight. NMR data were consistent with data in the literature (Xu, Y. et al., Chem Med Chem 2013, 8, 511-520).

Phenyl 3,4,6-tri-O-acetyl-2-N-phthalimido-2-deoxy-1-thio-β-D-glucopyranose (26)

To a solution of 25 (1.5 g, 3.16 mmol) in DCM (20 ml) at room temperature was added thiophenol (1.2 ml, 9.48 mmol) and BF$_3$. Et$_2$O (0.94 ml, 9.48 mmol). After stirring overnight at room temperature the reaction was stopped with saturated sodium bicarbonate solution, the separated organic layer was then washed with saturated sodium bicarbonate solution (3 times), distilled water (2 times) and the organic layer was dried over Na$_2$SO$_4$ and then concentrated to dryness. The residue was purified by flash chromatography (Hexane:EtOAc, 6:4) to afford 26 as a brownish white solid (1.3 g yield 77%). The NMR data was in agreement with previously reported data (Xu, Y. et al., Chem Med Chem 2013, 8, 511-520).

Phenyl-2-phthalimido-2-deoxy-1-thio-β-D-glucopyranose (27)

To a dispersion of 26 (1.3 g, 2.85 umol) in methanol was added NaOMe (150 mg). The mixture was vigorously stirred until complete dissolution of 26 (about 15 to 30 minutes) and at the completion of the reaction was added about 1 g of ion exchange resin (H⁺). When the reaction mixture was clear, the resin was filtered and then concentrated under vacuum. The residue was purified by flash chromatography (100% ethyl acetate) to give 27 as a white solid, yield 80%. NMR data for compound 27: $^1$H NMR (300 MHz, Methanol-d4) δ=8.04-7.74 (m, 4H, phthalimido aromatic protons)), 7.49-7.17 (m, 5H, thiophenyl aromatic protons), 5.61 (d, J=10.4, 1H, H-1), 4.28 (dd, J=10.2, 7.8, 1H, H-3), 4.08 (dd, J=10.4, 2H), 3.97 (dd, J=12.0, 2.0, 1H), 3.78 (dd, J=12.1, 5.1, 1H), 3.59-3.41 (m, 2H). $^{13}$C NMR (75 MHz, MeOD) δ=135.67, 134.47, 132.84, 130.00, 128.71, 124.49, 124.20, 85.49, 82.69, 73.87, 72.28, 62.86, 57.82. ES-MS: calcd $C_{20}H_{19}NO_6SNa^+$ m/z: 424.1, found [M+Na]⁺ m/z: 424.1.

Phenyl-2-N-phthalimido-2-deoxy-6-(O-toluenesulphonyl)-1-thio-β-D-glucopyranose (28)

To a solution of compound 27 (700 ring, 1.743 mmol) in anhydrous pyridine (15 ml) at 0° C. was added p-toluenesulphonyl chloride (398 mg, 2.092 mmol) and DMAP (50 mg) under nitrogen atmosphere. The reaction was warmed up to room temperature and left overnight, after which it was stopped by addition of methanol (5 ml). The solvent was then removed under high vacuum and the residue was purified by flash chromatography (Hexane/EtOAc, 9:1) to give 28 as a white foam (722 mg, 1.3 mmol), yield 74%. NMR data for compound 28: $^1$H NMR (300 MHz, Chloroform-d) δ=7.93-7.68 (m, 6H, aromatic protons), 7.44-7.13 (m, 7H, aromatic protons), 5.53 (d, J=10.3, 1H, H-1), 4.45-4.25 (m, 3H, H-3), 4.19-4.02 (m, 2H, H-2), 3.78-3.46 (m, 2H), 3.31 (br s, 1H, OH), 3.05 (br s, 1H, OH), 2.45 (s, 3H, toluene CH₃). $^{13}$C NMR (DEPT135) (75 MHz, CDCl3) δ=134.32, 132.61, 129.96, 128.87, 128.07, 83.51, 77.24, 72.62, 70.95, 68.58, 55.23, 21.69. ES-MS: calcd $C_{27}H_{25}NO_8S_2Na^+$ m/z: 578.1, found [M+Na]⁺ m/z: 578.2.

Phenyl-2-N-phthalimido-2-deoxy-6-azido-6-deoxy-1-thio-β-D-glucopyranose (29)

Compound 28 (2.8 g, 5.19 mmol) was dissolved in anhydrous DMF (25 ml) under nitrogen gas atmosphere, then NaN₃ (2.7 g, 41.53 mmol) was added and the reaction mixture was heated to 70° C. with vigorous stirring overnight (18 hrs). The DMF was removed under high vacuum and the residue was suspended in ethyl acetate and then filtered to remove excess sodium azide. The organic layer was then concentrated under vacuum and the residue was partially purified by flash chromatography (100% EtOAc) to give 29 as a brownish gel (1.99 g, 4.67 mmol yield 90%). Compound 29 was not characterized using NMR spectroscopy. ES-MS: calcd $C_{20}H_{18}N_4O_5SNa^+$ m/z: 449.1, found [M+Na]⁺ m/z: 449.1.

Phenyl 3,4-diacetyl-2-N-phthalimido-2-deoxy-6-azido-6-deoxy-1-thio-β-D-glucopyranose (30)

To a solution of compound 29 (1.5 g, 3.66 mmol) in pyridine (25 ml) was added a catalytic amount of DMAP (150 mg, mmol) and acetic anhydride (3 ml). The solution was stirred vigorously overnight at room temperature. At the completion of the reaction, excess acetic anhydride was quenched by addition of methanol (5 ml). The solvents, methanol and pyridine were removed under high vacuum to give a brownish residue. The residue was dissolved in DCM and then washed with 5% HCl solution (2 times), saturated sodium bicarbonate (3 times) and distilled water (2 times). The organic layer was dried over anhydrous Na₂SO₄ and the concentrated under vacuum to a give a brown gel residue. The residue was the purified by flash chromatography (Hexane/Ethyl acetate, 4:6) to give compound 30 as a light yellow solid (1.63 g, 3.2 mMol), yield 87.4%. Characteristic proton NMR data: $^1$H NMR (300 MHz, Chloroform-d) δ=7.80 (m, 4H, phthalimido aromatic protons), 7.49-7.18 (m, 5H, thiophenyl aromatic protons), 5.57 (d, J=10.2, 1H, H-1), 4.27 (ddd, J=10.0, 8.3, 5.8, 1H), 4.14 (dd, J=10.2, 1H, H-2), 3.66-3.55 (m, 2H, H-6a), 3.55-3.42 (m, 2H, H-6b), 3.37 (d, J=4.0, 1H), 3.30 (d, J=5.9, 1H). $^{13}$C NMR (75 MHz, CDCl3) δ=δ 170.13, 170.01, 134.41, 133.28, 128.95, 128.31, 123.54, 83.67, 78.59, 73.04, 72.23, 55.57, 51.59, 21.46, 20.87. Chemical Formula: ES-MS: calcd $C_{24}H_{22}N_4O_7SNa^+$533.1, found [M+Na]⁺ m/z: 533.1.

1-O-Hexadecyl-2-O-methyl-3-O-(3',4'-O-diacetyl-2'-N-phthalimido-6'-azido-2',6'-dideoxy-α-D-glucopyranosyl)-sn-glycerol (31)

$^1$H NMR (300 MHz, Chloroform-d) δ=7.81 (m, 4H, phthalimido aromatic protons), 5.86 (dd, J=10.8, 9.0, 1H, H-3), 5.40 (d, J=8.5, 1H, H-1), 5.06 (dd, J=10.1, 9.0, 1H, H-4), 4.33 (dd, J=10.8, 8.4, 1H, H-2), 3.98-3.83 (m, 2H), 3.63 (dd, J=10.7, 4.9, 1H), 3.52-3.41 (m, 2H), 3.38-3.08 (m, 8H), 2.06 (s, 3H, Acetate CH₃), 1.88 (s, 3H, Acetate CH₃), 1.66-1.58 (m, 2H), 1.27 (s, 26H, Lipid tail), 0.89 (t, J=6.6 Hz, 3H, lipid terminal —CH₃). $^{13}$C NMR (75 MHz, CDCl3) δ=170.11, 169.63, 134.25, 123.54, 98.47, 78.60, 73.61, 71.66, 70.41, 70.38, 69.82, 68.71, 57.59, 54.64, 51.23, 31.94, 29.71, 29.67, 29.61, 29.48, 29.37, 26.01, 22.70, 20.66, 20.48, 14.12. ES-MS: calcd $C_{38}H_{58}N_4O_{10}Na^+$ m/z: 753.4, found [M+Na]⁺ m/z: 753.5

1-O-Hexadecyl-2-O-methyl-3-O-(-2'-amino-6'-azido-2',6'-dideoxy-β-D-glucopyranosyl)-sn-glycerol (32)

$^1$H NMR (300 MHz, Methanol-d4) δ=4.29 (d, J=8.1, 1H, H-1), 3.95 (dd, J=10.5, 4.3, 1H), 3.71 (dd, J=10.5, 4.2, 1H), 3.64-3.51 (m, 4H), 3.51-3.38 (m, 7H), 3.29-3.20 (m, 2H, H-3), 2.70-2.55 (dd, J=8.1, 1H, H-2), 1.59-1.52 (m 2H), 1.32 (s, 26H, Lipid tail), 0.88 (t, J=6.6 Hz, 3H, lipid terminal —CH₃). $^{13}$C NMR (75 MHz, MeOD) δ=104.73, 80.48, 79.10, 77.41, 77.31, 72.65, 71.46, 69.44, 58.33, 58.04, 52.79, 33.10, 30.80, 30.61, 30.50, 2725, 23.76, 14.47. ES-MS: calcd $C_{26}H_{52}N_4O_6Na^+$ m/z: 539.4, found [M+Na]⁺ m/z: 539.4

1-O-Hexadecyl-2-O-methyl-3-O-(-2',6'-diamino-2',6'-dideoxy-β-D-glucopyranosyl)-sn-glycerol (2)

$^1$H NMR (300 MHz, Methanol-d4) δ=4.26 (d, J=8.0, 1H, H-1), 3.95 (dd, J=10.8, 4.6, 1H), 3.70 (dd, J=10.6, 4.2, 1H), 3.66-3.45 (m, 8H), 3.33-3.14 (m, 3H), 3.06 (dd, J=13.4, 2.7, 1H), 2.61 (dd, J=9.6, 8.0, 1H, H-2), 1.66-1.54 (m, 2H), 1.32 (s, 26H, lipid tail), 0.87 (t, J=6.6 Hz, lipid terminal —CH₃). $^{13}$C NMR (75 MHz, MeOD) δ=104.98, 80.58, 78.08, 77.51, 73.51, 72.68, 71.41, 69.74, 58.45, 58.17, 43.99, 33.12, 30.83, 30.79, 30.64, 30.52, 27.28, 23.78. MALDI-HRMS: calcd $C_{26}H_{54}N_2O_6Na^+$ m/z: 513. 3880, found [M+Na]⁺ m/z: 513.3612.

1-O-Hexadecyl-2-O-methyl-3-O-(-2'-N-phthalimido-6'-azido-2',6'-dideoxy-β-D-glucopyranosyl)-sn-glycerol (33)

$^1$H NMR (300 MHz, Chloroform-d) δ7.89-7.77 (m, 4H, phthalimido aromatic protons), 5.20 (d, J=8.3 Hz, 1H, H-1), 4.34 (dd, J=10.9, 8.5 Hz, 1H, H-3), 4.13 (dd, J=10.9, 8.3 Hz, 1H, H-2), 3.87 (dd, J=10, 7, 4.6 Hz, 1H, H-6a), 3.76-3.66 (m, 1H), 3.62-3.49 (m, 4H, H-4, H-5, H-6b), 3.49-3.39 (m, 2H), 3.33 (dq, J=9.9, 4.6, 4.2 Hz, 21-1), 3.26 (d, J=4.0 Hz, 1H), 3.23-3.07 (m, 5H), 1.45-1.36 (m, 2H), 1.26 (s, 26H, lipid tail), 0.90 (t, J=6.6 Hz, 3H lipid terminal —$CH_3$). $^{13}C$ NMR (75 MHz, $CDCl_3$) δ 168.40, 134.18, 131.70, 123.42, 98.68, 78.67, 77A6, 75.23, 72.78, 71.69, 69.95, 68.32, 57.56, 56.56, 51.48, 31.94, 29.72, 29.67, 29.62, 29.47, 29.38, 26.00, 22.70, 14.13. ES-MS: calcd $C_{34}H_{54}N_4O_8Na^+$ m/z: 669.4, found $[M+Na]^+$ m/z: 669.4.

1-O-Hexadecyl-2-O-methyl-3-O-(-2'-N-phthalimido-6'-amino-2',6'-dideoxy-δ-D-glucopyranosyl)-sn-glycerol (3)

$^1H$ NMR (300 MHz, Methanol-$d_4$) δ 8.03-7.61 (m, 4H), 5.20 (d, J=8.5 Hz, 1H, H-1), 4.33 (dd, J=10.7, 8.6 Hz, 1H, H-3), 4.00 (dd, J=10.7, 8.5 Hz, 1H, H-2), 3.87 (dd, J=11.0, 4.2 Hz, 1H), 3.72-3.55 (m, 2H), 3.43-3.26 (m, 17H), 3.26-3.07 (m, 6H, H-6a), 2.88 (dd, J=13.5, 7.5 Hz, 1H, H-6b),), 1.58-1.46 (m, 2H), 1.32 (s, 26H), 0.83 (t, J=6.8 Hz, 3H). $^{13}C$ NMR (75 MHz, $CDCl_3$) δ 168.40, 134.18, 131.70, 123.42, 98.68, 78.67, 77.46, 75.23, 72.78, 71.69, 69.95, 57.56, 56.56, 52.45, 51.48, 31.94, 29.72, 29.67, 29.62, 29.47, 29.38, 26.00, 22.70, 14.13. MALDI-HRMS: calcd: $C_{34}H_{56}N_2O_8Na^+$ m/z: 643.3934, found $[M+Na]^+$ m/z: 643.3857.

1-O-Hexadecyl-2-deoxy-3-O-(3',4'-O-diacetyl-2'-N-phthalimido-6'-azido-2',6'-dideoxy-β-D-glucopyranosyl)-sn-glycerol (35)

Compound 30 (0.4 mmol) and the previously reported lipid compound 34 (168 mg, 0.48 mmol) were dissolved in anhydrous DCM (10 ml) under argon atmosphere. NIS (180 mg, 0.8 mmol) and silver triflate (20 mg, 0.08 mmol) were added. The reaction mixture was left under vigorous stirring for 3 hrs. At the completion of reaction (TLC monitoring), the reaction mixture was diluted by DCM (20 ml) and then filtered over Celite. The resulting organic layer was washed with saturated sodium thiosulphate solution (2 times), saturated sodium bicarbonate (3 times) and water (2 times). The organic layer was then dried over anhydrous $Na_2SO_4$ and then concentrated under vacuum to give a brownish gel residue. The residue was then purified by flash chromatography (Hexane/Ethyl acetate, 4:6) to give compound 35 as a white solid. Yield 51%.

$^1H$ NMR (300 MHz, Chloroform-d) δ=7.85 (dd, J=5.5, 3.1, 2H, phthalimido aromatic protons), 7.73 (dd, J=5.5, 3.1, 2H, phthalimido aromatic protons), 5.79 (dd, J=10.8, 9.0, 1H, H-3), 5.38 (d, J=8.5 Hz, 1H, H-1), 5.05 (dd, J=10.1, 9.0, 1H, H-4), 4.30 (dd, J=10.8, 8.5, 1H, H-2), 3.96-3.81 (m, 2H), 3.63-3.52 (m, 1H), 3.43 (dt, J=13.6, 6.9, 1H), 3.28-3.16 (m, 3H), 3.15-2.99 (m, 2H), 2.03 (s, 3H, Acetate $CH_3$), 1.85 (s, 3H, Acetate $CH_3$), 1.76-1.58 (m, 2H), 1.26 (s, 26H, Lipid tail), 0.89 (t, J=6.6 Hz, 3H, lipid terminal —$CH_3$). $^{13}C$ NMR (75 MHz, CDCl3) δ=170.12, 169.62, 134.27, 123.57, 97.99, 73.60, 71.82, 71.00, 70.53, 70.37, 67.04, 66.96, 54.68, 51.24, 31.91, 29.73, 29.68, 29.59, 29.48, 29.34, 26.07, 22.67, 14.10. ES-MS: calcd: $C_{37}H_{56}N_4O_9Na^+$ m/z: 723.4, found $[M+Na]^+$ m/z: 723.5.

1-O-Hexadecyl-2-deoxy-3-O-(2'-amino-6'-azido-2',6'-dideoxy-β-D-glucopyranosyl)-sn-glycerol (36)

$^1H$ NMR (300 MHz, Methanol-d4) δ=4.28 (d, J=7.9, 1H, H-1), 3.98 (dd, J=9.6, 6.3, 1H), 3.67 (dt, J=9.4, 6.4, 1H), 3.55 (td, J=6.4, 3.0, 2H), 3.51-3.41 (m, 5H, H-6), 3.30-3.21 (m, 2H, H-3), 2.63 (dd, J=9.8, 7.9, 1H), 1.96-1.82 (m, 2H, —$OCH_2$—$CH_2$—$CH_2O$—), 1.66-1.57 (m, 2H), 1.32 (s, 26H, Lipid tail), 0.86 (t, J=6.7 Hz, 3H, lipid terminal —$CH_3$). $^{13}C$ NMR (75 MHz, MeOD) δ=104.54, 77.34, 72.72, 72.10, 68.77, 67.91, 58.37, 52.81, 33.12, 31.16, 30.82, 30.65, 30.52, 27.31, 23.78, 14.50. ES-MS: calcd: $C_{33}H_{52}N_4O_7Na^+$ m/z: 639.4, found $[M+Na]$ m/z: 639.4.

1-O-Hexadecyl-2-deoxy-3-O-(2'6'-diamino-2',6'-dideoxy-β-D-glucopyranosyl)-sn-glycerol (4)

$^1H$ NMR (300 MHz, Methanol-d4) δ=4.25 (d, J=8.0, 1H, H-1), 3.99-3.61 (m, 2H), 3.50-3.60 (m, J=6.3, 3.8, 3H), 3.45 (t, J=6.5, 3H), 3.31-3.14 (m, 2H, H-3), 3.06 (dd, J=13.4, 2.8, 1H, H-6a), 2.76 (dd, J=13.4, 7.0, 1H, H-6b), 2.59 (dd, J=9.5, 8.0, 1H, H-2), 1.96-1.82 (m, 2H, —$OCH_2$—$CH_2$—$CH_2O$—), 1.64-1.55 (m, 2H), 1.32 (s, 26H, Lipid tail), 0.85 (t, J=6.7 Hz, 3H, lipid terminal —$CH_3$). $^{13}C$ NMR (75 MHz, MeOD) δ=104.78, 78.00, 77.55, 73.57, 72.10, 68.70, 67.89, 58.50, 44.00, 33.11, 31.21, 30.82, 30.66, 30.51, 27.32, 23.77, 14.50. MALDI-HRMS: calcd $C_{25}H_{52}N_2O_5Na^+$ m/z: 483.3774, found $[M+Na]^+$ m/z: 483.3781.

1-O-Hexadecyloxy-,2S/R,3-di (-3,4-diacetyl-6'azido-2-N-phthalimido-2',6'-dideoxy-β-D-glucopyranosyl)-glycerol (38)

$^1H$ NMR (300 MHz, Chloroform-d) δ7.95-7.65 (m, 8H, phthalimido aromatic protons), 5.71 (td, J=10.4, 9.1 Hz, 2H, H-3a, H-3b), 5.53 (d, J=8.5 Hz, 1H, H-1a), 5.20 (d, J=8.4 Hz, 1H, H-1b), 5.02 (dd, J=10.1, 8.9 Hz, 1H), 4.94-4.81 (m, 1H), 4.28-4.15 m, 2H, H-2a), 3.97-3.67 (m, 4H), 3.67-3.28 (m, 6H, H-2b), 3.26-2.98 (m, 3H), 2.06 (s, 6H, Acetate $CH_3$), 1.86 (s, 3H, Acetate $CH_3$), 1.64 (s, 3H, Acetate $CH_3$) 1.66-1.57 (m, 2H), 1.28 (s, 26H, Lipid tail), 0.89 (t, J=6.7 Hz, 3H, lipid terminal —$CH_3$. $^{13}C$ NMR DEPT (75 MHz, $CDCl_3$) δ δ 134.30, 134.19, 123.81, 123.52, 96.74, 96.69, 76.57, 73.25, 72.90, 71.53, 70.40, 70.39, 70.36, 70.15, 70.14, 70.12, 69.77, 69.76, 54.68, 54.41, 51.22, 51.23, 51.09, 31.89, 31.85, 29.65, 25.97, 25.87, 21.71, 22.65, 21.47, 20.68, 20.43, 14.13. ES-MS: calcd: $C_{55}H_{72}N_8O_{17}Na^+$ m/z: 1139.5, found $[M+Na]^+$ m/z: 1139.4.

1-O-Hexadecyloxy-2S/R,3-di(-2'-amino-6'azido-2',6'-dideoxy-β-D-glucopyranosyl)-glycerol (39)

$^1H$ NMR (300 MHz, Methanol-$d_4$) δ 4.49 (d, J=8.0 Hz, 1H, H-1a), 4.33 (d, J=8.4, 1H, H-1b), 4.16-3.97 (m, 2H), 3.78 (dd, J=10.7, 5.5 Hz, 1H), 3.67 (dd, J=5.1, 2.7 Hz, 2H), 3.59-3.39 (m, 2H), 3.36-3.22 (m, 7H, H-3a, H3b), 2.75-2.54 (m, 2H, H-2a, H-2b), 1.60 m, 2H), 1.31 (s, 26H, Lipid tail), 0.93 (t, J=4.5 Hz, 3H, lipid terminal —$CH_3$). $^{13}C$ NMR (75 MHz, MeOD) δ 104.87, 104.28, 78.63, 77.23, 77.05, 72.64, 72.60, 72.52, 71.57, 70.72, 58.48, 58.35, 52.79, 33.10, 30.81, 30.65, 30.49, 27.31, 23.76, 14.47. ES-MS: calcd: $C_{31}H_{60}N_8O_9Na^+$ m/z: 711.4, found $[M+Na]^+$ m/z: 711.4.

1-O-Hexadecyloxy-2S/R, 3-di(-2',6'-diamino-2',6'-dideoxy-β-D-glucopyranosyl)-glycerol (5)

$^1H$ NMR (300 MHz, Methanol-d4) δ 4.44 (d, J=8.3 Hz, 1H, H-1a), 4.29 (d, J=8.4 Hz, 1H, H-1 b), 4.03 (d, J=14.5 Hz, 2H), 3.8-3.59 (m, 3H), 3.56-3.35 (m, 5H), 3.28-3.17 (m, 4H, H-3a, H-3b), 3.15-3.01 (m, 2H, H-6a", H-6b"), 2.81-2.69 (m, 2H, H-6a', H-6b'), 2.64-2.58 (m, 2H, H-2a, H-2b), 1.60 (s, 2H), 1.32 (s, 26H, Lipid tail), 0.92 (t, J=6.8 Hz, 3H, lipid terminal —CH$_3$). 13C NMR (75 MHz, MeOD) δ 103.58, 103.27, 77.43, 76.41, 76.38, 72.11, 72.03, 70.19, 70.13, 69.47, 69.45, 57.17, 57.14, 48.04, 42.55, 42.47, 42.44, 31.61, 29.42, 29.31, 29.19, 25.77, 19.91, 23.67, 21.21, 11.80. MALDI-HRMS: calcd: C$_{31}$H$_{64}$N$_4$O$_9$Na$^+$ m/z: 659.4571, found [M+Na]$^+$ m/z: 659.2064.

p-Toluene, 3-Hexadecyloxy-2R-hydroxyl propyl-1-sulphonate (41)

$^1$H NMR (300 MHz, Chloroform-d) δ 7.78 (d, J=8.2 Hz, 2H, aromatic protons), 7.33 (d, J=8.1 Hz, 2H, aromatic protons), 4.11-4.00 (m, 2H, MsO—CH$_2$), 3.99-3.89 (m, 1H, HO—CH), 3.46-3.31 (m, 4H), 2.80 (d, J=5.4 Hz, 1H, OH), 2.42 (s, 3H, mesylate —CH$_3$), 1.55-1.41 (m, 2H), 1.25 (s, 26H, Lipid tail), 0.87 (t, J=6.4 Hz, 3H, lipid terminal —CH$_3$). $^{13}$C NMR (75 MHz, CDCl$_3$) δ 144.90, 132.77, 129.88, 127.99, 71.73, 70.77, 70.56, 68.25, 31.93, 29.71, 29.68, 29.64, 29.61, 29.48, 29.37, 26.01, 22.68, 21.58, 14.11.

3-Hexadecyloxy-2R-hydroxyl propyl-1-azide (42)

$^1$H NMR (300 MHz, Chloroform-d) δ 3.88 (p, J=5.4 Hz, 1H, HO—CH), 3.48-3.34 (m, 4H), 3.31 (dd, J=5.5, 2.9 Hz, 2H, —CH$_2$N$_3$), 3.17 (s, 1H, OH), 1.55-1.41 (m, 2H), 1.25 (s, 26H, Lipid tail), 0.85 (t, J=6.6 Hz, 3H, terminal lipid —CH$_3$). $^{13}$C NMR (75 MHz, CDCl$_3$) δ 71.92, 71.71, 69.59, 53.54, 31.93, 29.71, 29.67, 29.61, 29.52, 29.47, 29.37, 26.05, 22.67, 14.03. ES-MS: calcd: C$_{19}$H$_{39}$N$_3$O$_2$Na$^+$ m/z: 364.3, found [M+Na]$^+$ m/z: 364.5.

1-O-Hexadecyloxy-2R-(-3',4',6'-triacetyl-2-N-phthalimido-2'-deoxy-α-D-glucopyranosyl)-3-azido glycerol (43)

$^1$H NMR (300 MHz, Chloroform-d) δ 7.97-7.63 (m, 4H, phthalimido aromatic protons), 5.80 (dd, J=10.7, 9.1 Hz, 1H, H-3), 5.53 (d, J=8.5 Hz, 1H, H-1), 5.16 (dd, J=10.7 Hz, 1H, H-4), 4.32 (ddd, J=12.1, 8.5, 5.4 Hz, 2H, H-2), 4.19 (dd, J=12.2, 2.5 Hz, 1H), 3.96-3.73 (m, 2H, H-5), 3.60 (dt, J=10.0, 4.8 Hz, 1H), 3.48-3.30 (m, 4H), 3.27-3.16 (m, 1H), 2.12 (s, 3H, acetate —CH$_3$), 2.04 (s, 3H, acetate —CH$_3$), 1.88 (s, 3H, acetate —CH$_3$), 1.48 (m, 2H), 1.09 (s, 26H, Lipid tail), 0.88 (t, J=6.6 Hz, 3H, Lipid terminal —CH$_3$). $^{13}$C NMR (75 MHz, CDCl$_3$) δ 170.58, 170.11, 169.47, 134.21, 131.56, 123.50, 98.61, 78.66, 71.96, 71.79, 70.74, 70.24, 69.03, 62.16, 54.64, 52.46, 31.93, 29.69, 29.66, 29.62, 29.58, 29.45, 29.36, 26.06, 22.69, 20.75, 20.63, 20.44, 14.11. ES-MS: calcd: C$_{39}$H$_{53}$N$_4$O$_{11}$Na$^+$ m/z: 781.4, found [M+Na]$^+$ m/z: 781.4.

1-O-Hexadecyloxy-2R-(2'-amino-2'-deoxy-β-D-glucopyranosyl)-3-azido glycerol (6)

$^1$H NMR (300 MHz, Methanol-d$_4$) δ 4.45 (d, J=8.0 Hz, 1H, H-1), 4.02 (ddt, J=9.1, 6.3, 3.0 Hz, 1H), 3.69 (ddd, J=16.6, 7.3, 3.6 Hz, 3H), 3.63-3.54 (m, 2H), 3.48 (dt, J=12.5, 6.3 Hz, 4H), 3.32-3.27 (m, J=8.4 Hz, 2H, H-3), 2.66 (dd, J=8.0, 6.8, 1H, H-2), 1.64-1.49 (m, 2H), 1.32 (s, 26H), 0.93 (t, J=7.1, Hz, 3H Lipid terminal CH$_3$). $^{13}$C NMR (75 MHz, MeOD) δ 104.02, 78.30, 78.13, 77.23, 72.70, 71.78, 71.70, 62.78, 61.56, 58.30, 53.17, 33.15, 30.87, 30.83, 30.76, 30.70, 30.66, 30.55, 27.30, 23.81, 20.97, 14.57. MALDI-HRMS: calcd: C$_{25}$H$_{50}$N$_4$O$_6$Na$^+$ m/z: 525.3628, found [M+Na]$^+$ m/z: 525.3064.

1-O-Hexadecyloxy-2R-(2'-amino-2'-deoxy-α-D-glucopyranosyl)-3-amino glycerol (7)

$^1$H NMR (300 MHz, Methanol-d$_4$) δ 4.40 (d, J=8.1 Hz, 1H, H-1), 3.93-3.82 (m, 1H, —O—CH), 3.70 (dt, J=15.3, 4.6 Hz, 3H), 3.60-3.41 (m, 4H), 3.36-3.22 (m, 2H, H-3), 2.97-2.71 (m, 2H, —CH$_2$NH$_2$), 2.63 (t, J=8.4 Hz, 1H, H-2), 1.58 (m, 2H), 1.32 (s, 26H), 0.87 (t, J=6.9 Hz, 3H). $^{13}$C NMR (75 MHz, MeOD) δ 104.46, 80.02, 78.22, 77.78, 72.70, 72.67, 71.78, 62.81, 58.45, 43.77, 33.11, 30.80, 30.66, 30.51, 27.31, 23.77, 14.49. MALDI-HRMS: calcd: C$_{25}$H$_{52}$N$_2$O$_6$Na$^+$ m/z: 499.3723, found [M+Na]$^+$ m/z: 499.2997.

2(R/S)-Azido-3-hexadecyloxy-1-propanol (44)

Diisopropylazodicarboxylate (DIAD; 3.2 ml, 15 mmol) was added to a solution of racemic mixture of 3-O-hexadecyl-sn-glycerol 37 (3.42 g, 13 mmol) in 180 ml of DCM at 0° C. After the mixture was stirred for 3 h under Nitrogen gas, Me$_2$SiN$_3$ was added. The mixture was stirred at the same temperature for 3 h, then at room temperature until glycerol 37 had reacted completely. The reaction mixture was concentrated to give a yellow residue which was dissolved in a minimal amount of DCM and passed through a pad of silica gel in a sintered glass funnel. The pad was rinsed with hexane/EtOAc (50:1) until the excess yellow DIAD began to elute. After concentration of the eluted silyloxyazide, the residue was dissolved in 30 ml THF and treated with a solution of (nBu)$_4$NF (1 M, 25 ml) in THF. The mixture was stirred for 3 hrs at room temperature and then was diluted with 250 ml Et$_2$O and washed with water (2 times) and brine (2 times). The organic layer was separated, dried over Na$_2$SO$_4$ and concentrated. The crude product was purified by column on silica gel with hexane/EtOAc (4:1) to give compound 44 as a colorless gel. The NMR data corresponds to what has been previously reported (Byun, H.-S. et al., Chem Med Chem, 2010, 5, 1045-1052)

1-O-Hexadecyloxy-2S/R-azido,3-(-3',4',6'-triacetyl-2-N-phthalimido-2'-deoxy-α-D-glucopyranosyl)-glycerol (45)

$^1$H NMR (300 MHz, Chloroform-d) δ 7.85-7.69 (m, 4H, phthalimido aromatic protons), 5.79 (ddd, J=10.7, 9.1, 4.7 Hz, 1H, H-3), 5.39 (dd, J=10.9, 8.5 Hz, 1H, H-1), 5.16 (ddd, J=10.2, 9.1, 3.7 Hz, 1H, H-4), 4.39-4.24 (m, 2H, H-2), 4.20-4.05 (m, 2H), 4.01-3.81 (m, 2H, H-5), 3.65-3.55 (m, 1H), 3.55-3.45 (m, 1H), 3.44-3.32 (m, 1H), 3.31-3.10 (m, 2H), 2.09 (s, 3H), 2.01 (s, 3H), 1.84 (s, 3H), 1.46-138 (m, 2H), 1.30 (s, 26H, Lipid tail), 0.85 (t, J=6.6 Hz, 3H, Terminal Lipid CH$_3$). $^{13}$C NMR (75 MHz, CDCl$_3$) δ 170.60, 170.06, 169.42, 134.27, 134.23, 131.47, 123.54, 98.56, 98.46, 71.96, 71.68, 71.61, 70.65, 70.59, 70.25, 69.94, 69.05, 68.91, 68.90, 61.93, 61.90, 60.54, 60.32, 59.90, 54.49, 31.90, 29.67, 29.63, 29.59, 29.55, 29.46, 29.39, 29.33, 25.90, 22.66, 20.98, 20.71, 20.58, 20.41, 14.18, 14.09. ES-MS: calcd: C$_{39}$H$_{58}$N$_4$O$_{11}$Na$^+$ m/z: 781.4, found [M+Na]$^+$ m/z: 781.4.

1-O-Hexadecyloxy-2S/R-amino-3-(-3',4',6'-triacetyl-2-N-phthalimido-2'-deoxy-α-D-glucopyranosyl)-glycerol (46)

$^1$H NMR (300 MHz, Chloroform-d) δ 7.97-7.63 (m, 4H, phthalimido aromatic protons), 5.79 (t, J=9.9 Hz, 1H, H-3), 5.35 (d, J=8.4 Hz, 1H, H-1), 5.16 (t, J=9.6 Hz, 1H, H-4), 4.37-4.29 (m, 1H, H-2), 4.22-4.08 (m, 1H), 3.92-3.77 (m, 2H, H-5), 3.75-3.59 (m, 1H), 3.48 (dd, J=9.6, 5.3 Hz, 1H), 3.40 (dd, J=9.6, 6.8 Hz, 1H), 3.26-3.06 (m, 3H), 3.06-2.94 (m, 1H, —CHNH$_2$), 2.25 (broad s, 2H, Amino protons), 2.10 (s, 3H), 2.02 (s, 3H), 1.85 (s, 3H), 1.49-1.34 (m, 2H), 1.23

(s, 26H, Lipid tail), 0.86 (t, J=6.4 Hz, 3H, Lipid terminal —CH$_3$). $^{13}$C NMR (75 MHz, CDCl$_3$) δ 170.67, 170.12, 169.47, 134.34, 131.37, 123.62, 98.58, 98.37, 72.64, 72.48, 72.32, 71.88, 71.42, 70.71, 69.01, 62.02, 58.10, 54.65, 50.66, 50.61, 31.90, 29.68, 29.64, 29.58, 29.52, 29.45, 29.34, 26.05, 22.67, 20.74, 20.61, 20.43, 18.40, 14.10. ES-MS: calcd: C$_{39}$H$_{60}$N$_2$O$_{11}$Na$^+$ m/z: 755.4, found [M+Na]$^+$ m/z: 755.4.

1-O-Hexadecyloxy-2S/R-amino-3-(-2'-amino-2'-deoxy-α-D-glucopyranosyl)-glycerol (8)

$^1$H NMR (300 MHz, Methanol-d$_4$) δ 4.70 (dd, J=8.3, 3.1 Hz, 1H, H-1), 4.19-4.02 (m, 1H), 4.01-3.87 (m, 2H), 3.79-3.73 (m, 1H), 3.72-3.61 (m, 3H), 3.65-3.57 (m, 1H, H-3), 3.57-3.48 (m, 2H), 3.49-3.32 (m, 2H, —CHNH$_2$), 2.96 (ddd, J=10.3, 8.4, 1.7 Hz, 1H, H-2), 1.71-1.55 (m, 2H), 1.33 (s, 26H, lipid tail), 0.92 (t, J=6.4 Hz, 3H, lipid terminal —CH$_3$). $^{13}$C NMR (75 MHz, MeOD) δ 100.58, 100.18, 78.63, 73.85, 72.93, 71.74, 71.65, 68.58, 68.43, 62.15, 62.10, 52.72, 52.69, 33.09, 30.80, 30.77, 30.64, 30.53, 30.48, 27.13, 23.75. MALDI-HRMS: calcd: C$_{25}$H$_{52}$N$_2$O$_6$Na$^+$ m/z: 499.3723, found [M+Na]$^+$ m/z: 499.3450.

1-O-Hexadecyloxy-2S/R—N-hexadecylacyl-3-(-3',4',6'-triacetyl-2-N-phthalimido-2'-deoxy-β-D-glucopyranosyl)-glycerol (48)

Compound 46 (0.18 mmol, 128 mg) was dissolved in 10 ml of anhydrous DMF, palmitic acid 47 (0.21 mmol, 54 mg) and the coupling agent TBTU (0.25 mmol, 81 mg) were simultaneously added under argon atmosphere. The reaction mixture was left to stir for 5 hrs at room temperature. After complete disappearance of 46, the reaction mixture was concentrated under vacuum and the residue obtained was purified by flash chromatography using hexane/EtOAc (4:1) to give compound 48 as a white compound (yield 60%). ES-MS: calcd: C$_{55}$H$_{90}$N$_2$O$_{12}$Na$^+$ m/z: 993.6, found [M+Na]$^+$ m/z: 993.4.

1-O-Hexadecyloxy-2S/R—N-hexadecylacyl-3-(-2'-amino-2'-deoxy-β-D-glucopyranosyl)-glycerol (9)

$^1$H NMR (300 MHz, Methanol-d$_4$) δ 4.59 (dd, J=8.3, 6.3 Hz, 1H, H-1R/S), 4.42-4.20 (m, 1H, H-4 R/S), 3.92 (dd, J=12.1, 4.3 Hz, 2H, H-6a R/S), 3.83-3.63 (m, 3H, H-6b R/S), 3.66-3.44 (m, 6H, H-3 R/S), 2.86 (ddd, J=12.7, 10.5, 8.3 Hz, 1H, H-2 R/S), 2.29-2.17 (m, 2H, —NHCO—CH$_2$), 1.71-1.51 (m, 4H), 1.33 (s, 50H, two lipid tails), 0.93 (t, J=6.2 Hz, 6H, terminal —CH$_3$ of the two lipid tails). $^{13}$C NMR (75 MHz, MeOD) δ 176.79, 100.75, 100.45, 78.56, 74.02, 72.49, 72.45, 71.81, 71.02, 70.71, 70.53, 62.32, 57.54, 55.16, 50.52, 50.39, 49.88, 37.29, 37.19, 33.11, 30.85, 30.81, 30.74, 30.59, 30.52, 30.30, 27.33, 27.13, 23.77, 14.48. MALDI-HRMS: calcd: C$_{41}$H$_{82}$N$_2$O$_7$Na$^+$ m/z: 737.6020, found [M+Na]$^+$ m/z: 737.3607s 1-O-Hexadecyloxy-2S/R—N-methylcarbamoyl-3-(-3',4',6'-triacetyl-2-N-phthalimido-2'-deoxy-β-D-glucopyranosyl)-glycerol (50)

To a solution of compound 46 (0.16 mmol, 114, mg) in DCM was added methylchloroformate 49 (0.311 mmol, 29.4 mg) and Et$_3$N (0.35 mmol, 35.5 mg) at 0° C. The mixture was stirred overnight and then concentrated under vacuum to give residue which was purified with by flash chromatography using hexane/EtOAc (3:2) to give the carbamate glycolipid 50 (80% yield) as a white solid (Byun et al 2010).

$^1$H NMR (300 MHz, Chloroform-d) δ 7.92-7.68 (m, 4H, phthalimido aromatic protons), 5.79 (dd, J=10.7, 9.1 Hz, 1H, H-3), 5.35 (d, J=8.4 Hz, 1H, H-1), 4.83 (d, J=7.4 Hz, 1H, Carbamate —NH), 4.42-4.23 (m, 2H), 4.17 (ddd, J=12.3, 3.9, 2.4 Hz, 1H), 3.85 (dddd, J=17.5, 13.1, 6.7, 3.2 Hz, 4H), 3.53 (s, 3H, Carbamate —CH$_3$), 3.30 (ddd, J=18.5, 8.1, 3.9 Hz, 2H), 3.11 (ddt, J=29.1, 9.3, 6.7 Hz, 2H), 2.11 (s, 3H), 2.02 (s, 3H), 1.85 (s, 3H), 1.45-1.34 (m, 2H), 1.27 (s, 26H, Lipid tail), 0.88 (t, J=6.4 Hz, 3H, Lipid terminal —CH$_3$). $^{13}$C NMR (75 MHz, CDCl$_3$) δ 170.69, 170.11, 169.47, 134.32, 134.28, 131.42, 123.62, 98.49, 98.39, 71.89, 71.39, 71.32, 70.67, 70.63, 68.95, 68.91, 68.76, 68.66, 61.98, 54.59, 31.91, 29.69, 29.64, 29.58, 29.45, 29.34, 26.00, 25.97, 22.67, 20.73, 20.61, 20.43, 14.11. ES-MS: calcd: C$_{41}$H$_{62}$N$_2$O$_{13}$Na$^+$ m/z: 813.4, found [M+Na]$^+$ m/z: 813.3.

1-O-Hexadecyloxy-2S/R—N-methylcarbamoyl-(-2'-amino-2'-deoxy-β-D-glucopyranosyl)-glycerol (10)

$^1$H NMR (300 MHz, Methanol-d$_4$) δ 4.26 (dd, J=8.1, 2.4 Hz, 1H, H-1), 4.00-3.89 (m, 2H), 3.87 (d, J=1.5 Hz, 1H), 3.71 (ddd, J=8.6, 4.8, 2.0 Hz, 2H), 3.66 (s, 3H, carbamate —CH$_3$), 5.55-3.44 (m 4H, H-3), 3.38-3.22 (m, 3H), 265-2.58 (m, 1H, H-2) 1.60-1.55 (m, 2H), 1.31 (s, 26H, lipid tail), 0.92 (t, J=6.8 Hz, 3H, lipid terminal —CH$_3$). $^{13}$C NMR (75 MHz, MeOD) δ 105.05, 104.71, 78.23, 77.57, 77.51, 72.44, 71.84, 71.74, 70.97, 70.60, 70.28, 62.80, 62.69, 58.36, 58.34, 52.56, 52.23, 33.11, 30.82, 30.79, 30.65, 30.59, 30.50, 27.27, 23.77, 14.49. MALDI-HRMS: calcd: C$_{27}$H$_{54}$N$_2$O$_8$Na$^+$ m/z: 557.3778, found [M+Na]$^+$ m/z: 557.3364.

1-O-Hexadecyloxy-2R-(-α-L-rhamnopyranosyl)-3-amino glycerol (56)

$^1$H NMR (300 MHz, Methanol-d$_4$) δ 4.65 (d, J=1.3, 1H, H-1), 3.65 (dd, J=1.3, 2.3 Hz, 1H), 3.54 (dp, J=10.5, 5.6, 5.0 Hz, 2H), 3.45 (dd, J=9.5, 3.4 Hz, 1H), 3.34 (h, J=4.7 Hz, 1H), 3.29-3.19 (m, 2H), 3.14 (d, J=21.0 Hz, 2H), 2.57 (qd, J=13.5, 5.4 Hz, 2H), 1.40-1.34 m, 2H), 1.08 (s, 29H, H-6, lipid tail), 0.69 (t, J=6.4 Hz, 3H, lipid terminal —CH$_3$). $^{13}$C NMR (75 MHz, MeOD) δ 101.91, 79.55, 73.98, 72.69, 72.66, 72.45, 72.39, 70.10, 43.50, 33.10, 30.81, 30.78, 30.66, 30.50, 27.33, 23.76, 18.08, 14.47. MALDI-HRMS: calcd: C$_{25}$H$_{51}$NO$_6$Na$^+$ m/z: 484.6738, found [M+Na]$^+$ m/z: 484.6365.

1-O-Hexadecyloxy-2R—O-methyl(2'amino-2'deoxy-α-L-glucopyranosyl)-3-amino glycerol (69)

$^1$H NMR (300 MHz, Methanol-d$_4$) δ 4.71 (d, J=3.6 Hz, 1H, H-1), 3.76-3.66 (m, 1H), 3.62 (dd, J=11.8, 5.3 Hz, 1H), 3.47 (dd, J=9.8, 6.9 Hz, 4H), 3.42-3.29 (m, 3H, H-3), 3.26-3.13 (m, 2H), 2.50 (dd, J=9.8, 3.5 Hz, 1H, H-2), 1.50-146 (m, 2H), 1.22 (s, 26H, lipid tail), 0.83 (t, J=6.5 Hz, 3H, lipid terminal CH$_3$). $^{13}$C NMR (75 MHz, MeOD) δ 100.59, 80.50, 76.34, 74.22, 72.70, 71.88, 71.41, 67.92, 62.68, 58.26, 57.28, 33.11, 30.82, 30.65, 30.51, 27.29, 23.77, 14.49. MALDI-HRMS: calcd: C$_{26}$H$_{53}$NO$_7$Na$^+$ m/z: 514.6998, found [M+Na]$^+$ m/z: 484.3300

Compound 89: A solution of 87 in dry DMF was treated with NaN$_3$ at 90° C. for 3 h. The mixture was then concentrated under vacuo, worked up with H$_2$O (×2) and brine (×1) successively and re-concentrated to give 88 in excellent yield. 88 was subsequently dissolved in dry DCM, treated with PCC (3 equiv.) and stirred at RT for 2 h. The reaction was monitored with TLC using $KMnO_4$ stain. The resulting mixture was filtered through a pad of silica and concentrated under low vacuo to give 89. The resulting compound was used immediately without further purification Compound 84a (n=11): A solution of 3 (0.45 g, 0.73 mmol) in dry DCM was treated with 89a (n=11) (0.17 g, 0.73 mmol) and stirred overnight at 0° C. to RT. Two drops of acetic acid and sodium borohydride, $NaBH_4$ (0.099 g, 2.19 mmol) in methanol were then added to the mixture and stirred further for 2 h at RT. The resulting mixture was concentrated in vacuo, extracted with ethyl acetate and purified by flash chromatography (dichloromethane/methanol, 10:1, v/v) to afford 84a (0.46 g, 73%). $^1$H NMR (500 MHz, MeOD): δ=7.92-7.78 (m, 4H), 5.21 (d, J=8.5 Hz, 1H, H-1), 4.32 (dd, J=10.8, 8.6 Hz, 1H, H-3), 4.00 (dd, J=10.8, 8.5 Hz, 1H, H-2), 3.84-3.72 (m, 1H), 3.63-3.53 (m, 1H), 3.50-3.38 (m, 3H), 3.30-3.23 (m, 5H), 3.23-3.09 (m, 6H), 3.07-3.01 (m, 2H), 1.87-1.80 (m, 2H), 1.73-1.66 (m, 2H), 1.50-1.17 (m, 44H), 0.89 (t, J=6.9 Hz, 3H). ESI-MS: m/z $[M+Na]^+$ calc'd for $C_{46}H_{79}N_5O_6Na^+$: 853.09, found: 853.1

Compound 84b (n=2): A solution of 3 (0.21 g, 0.34 mmol) in dry DCM was treated with 89b (n=2) (0.035 g, 0.34 mmol) and stirred overnight at 0° C. to RT. Two drops of acetic acid and sodium borohydride, $NaBH_4$ (0.005 g, 0.10 mmol) in methanol were then added to the mixture and stirred further for 2 h at RT. The resulting mixture was concentrated in vacuo, extracted with ethyl acetate and purified by flash chromatography (dichloromethane/methanol, 10:1, v/v) to afford 84b (0.17 g, 70%). 1H NMR (500 MHz, MeOD): δ=7.92-7.78 (m, 4H), δ 5.17 (d, J=8.0 Hz, 1H, H-1), 4.33 (dd, J=10.5, 4.9 Hz, 1H), 3.90 (dd, J=10.5, 3.9 Hz, 1H), 3.61-3.42 (m, 7H), 3.38 (t, J=6.7 Hz, 4H), 3.26 (dd, J=10.0, 8.7 Hz, 1H), 3.15-3.09 (m, 1H), 2.94 (dd, J=14.2, 2.4 Hz, 1H), 2.68-2.55 (m, 5H), 1.83-1.68 (m, 3H), 1.61-1.51 (m, 2H), 1.39-1.27 (m, 26H), 0.89 (t, J=6.8 Hz, 3H). ESI-MS: m/z $[M+Na]^+$ calc'd for $C_{37}H_{61}N_5O_8Na^+$: 726.44, found: 726.5

Compound 85a (n=11): A solution of 84a (0.45 g, 0.53 mmol) in butanol (6.0 ml) was treated with ethylenediamine (6.0 ml) and stirred at 90° C. for 3 h. The mixture was concentrated under high vacuo and purified by flash chromatography (dichloromethane/methanol, 3:1, v/v) to give 85a (0.26 g, 68%). $^1$H NMR (500 MHz, MeOD): δ=4.35 (d, J=8.0 Hz, 1H, H-1), 3.93 (dd, J=10.6, 5.0 Hz, 1H), 3.75 (dd, 1H), 3.63-3.47 (m, 4H), 3.48-3.43 (m, 4H), 3.48-3.24 (m, 7H), 3.23-3.11 (m, 1H), 3.06 (dd, J=13.1, 9.0 Hz, 1H), 3.01-2.91 (m, 1H), 2.63 (dd, J=10.1, 8.0 Hz, 1H), 1.73-1.63 (m, 1H), 1.63-1.51 (m, 4H), 1.42-1.26 (m, 42H), 0.89 (t, J=6.8 Hz, 3H). ESI-MS: m/z $[M+H]^+$ calc'd for $C_{38}H_{77}N_5O_6H^+$: 700.59, found: 700.5

Compound 85b (n=2): A solution of 84b (0.17 g, 0.24 mmol) in butanol (4.0 ml) was treated with ethylenediamine (4.0 ml) and stirred at 90° C. for 3 h. The mixture was concentrated under high vacuo and purified by flash chromatography (dichloromethane/methanol, 3:1, v/v) to give 85b (0.089 g, 65%). 1H NMR (500 MHz, MeOD): δ=4.23 (d, J=8.0 Hz, 1H, H-1), 3.90 (dd, J=10.5, 4.9 Hz, 1H), 3.66 (dd, J=10.5, 3.9 Hz, 1H), 3.61-3.42 (m, 7H), 3.38 (t, J=6.7 Hz, 4H), 3.26 (dd, J=10.0, 8.7 Hz, 1H), 3.15-3.09 (m, 1H), 2.94 (dd, J=14.2, 2.4 Hz, 1H), 2.68-2.55 (m, 5H), 1.83-1.68 (m, 3H), 1.61-1.51 (m, 2H), 1.39-1.27 (m, 26H), 0.89 (t, J=6.8 Hz, 3H). ESI-MS: m/z $[M+Na]^+$ calc'd for $C_{29}H_{59}N_5O_6Na^+$: 596.44, found: 596.5

Compound 73: A solution of 85a (0.07 g, 0.096 mmol) in methanol (4.0 ml) was treated with a catalytic amount of $Pd(OH)_2/C$ (10% wt.) and stirred under $H_2$ gas atmosphere for 1 h. The resulting solution was filtered, concentrated in vacuo and purified by reverse-phase C18 silica gel to give 73 (0.048 g, 72%). $^1$H NMR (500 MHz, MeOD): δ=4.35 (d, J=7.1 Hz, 1H, H-1), 3.93 (dd, J=10.5, 6.7 Hz, 1H), 3.75-3.64 (m, 1H), 3.63-3.47 (m, 4H), 3.47-3.42 (m, 4H), 3.41-3.23 (m, 7H), 3.23-3.11 (m, 2H), 3.06 (dd, J=13.1, 9.0 Hz, 1H), 3.01-2.91 (m, 1H), 2.65 (dd, J=9.6, 7.1 Hz, 1H, H-2), 1.73-1.63 (m, 1H), 1.63-1.51 (m, 4H), 1.42-1.26 (m, 41H), 0.89 (t, J=6.8 Hz, 3H); $^{13}$C NMR (126 MHz, MeOD): δ=103.11 (C-1), 78.97, 75.98, 73.75, 72.95, 71.21, 69.81, 68.27, 56.79, 56.67, 55.66, 54.70, 53.39, 40.24, 38.62, 35.53, 31.68, 30.23, 29.80, 29.39, 29.36, 29.33, 29.25, 29.22, 29.08, 29.06, 27.26, 26.53, 26.38, 25.88, 22.34, 13.07. HRMS: m/z $[M+Na]^+$ calc'd for $C_{38}H_{79}N_3O_6Na^+$: 696.5867, found: 696.580

Compound 74: A solution of 85b (0.082 g, 0.14 mmol) in methanol (4.0 ml) was treated with a catalytic amount of $Pd(OH)_2/C$ (10% wt.) and stirred under $H_2$ gas atmosphere for 1 h. The resulting solution was filtered, concentrated in vacuo and purified by reverse-phase C18 silica gel to give 74 (0.054 g, 69%). $^1$H NMR (500 MHz, MetOD): δ=4.23 (d, J=8.0 Hz, 1H, H-1), 3.90 (dd, J=10.5, 4.9 Hz, 1H), 3.66 (dd, J=10.5, 3.9 Hz, 1H), 3.61-3.42 (m, 7H), 3.38 (t, J=6.7 Hz, 4H), 3.26 (dd, J=10.0, 8.7 Hz, 1H), 3.15-3.09 (m, 1H), 2.94 (dd, J=14.2, 2.4 Hz, 1H), 2.68-2.55 (m, 5H), 1.83-1.68 (m, 3H), 1.61-1.51 (m, 2H), 1.39-1.27 (m, 26H), 0.89 (t, J=6.8 Hz, 3H); $^{13}$C NMR (126 MHz, MeOD): δ=102.52, 78.97, 75.66, 74.45, 72.63, 71.24, 69.83, 68.35, 56.70, 54.70, 51.44, 49.10, 31.66, 29.37, 29.34, 29.26, 29.19, 29.06, 26.26, 25.83, 22.32, 13.04. HRMS: m/z $[M+K]^+$ calc'd for $C_{29}H_{61}N_3O_6Na^+$: 571.4458, found: 571.42

Compound 86a (n=11): A solution of 32 (0.20 g, 0.39 mmol) in dry DCM was treated with 89a (n=11) (0.088 g, 0.39 mmol) and stirred overnight at 0° C. to RT. Two drops of acetic acid and sodium borohydride, $NaBH_4$ (0.045 g, 1.161 mmol) in methanol were then added to the mixture and stirred further for 2 h at RT. The resulting mixture was concentrated in vacuo, extracted with ethyl acetate and purified by flash chromatography (dichloromethane/methanol, 7:1, v/v) to afford 86a (0.20 g, 69%). $^1$H NMR (300 MHz, MeOD): δ=4.60 (d, J=8.1 Hz, 1H, H-1), 3.98 (dd, J=8.9, 4.2 Hz, 1H), 3.74 (dd, J=10.5, 3.8 Hz, 1H), 3.64-3.38 (m, 11H), 3.36-3.24 (m, 4H), 3.18-3.04 (m, 1H), 3.02-2.90 (m, 1H), 2.69 (dd, J=10.2, 8.1 Hz, 1H, H-2), 1.72-1.50 (m, 6H), 1.48-1.28 (m, 42H), 0.88 (t, J=6.9 Hz, 3H). ESM-MS: m/z $[M+H]^+$ calc'd for $C_{38}H_{75}N_7O_6H^+$: 726.58, found: 726.7

Compound 86b (n=11): A solution of 32 (0.15 g, 0.29 mmol) in dry DCM was treated with 89b (n=2) (0.03 g, 0.30 mmol) and stirred overnight at 0° C. to RT. Two drops of acetic acid and sodium borohydride, $NaBH_4$ (0.041 g, 0.91 mmol) in methanol were then added to the mixture and stirred further for 2 h at RT. The resulting mixture was concentrated in vacuo, extracted with ethyl acetate and purified by flash chromatography (dichloromethane/methanol, 7:1, v/v) to afford 86b (0.11 g, 64%). $^1$H NMR (300 MHz, MeOD): δ=4.43 (d, J=8.1 Hz, 1H, H-1), 3.99 (dd, J=10.6, 4.2 Hz, 1H), 3.89 (dd, J=11.9, 2.0 Hz, 1H), 3.77-3.65 (m, 2H), 3.65-3.23 (m, 13H), 3.22-3.06 (m, 1H), 3.02-2.89 (m, 1H), 2.55 (dd, J=10.4, 8.1 Hz, 1H, H-2) 1.90-1.77 (m, 2H), 1.65-1.52 (m, 2H), 1.45-1.23 (m, 26H), 0.91 (t, J=6.9 Hz, 3H). ESI-MS: m/z $[M+Na]^+$ calc'd for $C_{29}H_{57}N_7O_6Na^+$: 622.43, found: 622.5

Compound 75: A solution of 86a (0.20 g, 0.28 mmol) in methanol (5.0 ml) was treated with a catalytic amount of $Pd(OH)_2/C$ (10% wt.) and stirred under $H_2$ g as atmosphere for 1 h. The resulting solution was filtered, concentrated in vacuo and purified by reverse-phase C18 silica gel to give 75 (0.14 g, 76%). $^1$H NMR (300 MHz, MeOD): δ=4.60 (d, J=8.1 Hz, 1H, H-1), 3.98 (dd, J=8.9, 4.2 Hz, 1H), 3.74 (dd, J=10.5, 3.8 Hz, 1H), 3.64-3.38 (m, 11H), 3.36-3.24 (m, 4H), 3.18-3.04 (m, 1H), 3.02-2.90 (m, 1H), 2.69 (dd, J=10.2, 8.1 Hz, 1H, H-2), 1.72-1.50 (m, 61-1), 1.48-1.28 (m, 42H), 0.88 (t, J=6.9 Hz, 3H); 13C NMR (75 MHz, MeOD) δ=102.71 (C-1), 80.40, 77.38, 74.55, 72.88, 72.76, 71.54, 69.35, 63.97, 58.21, 52.67, 52.52, 33.16, 30.90, 30.86, 30.76, 30.71, 30.57, 30.38, 30.02, 29.26, 28.10, 27.93, 27.33, 23.83, 14.60. HRMS: m/z [M+K]$^+$ calc'd for $C_{38}H_{79}N_3O_6K^+$: 712.5606, found: 712.559.

Compound 76: A solution of 86b (0.11 g, 0.18 mmol) in methanol (5.0 ml) was treated with a catalytic amount of Pd(OH)$_2$/C (10% wt.) and stirred under H$_2$ g as atmosphere for 1 h. The resulting solution was filtered, concentrated in vacuo and purified by reverse-phase C18 silica gel to give 76 (0.072 g, 72%). 1H NMR (300 MHz, MeOD): δ=4.43 (d, J=8.1 Hz, 1H, H-1), 3.99 (dd, J=10.6, 4.2 Hz, 1H), 3.89 (dd, J=11.9, 2.0 Hz, 1H), 3.77-3.65 (m, 2H), 3.65-3.23 (m, 13H), 3.22-3.06 (m, 1H), 3.02-2.89 (m, 1H), 2.55 (dd, J=10.4, 8.1 Hz, 1H, H-2) 1.90-1.77 (m, 2H), 1.65-1.52 (m, 2H), 1.45-1.23 (m, 26H), 0.91 (t, J=6.9 Hz, 3H); 13C NMR (75 MHz, MeOD): δ=104.10 (C-1), 80.58, 78.18, 75.72, 72.70, 72.00, 71.52, 69.65, 64.36, 62.66, 58.18, 33.10, 30.80, 30.77, 30.62, 30.49, 29.35, 27.26, 23.76, 14.47. HRMS: m/z [M+Na]$^+$ calc'd for $C_{29}H_{61}N_3O_6Na^+$: 571.4458, found: 571.442

1-O-Hexadecyl-2-O-methyl-3-O-(4'-benzyl-2',6'-diamino-2',6'-dideoxy-β-L-glucopyranosyl)-sn-glycerol (70)

$^1$H NMR (500 MHz, Methanol-d$_4$) δ 7.43-7.20 (m, 5H, aromatic proton), 4.78 (dd, J=11.2 Hz, 2H, benzyl CH$_2$), 4.23 (d, J=7.9 Hz, 1H, β-H$_1$), 3.93-3.98 (m, 1H, —CH—O—CH$_3$), 3.67-3.45 (m, 10H, —OCH$_3$, H$_5$), 3.36-3.11 (m, 2H), 2.95 (dd, J=13.4, 2.8 Hz, 1H, H$_{6b}$), 2.72-2.55 (m, 2H, H$_2$, H$_{6a}$), 1.58-1.54 (m, 2H, —OCH$_2$CH$_2$—), 1.28 (broad s, 26H, lipid tail), 0.89 (t, J=6.8 Hz, 3H, terminal lipid CH$_3$). $^{13}$C NMR (126 MHz, MeOD) δ 138.43, 127.95, 127.38, 103.65, 79.45, 79.33, 76.61, 75.73, 74.24, 71.24, 69.66, 68.81, 57.37, 56.69, 42.42, 31.65, 29.36, 29.33, 29.15, 29.05, 25.80, 22.31, 13.01.

1-O-Hexadecyl-2-O-methyl-3-O-(2',6'-diamino-2',6'-dideoxy-α-L-glucopyranosyl)-sn-glycerol (71)

$^1$H NMR (500 MHz, Methanol-d$_4$) δ 4.77 (d, J=3.7 Hz, 1H, α-H$_1$), 3.83-3.73 (m, 1H, —CH—O—CH$_3$), 3.61-3.39 (m, 11H), 3.14 (dd, J=9.8, 8.8 Hz, 1H, H$_3$), 2.97 (dd, J=13.4, 3.1 Hz, 1H, H$_{6a}$), 2.71 (dd, J=13.4, 7.1 Hz, 1H, H$_{6b}$), 2.56 (dd, J=9.9, 3.7 Hz, 1H, H$_2$), 1.63-1.49 (m, 2H, —OCH$_2$CH$_2$—), 1.29 (broad s, 26H, lipid tail), 0.89 (t, J=6.9 Hz, 3H, terminal lipid CH$_3$). $^{13}$C NMR (126 MHz, MeOD) δ 99.09, 79.03, 74.76, 72.54, 72.06, 71.22, 69.85, 66.54, 56.82, 55.91, 42.38, 31.64, 29.34, 29.32, 29.03, 25.83, 22.30, 12.99.

1-O-Hexadecyl-2-O-methyl-3-O-(4'-benzyl-2',6'-diamino-2',6'-dideoxy-α-L-glucopyranosyl)-sn-glycerol (72)

$^1$H NMR (300 MHz, Methanol-d$_4$) δ 7.41-7.07 (m, 5H, aromatic proton), 4.85 (d, J=11.3, 1H, benzyl CH$_2$), 4.68 (d, J=3.6, 1H, α-H$_1$), 4.55 (dd, J=11.3, 1H, benzyl CH$_2$), 3.72-3.60 (m, 1H, —CH—O—CH$_3$), 3.58-3.28 (m, 12H), 3.07 (dd, J=10.0, 1.5 Hz, 1H, H$_{6b}$), 2.59-2.46 (m, 2H, H$_2$, H$_{6a}$), 1.55-1.36 (m, 2H, —OCH$_2$CH$_2$), 1.19 (broad s, 26H), 0.80 (t, J=6.7, 3H, terminal lipid CH$_3$). $^{13}$C NMR (75 MHz, MeOD) δ 139.99, 129.31, 128.82, 100.36, 80.83, 80.40, 76.80, 75.66, 73.08, 72.71, 71.14, 67.78, 58.27, 57.68, 43.72, 33.12, 30.83, 30.63, 30.52, 27.29, 23.78, 14.51.

4.3. Biological Methods 4.3.1. Effect of GAELs on Viability of Epithelial Cancer Cell Lines The cell lines were cultured from frozen stocks originally obtained from ATCC. MDA-MB-231, JIMT-1, DU145, U81, U251 cells were grown in DMEM medium. BT474, A2780s, A2780cp cells were grown in DMEM/F12 medium supplemented with 10% FBS. MiaPaCa2 was cultured in DMEM supplemented with 10% FBS and 2.5% horse serum. PC3 cells were cultured in F12K medium supplemented with 10% FBS. All the media were supplemented with penicillin/streptomycin.

The effects of the GAELs on the viability of the various epithelial cancer cell lines was determined as previously described. Briefly, equal numbers of the cells were dispersed into 96-well plates. After 24 h, the cells were incubated with the compounds (0-30 μM) for 48 h. At the end of the incubation, MTS reagent (20% vol/vol) was added and the plates were incubated for 1-4 h. The OD$_{490}$ was read with a plate reader. Wells with media but no cells were treated in similar fashion and the values utilized as blank. The results represent the mean±standard deviation of 6 independent determinations.

4.3.1.2. Isolation of primary epithelial ovarian cancer cells (EOC) from ascites fluid of ovarian cancer patients. The isolation of EOC cells from the ascites fluid of ovarian cancer patients was performed as described by Shepherd et al 2007, Nature protocols 1, 2643-2649). The cells were grown in DMEM/F12 supplemented with 10% FBS medium.

4.3.2. Isolation of breast cancer stem cells from BT-474, prostate cancer stem cells from DU145, and ovarian cancer stem cells from A2780cp cell lines and determination of the effect of GAELs on the viability of the cancer stem cells.

A population enriched in BT474 breast cancer stem cells or DU145 prostate cancer stem cells or A2780 ovarian cancer stem cells was obtained by staining the cells for aldehyde dehydrogenase using the Aldefluor assay kit from Stem Cell Technologies (Vancouver, BC, Canada) according to the instruction of the manufacturer with the appropriate controls. The stained cells were sorted from the bulk population by flow cytometry on a 4 laser MoFloXPP high speed/pressure cell sorter. The cells were pelleted by centrifugation. BT474 cells were resuspended into ultra-low adhesion plates in mammocult medium. The DU145 stem cells were resuspended in their growth medium (DMEM/F12 medium supplemented with 20 ng/ml EGF, and 10 ng/ml basic FGF, 5 μg/ml insulin, 0.4% BSA, with 1% antibiotics; (Salvatori et al 2012, PLos One 7(2) e31467.doi: 10.1371/journal.pone.0031476). The dishes were incubated at 37 C in a CO$_2$ incubator for 4-6 days for spheroid formation.

The spheres are separated from single cells with a 40 μm nylon cell strainer. The spheres retained in the strainer were washed with PBS and trypsinised to obtain single cells. The cell numbers were counted with a Coulter ZM counter and the cells were dispersed into 48-well low adhesion plates (Grenier) in a volume of 500 ul. The cells were incubated for 4-6 days to allow for formation of spheroids. Subsequently, the stock GAELs in ethanol were diluted to twice the final concentration in the media and a volume of 500 μl was added to the wells. Wells with growth medium but no cells were treated as the wells with cells. After 6 days incubation, MTS reagent, (2% vol/vol) was added to each well and the plates were incubated for 1-4 hrs for formation of colour. The $OD_{490}$ were read in a Molecular Device absorbance plate reader using the SpectroMax software.

4.3.3 Tolerability Studies

A total of 30 female Rag2 mice were individually weighed and administered compound 56 intravenously or orally according to individual body weight. The mice was monitored for behavioural changes, body weight for 14 days. All mice were sacrificed on day 15 and necropsy was performed.

The scope of the claims should not be limited by the preferred embodiments set forth in the examples, but should be given the broadest interpretation consistent with the description as a whole.

TABLE 1

Cytotoxicity of compounds 1-10 and Gln 11 on a panel of human epithelial cancer cell lines: breast (BT474, JIMT1, MDA-MB-231), pancreas (MiaPaCa2) and prostrate (DU145, PC3). The $CC_{50}$ value is defined as the concentration required to decrease cell viability by 50% relative to the untreated control, while the $CC_{90}$ values is defined as the concentration required to decrease cell viability by 90% relative to untreated control. The values were obtained by estimating the drug concentration at 50% and 10% viability on the y-axis using line plots. NT—Not tested

A.

| | $CC_{50}$ values (µM) | | | | | |
|---|---|---|---|---|---|---|
| Drugs | MD 231 | DU 145 | JIMT1 | MiaPaCa2 | PC3 | BT474 |
| 1 | 3.0 | 5.2 | 3.5 | 3.5 | 3.5 | 7.5 |
| 2 | 5.5 | 6.0 | 4.2 | 7.0 | 11 | 11.5 |
| 3 | 20.0 | >30 | >30 | >30 | 15.0 | NT |
| 4 | 4.5 | 6.0 | 4.0 | 6.5 | 8 | 8.5 |
| 5 | >30 | >30 | >30 | >30 | >30 | >30 |
| 6 | 11.0 | 12.5 | 9.5 | 11.5 | 6.0 | 22 |
| 7 | 12.0 | 17.5 | 14.0 | 15.0 | 9.5 | 25 |
| 8 | 6.0 | 6.0 | 5.5 | 8.5 | 9 | 15.5 |
| 9 | >30 | >30 | >30 | >30 | >30 | >30 |
| 10 | 16 | 14 | 12.5 | 18 | 20 | 23 |
| 11 (Gln) | NT | 10 | 9 | 9 | 13.5 | 8 |

B

| | $CC_{90}$ values (µM) | | | | | |
|---|---|---|---|---|---|---|
| Drugs | MD 231 | DU 145 | JIMT1 | MiaPaCa2 | PC3 | BT474 |
| 1 | 4.5 | 7.4 | 4.9 | 6.5 | 6.0 | 9.5 |
| 2 | 7.0 | 8.5 | 6.5 | 12 | 14 | 14.0 |
| 3 | >30 | >30 | >30 | >30 | 30.0 | NT |
| 4 | 7.0 | 8.5 | 6.0 | 13 | 14 | 17.5 |
| 5 | >30 | >30 | >30 | >30 | >30 | >30 |
| 6 | 15.0 | 18 | 13.5 | 18.5 | 15.0 | 28 |
| 7 | 17.5 | 25.0 | 19.0 | 28.0 | 17.0 | >30 |
| 8 | 9 | 9 | 7.5 | 14 | 14 | 28 |
| 9 | >30 | >30 | >30 | >30 | >30 | >30 |
| 10 | 19 | 19 | 15 | 29 | 29 | 29 |
| 11 (Gln) | NT | 15 | 16 | 18 | 28 | 13 |

TABLE 2

Cytotoxicity of compounds 56, L-Gln 69 and Gln 11 on a panel of human epithelial cancer cell lines: breast (BT474, JIMT1, MDA-MB-231), pancreas (MiaPaCa2) and prostrate (DU145, PC3). The $CC_{50}$ value is defined as the concentration required to decrease cell viability by 50% relative to the untreated control, while the $CC_{90}$ values is defined as the concentration required to decrease cell viability by 90% relative to untreated control. The values were obtained by estimating the drug concentration at 50% and 10% viability on the y-axis using line plots. NT—Not tested.

A

| | $CC_{50}$ values (µM) | | | | | |
|---|---|---|---|---|---|---|
| | MDA-MB-231 | DU 145 | JIMT1 | MiaPaCa2 | PC3 | BT 474 |
| 56. | 4.8 | 8.2 | 5.5 | 8.5 | 11.0 | |
| 69 | 11.0 | 12.5 | 6.5 | 7.5 | 12.5 | |
| 11 | NT | 10 | 9 | 9 | 13.5 | 8 |

B

| | $CC_{90}$ values (µM) | | | | | |
|---|---|---|---|---|---|---|
| | MDA-MB-231 | DU 145 | JIMT1 | MiaPaCa2 | PC3 | BT 474 |
| 56 | 6.5 | 12.5 | 6 | 12.5 | 14.0 | |
| 69 | 17 | 16 | 11 | 18 | 16 | |
| 11 | NT | 15 | 16 | 18 | 28 | 13 |

TABLE 3

Clinical parameters of EOC samples from patient ascites.

| Patient Ascites sample | Diagnosis | FIGO Stage | Treatment prior to ascites collection | Platinum resistance status at time Ascites sample collected |
|---|---|---|---|---|
| EOC216B | Adeno-carcinoma | Not indicated | No surgery. No chemotherapy | Not clinically resistant |
| EOC216H | Adeno-carcinoma | Not indicated | Carboplatin/ Paclitaxel (3 cycles) Caelyx (1 cycle) | Clinically resistant to platinum-base chemotherapy |
| EOC258 | High grade Serous | Not indicated | No surgery. No chemotherapy | Not clinically resistant |

TABLE 4

CC$_{50}$ values for GAELs against primary ovarian cancer cells. Cytotoxicity of compounds 1, 56 and 69 on primary ovarian cancer cells isolated from ascites of ovarian cancer patients. The CC$_{50}$ value is defined as the concentration required to decrease cell viability by 50% relative to the untreated control, while the CC$_{90}$ values is defined as the concentration required to decrease cell viability by 90% relative to untreated control. The values were obtained by estimating the drug concentration at 50% and 10% viability on the y-axis using line plots. NT—Not tested

| | CC$_{50}$ values (µM) | | | | | |
|---|---|---|---|---|---|---|
| | EOC 216H | | EOC216B | | EOC258 | | EOC260 |
| | Adherent | Spheroid | Adherent | Spheroid | Adherent | Spheroid | Adherent |
| 1 | 0.15 | 0.21 | 0.24 | 0.6 | 0.3 | 0.6 | 0.2 |
| 56 | 1.1 | 1.0 | 0.5 | 1.2 | 0.55 | 1.65 | 0.6 |
| 69 | 1.02 | 1.5 | 0.56 | 1.25 | 1.4 | 1.2 | 0.3 |

TABLE 5

Cytotoxicity of compounds 1, 56, 69, 70-72 on a panel of human epithelial cancer cell lines: breast (BT474, JIMT1, MDA-MB-231), pancreas (MiaPaCa2) and prostrate (DU145, PC3). The CC$_{50}$ value is defined as the concentration required to decrease cell viability by 50% relative to the untreated control, while the CC$_{90}$ values is defined as the concentration required to decrease cell by 90% relative to untreated control. The values were viability obtained by estimating the drug concentration at 50% and 10% viability on the y-axis using line plots. NT—Not tested

| | JIMT1 | MDA-MB-231 | DU-145 | MIapaca2 | PC3 | B1474 |
|---|---|---|---|---|---|---|
| | | | CC$_{50}$ | | | |
| 1 | 3.5 | 3.0 | 5.2 | 3.5 | 3.5 | 7.5 |
| 56 | 5.5 | 4.8 | 8.2 | 8.5 | 11.0 | NT |
| 69 | 6.5 | 11.0 | 12.5 | 7.5 | 12.5 | NT |
| 70 | 2.0 | 4.0 | 3.6 | 5.0 | NT | NT |
| 72 | 2.0 | 4.0 | 3.6 | 4.5 | NT | NT |
| 71 | 4.0 | 5.5 | 6.0 | 6.0 | NT | NT |
| | | | CC$_{90}$ | | | |
| 1 | 4.9 | 4.5 | 7.4 | 6.5 | 6.0 | NT |
| 56 | 6 | 6.5 | 12.5 | 12.5 | 14 | NT |
| 69 | 11 | 17.0 | 16 | 18 | 16 | NT |
| 70 | 3.5 | 4.9 | 4.9 | 7.1 | NT | NT |
| 72 | 3.5 | 4.9 | 4.9 | 7.0 | NT | NT |
| 71 | 6.5 | 7.5 | 8.0 | 15.0 | NT | NT |

TABLE 6

Cytotoxicity of compounds 73-76 on a panel of human epithelial cancer cell lines: breast (BT474, JIMT1, MDA-MB-231), pancreas (MiaPaCa2) and prostrate (DU145, PC3). The CC50 value is defined as the concentration required to decrease cell viability by 50% relative to the untreated control, while the CC90 values is defined as the concentration required to decrease cell viability by 90% relative to untreated control. The values were obtained by estimating the drug concentration at 50% and 10% viability on the y-axis using line plots. NT—Not tested

| | DU145 | | MB-MDA-231 | | JIMT1 | | MiaPaCa2 | | BT474 | | PC3 | |
|---|---|---|---|---|---|---|---|---|---|---|---|---|
| CODE | CC$_{50}$ | CC$_{90}$ | CC$_{50}$ | CC$_{90}$ | CC$_{50}$ | CC$_{90}$ | CC$_{50}$ | CC$_{90}$ | CC$_{50}$ | CC$_{90}$ | CC$_{50}$ | CC$_{90}$ |
| 73 | 3.8 | 4.8 | 1.5 | 3.8 | 3.4 | 4.6 | 4.0 | 6.6 | 1.6 | 4.2 | 2.0 | 3.2 |
| 74 | 16.5 | 20.0 | 13.5 | 19.5 | 13.5 | 18.5 | 18.5 | >20 | >20 | >20 | 12.5 | 20.0 |
| 76 | 18.5 | >20 | 17.5 | >20 | 12.5 | 16.5 | 14.5 | >20 | >20 | >20 | 14.5 | >20 |
| 75 | 7.5 | 9.5 | 5.5 | 9.5 | 8.0 | 9.5 | 8.5 | 12 | 13.5 | 16.5 | 8.5 | 11.5 |

The invention claimed is:

1. A method of killing cancer stem cells and cancer stem cell spheroids or aggregates in an individual having a cancer comprising cancer stem cells that are refractory to treatment with existing apoptosis-inducing agents comprising:

administering to said individual having a cancer comprising cancer stem cells that are refractory to treatment with existing apoptosis-inducing agents an effective amount of a compound selected from the group consisting of:

a) Formula (I): 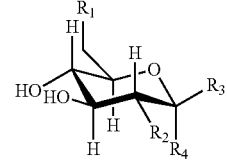

wherein:
$R_1 = NH_2$, $R_2 = b$, $R_3 = a$, $R_4 = H$;
$R_1 = NH_2$, $R_2 = NH_2$, $R_3 = d$, $R_4 = H$;
$R_1 = NH_2$, $R_2 = NH_2$, $R_3 = e$, $R_4 = H$;
$R_1 = NH_2$, $R_2 = NH_2$, $R_3 = f$, $R_4 = H$
$R_1 = NH_2$, $R_2 = NH_2$, $R_3 = g$, $R_4 = H$;
$R_1 = NH_2$, $R_2 = NH_2$, $R_3 = h$, $R_4 = H$; or
$R_1 = NH_2$, $R_2 = NH_2$, $R_3 = i$, $R_4 = H$, where a-i are as follows:

d) Formula (IV):

$$\text{(IV)}$$

wherein:

R = a, R₁ = b, R₂ = c;
R = b, R₁ = a, R₂ = d; or
R = b, R₁ = a, R₂ = c, where a-d are as follows:

a, b, c, d e) Formula (V):

$$\text{(V)}$$

wherein:

R = a, R₁ = H;
R = b, R₁ = H;
R = H, R₁ = a; or
R = H, R₁ = b, where a and b are as follows:

a, b b) Formula (II):

$$\text{(II)}$$

c) Formula (III):

$$\text{(III)}$$

f) Formula (I'):

D-glucose, D-galactose

D-mannose, D-allose

-continued

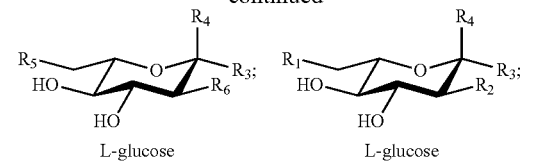

L-glucose    L-glucose

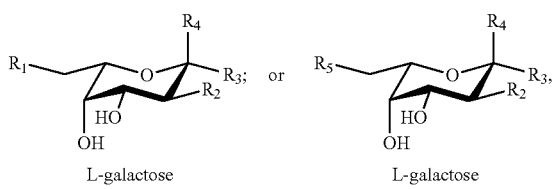

L-galactose   L-galactose wherein:
$R_1 = NH_2, R_2 = b, R_3 = a, R_4 = H$;
$R_1 = NH_2, R_2 = NH_2, R_3 = d, R_4 = H$;
$R_1 = NH_2, R_2 = NH_2, R_3 = e, R_4 = H$;
$R_1 = NH_2, R_2 = NH_2, R_3 = f, R_4 = H$
$R_1 = NH_2, R_2 = NH_2, R_3 = g, R_4 = H$;
$R_1 = NH_2, R_2 = NH_2, R_3 = h, R_4 = H$; or
$R_1 = NH_2, R_2 = NH_2, R_3 = i, R_4 = H$,
$R_3 = H, R_4 = a, R_5 = NH_2, R_6 = NH_2$;
$R_3 = a, R_4 = H, R_5 = NH_2, R_6 = NH_2$;
$R_3 = c, R_4 = H, R_5 = NH_2, R_6 = NH_2$;
$R_3 = d, R_4 = H, R_5 = NH_2, R_6 = NH_2$;
$R_3 = e, R_4 = H, R_5 = NH_2, R_6 = NH_2$;
$R_3 = f, R_4 = H, R_5 = NH_2, R_6 = NH_2$;
$R_3 = g, R_4 = H, R_5 = NH_2, R_6 = NH_2$;
$R_3 = h, R_4 = H, R_5 = NH_2, R_6 = NH_2$;
$R_3 = i, R_4 = H, R_5 = NH_2, R_6 = NH_2$; or
$R_3 = a, R_4 = H, R_5 = NH_2, R_6 = b$;

where a-i are as follows:

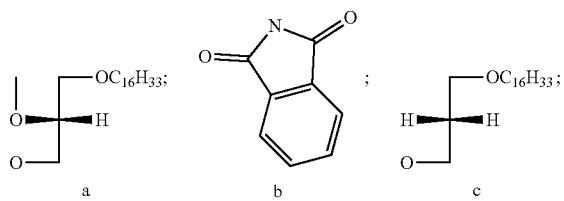

a    b    c

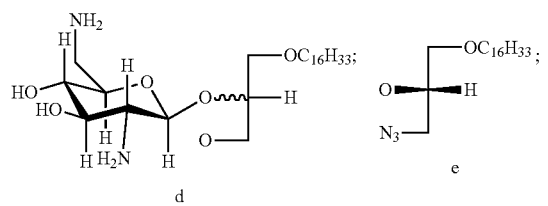

d    e

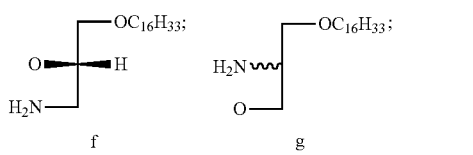

f    g

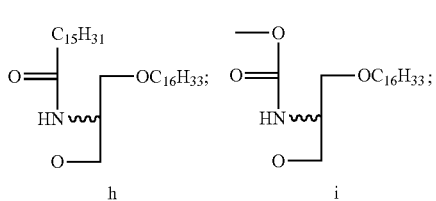

h    i g) Formula (II'):

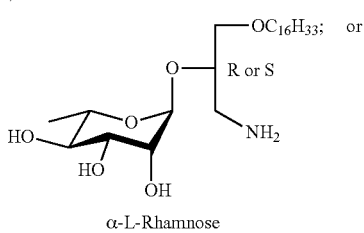

α-L-Rhamnose

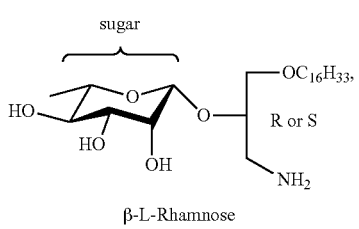

β-L-Rhamnose wherein the sugar is selected from the group consisting of α-L-rhamnose; β-L-rhamnose; 6-deoxy-α-D-galactose; 6-deoxy-β-D-galactose; 6-deoxy-α-L-galactose; 6-deoxy-β-L-galactose; 6-deoxy-α-D-glucose; 6-deoxy-β-D-glucose; 6-deoxy-α-L-glucose; 6-deoxy-β-L-glucose; 6-deoxy-α-D-mannose; 6-deoxy-β-D-mannose; 6-deoxy-α-L-mannose; and 6-deoxy-β-L-mannose;

h) Formula (III'):

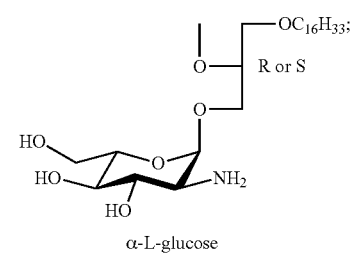

α-L-glucose

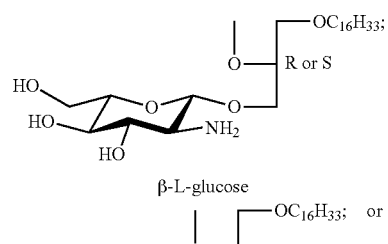

β-L-glucose

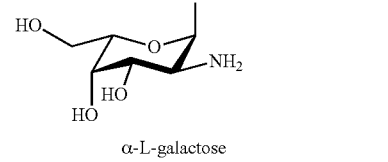

α-L-galactose

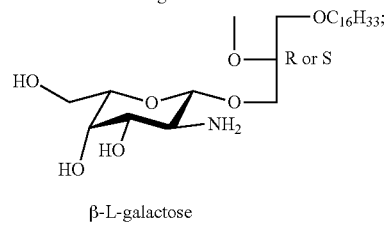

β-L-galactose

-continued i) Formula (IV'):

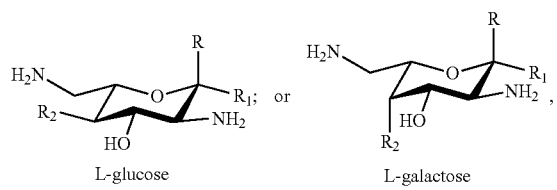

L-glucose        L-galactose wherein:
R = a, R₁ = b, R₂ = c;
R = b, R₁ = a, R₂ = d; or
R = b, R₁ = a, R₂ = c, where a-d are as follows:

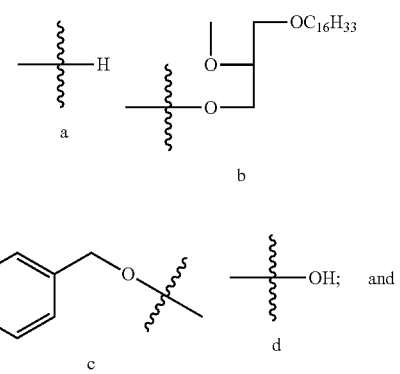

j) Formula (V'):

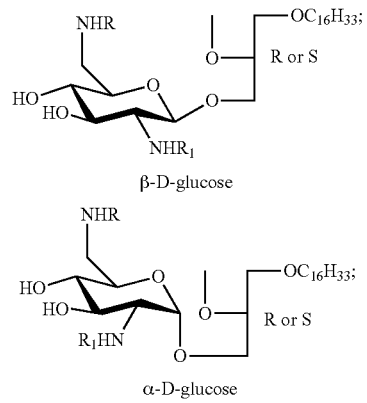

β-D-glucose

α-D-glucose

α-L-glucose

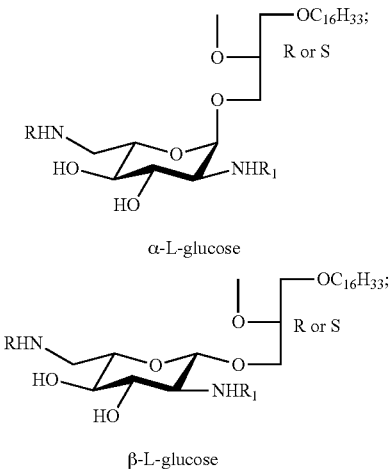

β-L-glucose

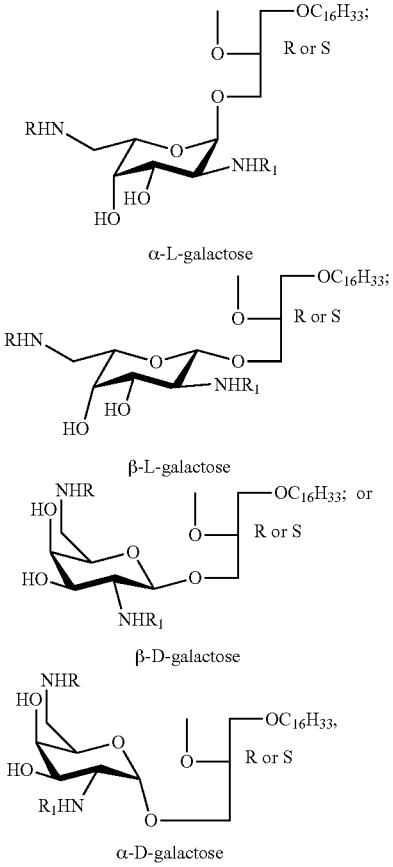

α-L-galactose

β-L-galactose

β-D-galactose

α-D-galactose wherein:
R = a, R₁ = H;
R = b, R₁ = H;
R = H, R₁ = a; or
R = H, R₁ = b, where a and b are as follows:

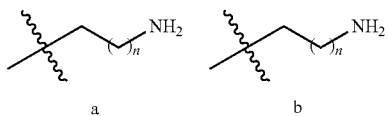

n = 1, 2, 3, ......, 16, said compound disintegrating cancer stem cell spheroids and aggregates, thereby killing the cancer stem cells.

2. The method according to claim 1 wherein the cancer is a recurring cancer or a resistant cancer.

3. The method according to claim 1 wherein the cancer is metastasized or advanced stage cancer.

4. The method according to claim 1 wherein the compound is selected from the group consisting of: 1-O-Hexadecyloxy-2S/R-amino-3-(-2'-amino-2'-deoxy-β-D-glucopyranosyl)-glycerol; 1-O-Hexadecyloxy-2R-(-α-L-rhamnopyranosyl)-3-amino glycerol; 1-O-Hexadecyloxy-2R—O-methyl-(2'amino-2'deoxy-α-L-glucopyranosyl)-3-amino glycerol; 1-O-Hexadecyl-2-O-methyl-3-O-(4'-benzyl-2',6'-diamino-2',6'-dideoxy-β-L-glucopyranosyl)-sn-glycerol; 1-O-Hexadecyl-2-O-methyl-3-O-(2',6'-diamino-2',6'-dideoxy-α-L-glucopyranosyl)-sn-glycerol; 1-O-Hexadecyl-2-O-methyl-3-O-(4'-benzyl-2',6'-diamino-2',6'- dideoxy-α-L-glucopyranosyl)-sn-glycerol; 1-O-Hexadecyl-2-O-methyl-3-O-[6'-N-(12-aminododecyl)-2',6'-diamino-2',6'-dideoxy-glucopyranoside]-sn-glycerol; 1-4-Hexadecyl-2-O-methyl-3-O-[6'-N-(3-aminopropyl)-2',6'-diamino-2',6'-dideoxy-glucopyranoside]-sn-glycerol; 1-O-Hexadecyl-2-O-methyl-3-O-(2'-N-(12-aminododecyl)-2',6'-diamino-2',6'-dideoxy-glucopyranoside]-sn-glycerol and 1-O-Hexadecyl-2-O-methyl-3-O-[2'-N-(3-aminopropyl)-2',6'-diamino-2',6'-dideoxy-glucopyranoside]-sn-glycerol and the corresponding D-galactose-, D-allose, D-mannose analogs of formula (I'), the corresponding β-L-rhamnose analog of formula (II'') the corresponding β-L-glucose, α-L-galactose or β-L-galactose analog of formula (III'), the corresponding L-galactose analog of formula (IV') or the corresponding α-D-glucose, α-L-glucose, β-L-glucose, α-L-galactose, β-L-galactose, β-D-galactose or α-D-galactose analog of formula (V').

5. The method according to claim 1 wherein the effective amount is between about 0.1 mg/Kg body weight to 5 mg/Kg body weight and is delivered into the patient intravenously, orally, peritoneally or topically or a combination thereof.

6. The method according to claim 1 wherein the cancer is breast cancer, pancreatic cancer, prostate cancer or ovarian cancer.

7. The method according to claim 1 wherein the cancer is selected from the group consisting of pancreatic cancer, breast cancer, ovarian cancer, prostate cancer, small cell lung cancer, colon cancer, liver cancer, skin cancer and brain cancer.

* * * * *